United States Patent
Lücking et al.

(10) Patent No.: US 10,729,680 B2
(45) Date of Patent: *Aug. 4, 2020

(54) 5-SUBSTITUTED 2-(MORPHOLIN-4-YL)-1,7-NAPHTHYRIDINES

(71) Applicant: BAYER PHARMA AKTIENGESELLSCHAFT, Berlin (DE)

(72) Inventors: Ulrich Lücking, Berlin (DE); Marcus Koppitz, Berlin (DE); Julien Lefranc, Berlin (DE); Lars Wortmann, Berlin (DE); Antje Margret Wengner, Berlin (DE); Gerhard Siemeister, Berlin (DE); Ulf Bömer, Glienicke (DE); Benjamin Bader, Berlin (DE); Philip Lienau, Berlin (DE); Hans Schick, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/067,830

(22) PCT Filed: Jan. 6, 2017

(86) PCT No.: PCT/EP2017/050243
§ 371 (c)(1),
(2) Date: Jul. 3, 2018

(87) PCT Pub. No.: WO2017/121684
PCT Pub. Date: Jul. 20, 2017

(65) Prior Publication Data
US 2019/0142812 A1 May 16, 2019

(30) Foreign Application Priority Data
Jan. 14, 2016 (EP) ..................... 16151209

(51) Int. Cl.
*A61K 31/4375* (2006.01)
*A61P 35/00* (2006.01)
*A61K 45/06* (2006.01)
*C07D 471/04* (2006.01)

(52) U.S. Cl.
CPC .......... *A61K 31/4375* (2013.01); *A61K 45/06* (2013.01); *A61P 35/00* (2018.01); *C07D 471/04* (2013.01)

(58) Field of Classification Search
CPC .................. A61K 31/4375; C07D 471/04
See application file for complete search history.

(56) References Cited

U.S. PATENT DOCUMENTS

| 9,549,932 B2* | 1/2017 | Wortmann ........... C07D 519/00 |
| 9,993,484 B2* | 6/2018 | Wortmann ........... A61K 31/541 |
| 2015/0158868 A1 | 6/2015 | Boyall et al. |
| 2018/0256591 A1 | 9/2018 | Wortmann |

FOREIGN PATENT DOCUMENTS

| WO | 2016/020320 | 2/2016 |
| WO | WO 2016/020320 | 2/2016 |
| WO | WO2018153969 A1 | 8/2018 |
| WO | WO2018153970 A1 | 8/2018 |
| WO | WO2018153971 A1 | 8/2018 |
| WO | WO2018153972 A1 | 8/2018 |
| WO | WO2018206547 A1 | 11/2018 |
| WO | WO2019025440 A1 | 2/2019 |
| WO | WO2019057852 A1 | 3/2019 |

OTHER PUBLICATIONS

International Search Report for PCT/EP2017/050243, dated Mar. 31, 2017, 2 pages.

(Continued)

*Primary Examiner* — Valerie Rodriguez-Garcia
(74) *Attorney, Agent, or Firm* — Morrison & Foerster LLP

(57) ABSTRACT

The present invention relates to 5-substituted 2-(morpholin-4-yl)-1,7-naphthyridine compounds of general formula (I) or (Ib), to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative disease as a sole agent or in combination with other active ingredients.

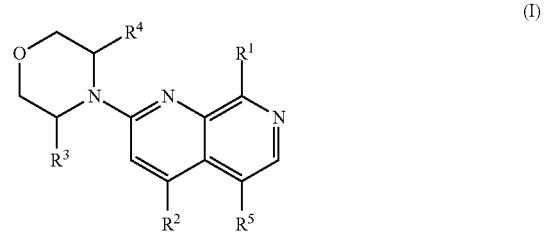

(I)

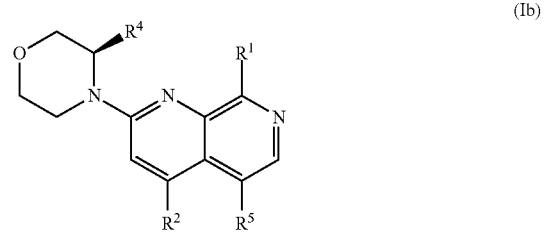

(Ib)

14 Claims, No Drawings

Specification includes a Sequence Listing.

(56) References Cited

OTHER PUBLICATIONS

W. Lumeras et al., "1,7-Naphthyridine 1-Oxides as Novel Potent and Selective Inhibitors of p38 Migogen Activated Protein Kinase", Journal of Medicinal Chemistry, (2011) vol. 54, pp. 7899-7910 (12 pages).
Lumeras et al., J. Med. Chem., 54, 7899-7910 (2011).
U.S. Appl. No. 15/974,536, filed May 8, 2018, for Wortmann et al. (U.S. Application is submitted herewith as US20180256591 A1.).
U.S. Appl. No. 16/488,033, filed Aug. 22, 2019, for Wengner et al. (U.S. Patent Application is not submitted herewith pursuant to the waiver of 37 C.F.R. § 1.98(a)(2)(iii) issued by the Office dated Sep. 21, 2004.).
U.S. Appl. No. 16/488,158, filed Aug. 22, 2019, for Cuthbertson et al. (U.S. Patent Application is not submitted herewith pursuant to the waiver of 37 C.F.R. § 1.98(a)(2)(iii) issued by the Office dated Sep. 21, 2004.).
U.S. Appl. No. 16/488,525, filed Aug. 23, 2019, for Wengner et al. (U.S. Patent Application is not submitted herewith pursuant to the waiver of 37 C.F.R. § 1.98(a)(2)(iii) issued by the Office dated Sep. 21, 2004.).

* cited by examiner

SEQUENCE LISTING

```
<160> NUMBER OF SEQ ID NOS: 4

<210> SEQ ID NO 1
<211> LENGTH: 8697
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon-optimized ATR including GST tag

<400> SEQUENCE: 1
atggcctccc ctatactagg ttattggaaa attaagggcc ttgtgcaacc cactcgactt       60
cttttggaat atcttgaaga aaaatatgaa gagcatttgt atgagcgcga tgaaggtgat      120
aaatggcgaa acaaaaagtt tgaattgggt ttggagtttc ccaatcttcc ttattatatt      180
gatggtgatg ttaaattaac acagtctatg gccatcatac gttatatagc tgacaagcac      240
aacatgttgg gtggttgtcc aaaagagcgt gcagagattt caatgcttga aggagcggtt      300
ttggatatta gatacggtgt ttcgagaatt gcatatagta aagactttga aactctcaaa      360
gttgattttc ttagcaagct acctgaaatg ctgaaaatgt tcgaagatcg tttatgtcat      420
aaaacatatt taaatggtga tcatgtaacc catcctgact tcatgttgta tgacgctctt      480
gatgttgttt tatacatgga cccaatgtgc ctggatgcgt tcccaaaatt agtttgtttt      540
aaaaaacgta ttgaagctat cccacaaatt gataagtact tgaaatccag caagtatata      600
gcatggcctt tgcagggctg gcaagccacg tttggtggtg gcgaccatcc tccaaaatcg      660
gatcagatca caagtttgta caaaaaagca ggctccgact atgacattcc aactacggag      720
aatttgtact tccaaggcga ctacaaggac gacgatgata gatgggtga acatggtttg      780 gagctcgcat ccatgattcc agccctgcgt gaactgggct ccgcaactcc agaggagtac      840
aacacggtgg tgcaaaaacc gcgtcagata ctgtgccagt tcatcgacag aatcctgacg      900
gatgtgaacg tggtggctgt cgagctcgtc aaaaagaccg attctcaacc aacgtccgtc      960
atgctgttgg actttatcca acacatcatg aaatcctccc cgctgatgtt cgttaacgtt     1020
tctggatccc acgaggctaa aggctcctgc atcgagttct caaactggat tatcaccaga     1080
ctgttgcgta ttgctgccac gcctagctgt cacttgctcc acaagaagat ctgcgaagta     1140
atatgctccc tgctgtttct gttcaagtcc aaatcacccg ctatatttgg agttctgaca     1200
aaggaattgt tgcagctgtt tgaggacctg gtatacttgc ataggcgtaa cgtgatgggt     1260
catgccgtcg agtggcctgt cgtcatgtct cgcttcctgt ctcagctcga cgaacatatg     1320
ggttatctcc agtccgcacc actccagttg atgtccatgc aaaacctgga gttcatagaa     1380
gtgacgttgc tcatggtgct gactagaatc attgctattg tgttcttccg ccgtcaagag     1440
ttgttgttgt ggcaaatcgg ctgcgtgttg ctggagtatg gctccccaaa gattaagagc     1500
```

```
ttggctatat cctttctgac agaactgttc cagctcggcg gtctgccggc ccagccggct    1560
tccacattct tctcctcatt cctggaactg ctgaagcacc tcgttgagat ggacacggac    1620
caactcaagc tgtacgaaga gcccttgtcc aaattgatta agacactgtt ccccttttgag   1680 gcagaggcgt acaggaacat cgagcccgta tatctgaaca tgctgctgga gaagctctgc    1740
gtgatgtttg aagatggagt actgatgcgc ctgaagtccg atctgctgaa ggctgctctg    1800
tgtcatctcc tgcaatactt cttgaaattc gttcctgccg gttacgagtc cgcttttgcaa  1860 gtacgcaagg tgtacgtacg taatatctgc aaggctctgc tggacgtgct cggtattgag    1920
gtagacgccg aatatctgtt gggcccattg tacgctgcgc tgaaaatgga gtcaatggaa    1980
atcattgagg aaatccagtg ccagacccag caagaaaatc tgagctccaa ctccgacgga    2040
atttctccaa agaggcgccg cttgagcagc tccctgaacc cttcaaagcg tgcaccaaag    2100
cagactgagg aaatcaagca cgtggacatg aaccaaaaga gcatactgtg gtccgcattg    2160
aagcagaaag ccgagtctctt gcagatttcc ctcgaatatt ccggcctgaa aaatcccgta    2220
attgaaatgc tcgagggcat cgccgtagtt ttgcaactga ccgctctgtg tactgtgcac    2280
tgctctcatc agaacatgaa ctgcaggaca ttcaaggact gccagcataa gtctaaaaag    2340
aagccctcag tcgtcatcac ttggatgtct ttggatttct ataccaaggt cctgaagtcc    2400
tgtcgtagcc tgctggagtc agtgcaaaag ttggatctgg aagccaccat cgataaagta    2460
gttaagattt acgacgccct catctacatg caagtcaact ccagcttcga ggaccatatc    2520
ctcgaagatc tgtgcggtat gctgagcctc ccttggatct acagccactc cgatgacgga    2580
tgtctgaagc tcaccacttt tgccgcaaat ttgttgaccc tgtcttgccg catatccgac    2640
tcatattcac ctcaagccca atcccgttgt gtattcctgc tcaccctgtt cccacgtcgt    2700
atttttctgg aatggagaac cgccgtatac aactgggctc tgcagtcctc ccacgaagtg    2760
ataagagcct catgtgtctc cggcttcttc atcttgctgc agcaacaaaa ctcttgtaat    2820
cgcgtcccga agatcctgat cgataaggtc aaggacgact ccgacattgt gaagaaagaa    2880
tttgccagca tcttgggcca gctggtctgc acactccacg gtatgttcta cctcacttcc    2940
agcttgacag aacccttctc cgagcatgga cacgtcgatc tgttttgtag gaatctgaaa    3000
gcaacttcac agcacgaatg ctcctcctcc cagctcaaag cctctgtctg caagcccttt    3060
ctgtttctgc tgaaaagaa atcccatca ccggttaaac tcgctttcat cgacaatctc    3120
caccacctgt gcaagcatct ggatttcagg gaggatgaga cagatgtgaa ggccgttctg    3180
ggtactctgc tcaacctgat ggaggaccca gacaaggacg tgagagtggc tttctccggt   3240
aacattaagc atatcctgga aagcctcgat agcgaggacg gatttatcaa agaattgttc    3300
gtcctgcgca tgaaggaagc ttacacgcat gcgcagatct ctcgtaataa cgagctgaag    3360
gacaccctga tattgacaac tggtgatatc ggaagagctg ccaagggcga tttggtgccg    3420
ttcgcgctgc tgcatttgct gcactgcctg ctgtctaagt ccgcttctgt ctctggcgct    3480
gcatacaccg aaattagggc gctggtggct gctaagtccg ttaaactcca gtctttcttc    3540
tcccagtaca aaaaacctat ttgccaattc ttggttgagt ccctgcactc ctcccagatg    3600
accgctctgc ccaacacacc ctgtcagaac gcagatgttc gcaaacagga cgttgcccac    3660
cagagggaga tggcactgaa tacactgtcc gagattgcta atgtgttcga cttttcccgat   3720 ctgaacaggt tcctgactcg tactctccag gtactgctgc ctgacctcgc cgctaaagcc    3780
tctccagctg cttcagccct gatccgtacc ctgggtaaac agctgaatgt caataggaga    3840
gaaatattga tcaacaactt caaatacatc ttttcacacc tggtatgctc ctgctctaag    3900
```

```
gacgagctgg agcgtgctct gcattatctg aagaacgaaa ccgaaataga actgggttcc   3960
ttgctccgcc aagatttcca aggtctgcat aacgagctgc tgctcaggat cggcgagcat   4020
taccagcaag tgttcaatgg tttgtcaatt ttggcgtcct tcgcctcctc cgacgaccca   4080
tatcagggcc ctagagacat catcagccca gaactgatgg ctgattatct gcaacctaag   4140
ttgctcggaa tcctcgcatt tttcaacatg caactgttgt caagctcagt cggcattgaa   4200
gataaaaga tggcgctcaa ctcactgatg agcctcatga agctgatggg cccaaagcat    4260
gtctcctccg tgagggttaa gatgatgacc actctgagga ctggcctgag gtttaaggac   4320
gatttccctg aactgtgctg ccgtgcctgg gattgtttcg tccgttgcct cgatcacgcc   4380
tgtctcggtt ccctgctgtc ccacgtcatc gtggcactct gccactgat tcacatacag    4440
cccaaggaaa cggccgcgat atttcactac ctcatcatcg aaaaccgtga cgcggtccag   4500
gatttcctgc atgagatcta cttcctgccc gaccacccgg aactgaagaa gatcaaggcc   4560
gttctgcagg aatatcgtaa agaaacctcc gagtccaccg atctgcagac caccctgcag   4620
ttgtcaatga aggcaatcca acatgagaac gtcgacgtca aatacacgc actgacctct    4680
ctgaaggaaa cactgtacaa gaaccaagag aagttgatca aatacgctac tgactcagag   4740
acagtagaac ccatcatctc acagctcgtg accgttctcc tcaagggttg ccaggacgct   4800
aactctcagg cgagattgct gtgtggcgag tgcctgggag aattgggcgc cattgacccc   4860
ggtcgcctgg acttcagcac aaccgagact caaggtaaag actttacctt cgtgaccgga   4920
gtcgaggatt cctccttcgc ttacggactg ctcatggaac tcactagagc ctacctggcc   4980
tatgctgaca actctcgcgc acaagattca gccgcttacg caatccaaga gctcctgtca   5040
atttacgact gccgtgagat ggaaacgaat ggtcccggtc accagctgtg gcgccgcttt   5100
ccagaacacg ttcgcgaaat cctggaaccc cacttgaaca ccagatacaa atccagccaa   5160
aagtctactg actggtccgg tgtgaagaag cctatttacc tgtccaaact gggcagcaat   5220
ttcgcagagt ggtccgctag ctgggcgggc tacctgatca ctaaagtgcg ccacgatctc   5280
gcaagcaaaa tcttcacttg ctgctccatt atgatgaagc atgacttcaa ggtgacaatt   5340
tatctgctcc cacacatcct ggtatacgtc ctgctgggct gtaaccagga agaccagcag   5400
gaggtatacg ctgagataat ggcagttttg aagcacgacg atcagcacac cattaacaca   5460
caggacattg cgtctgacct gtgtcaactg tccactcaaa ccgttttctc catgttggac   5520
catttgaccc agtgggcaag gcacaagttc caagccctca agcagagaa atgccctcac    5580
agcaagagca atcgcaacaa ggttgactcc atggtttcta cagttgatta tgaggactat   5640
caatcagtta cacgctttct ggatctgatt ccacaagaca ctctggctgt ggcatctttc   5700
cgctctaagg cttacactag ggccgtgatg cacttcgaat cctttatcac cgagaaaaaa   5760
cagaacatcc aggagcactt gggtttcctc caaaagctgt acgccgccat gcacgagccg   5820
gacggcgtcg cgggtgtttc cgcaattcgc aaagctgagc cctccctgaa ggaacagatt   5880
ctggagcacg agtcactggg tctgctccgc gatgccacgg cgtgttacga tcgcgcgatt   5940
cagttggagc cagaccaaat catccactat catggtgtag taaagtccat gctgggactg   6000
ggtcagctct ctacggttat cactcaggta acgagagtgc atgcgaaccg ctccgaatgg   6060
accgatgagc tcaatactta cagggtggag gcagcgtgga agctcagcca gtgggacttg   6120
gtcgaaaatt acctggctgc ggatggcaag tccacaacgt ggtccgtgcg cctcggccag   6180
ctgctgctgt cagctaaaaa gagggatatt acggctttct acgactctct gaaactcgtc   6240
```

```
cgcgccgaac aaattgttcc gctgagcgcc gcgtctttcg aacgcggaag ctaccagaga    6300
ggatatgagt acatcgttcg cctgcacatg ttgtgcgagc tggagcactc tatcaaaccc    6360
ttgttccaac actccccggg tgattcatcc aagaggact  ctctgaattg ggtcgctcgt    6420
ttggaaatga cccagaactc ctaccgcgcg aaggaaccta ttctggccct caggcgtgct    6480
ctgctgtcac tcaacaaacg cccggactac aatgagatgg tcggagaatg ttggctgcaa    6540
tcagctcgcg tggcgcgtaa agccggtcat catcaaactg cgtacaacgc tctgctgaac    6600
gccggcgaat cacgcttggc agaactctac gtagagcgcg caaaatggct gtggtccaag    6660
ggtgatgtgc accaggcgct catcgtcctg cagaagggag tggagctgtg tttccccgag    6720
aacgagacac caccggaagg aaagaacatg ctgatacatg aagggctat  gttgctggtg    6780
ggacgcttca tggaggaaac agcgaacttc gagtccaatg ctataatgaa gaagtacaaa    6840
gatgttacag cttgtctgcc cgaatgggag gacggtcact tctacttggc gaagtactat    6900
gataaattga tgcctatggt aaccgacaac aagatggaga agcaaggtga tctgatccgc    6960
tatatcgtgc tgcatttcgg tcgctcactg caatacggaa accagtttat ctaccaatcc    7020
atgccacgta tgttgaccct gtggctggat tacggtacca agcttacga  gtgggaaaaa    7080
gcgggcagga gcgacagagt gcagatgaga atgacctgg  gtaaaatcaa caaagtcata    7140
actgaacata ccaactacct cgcgccgtat cagtttctga ctgcttttcag ccaactcatc    7200
tcacgcatct gtcacagcca cgacgaggtt ttcgtggtcc tgatggaaat catcgcaaaa    7260
gtgttcctgg cctatcctca acaggccatg tggatgatga cggctgtgtc caagtcttca    7320
tacccccatgc gcgttaaccg ttgtaaggaa atcctgaaca aggctatcca catgaagaaa    7380
agcctggaga gtttgtcgg  tgacgctacg agactgaccg acaagttgct ggaattgtgc    7440
aacaagcctg tggatggaag ctccagcact ctgtctatga gcacgcactt caagatgctg    7500
aagaagctgg tagaagaggc cacgttttcc gaaatcctga taccctgca  gtccgtgatg    7560
atccctacct tgccttccat cctgggaacc cacgctaacc acgcctctca tgaacccttc    7620
cccggacact gggcctatat cgctggattt gacgatatgg tcgaaattct ggcatccctg    7680
cagaagccca aaaagatctc actgaagggt tccgacggta agttctacat aatgatgtgc    7740
aagcctaagg atgacctcag aaaggactgc cgtctgatgg agttcaactc cctgattaac    7800
aaatgtctca gaaaggacgc tgagagccgt cgcaggagc  tgcacattcg tacatacgca    7860
gtgatccctc tgaacgatga gtgtggcatc atagagtggg tcaataacac tgcgggactc    7920
cgcccgattc tgacaaaact ctacaaagag aagggtgtct atatgacagg taaagagttg    7980
cgccaatgta tgctccctaa atccgctgcc ctctccgaga agttgaaggt tttcagagaa    8040
ttcctcctgc caaggcaccc accaattttc cacgaatggt ttctgcgcac attccccgac    8100
cctacgtcct ggtattcttc ccgctccgcc tactgtcgtt caactgcagt aatgagcatg    8160
gttggttaca tcctcggtct gggcgaccgc cacggagaga acatcctgtt cgactccctg    8220
accggcgagt gcgtgcacgt ggatttcaat tgcttgttca ataagggtga aactttcgaa    8280
gtacctgaaa tagtgccttt ccgcctgaca cataacatgg tcaatggcat gggaccaatg    8340
ggcacggaag gactgttcag aagagcctgc gaggtcacca tgcgcctgat gcgcgatcag    8400
cgcgagccgc tgatgtcagt actcaagacg tttctgcatg accctctcgt ggagtggtcc    8460
aagcccgtca aggccatag  caaagcgcct ctgaacgaga ctggagaggt agtgaacgag    8520
aaggctaaaa cgcacgtcct cgatatagaa cagaggctgc aaggtgtgat caagacaaga    8580
aatcgtgtca cgggtctgcc tctgtccatt gaaggccacg tccactacct gatccaggag    8640
```
gccacagacg aaaatctgct ctgccaaatg tacctgggat ggacaccata catgtaa    8697

<210> SEQ ID NO 2
<211> LENGTH: 2493
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Codon-optimized ATRIP including STREP tag

<400> SEQUENCE: 2
atggccagct ggagccaccc tcagttcgaa aagagcgcgg cctcgagac aagtttgtac    60
aaaaaagcag gctccgatta tgacattcca acgaccgaaa atctgtactt tcagggcatg   120
gctggtacct ctgccccagg tagcaagagg agatcagaac tcctgcacc aaggcccggt   180
ccacctcccg gtactggaca tccaccctct aagcgcgcca gaggctttag cgctgccgcg   240
gcacctgatc ctgatgaccc ttttggtgct cacggtgact ttacagcaga cgatctggag   300
gagctcgaca ctttggcgtc ccaggcactg tcacaatgcc ccgcagccgc tcgcgacgtt   360
tcatccgacc acaaagtgca ccgtttgctc gacggaatgt ctaagaaccc ctccggaaaa   420
aacagggaaa ccgtccctat caaagacaac ttcgagctgg aggtgttgca agcccagtac   480
aaagagctga aggagaagat gaaggtgatg gaggaagagg tcctgatcaa gaccggcgag   540
atcaagattc tgcgcgattc cctgcaccag acggaaagcg tcctggaaga gcagaggcgt   600
tcccactttc tgctggagca ggaaaaaacg caggctctgt ccgacaagga aaggagttc    660
agcaagaagc tgcaaagctt gcaaagcgaa ctccagttca agatgctga atgaatgaa    720
ctccgtacaa agctgcagac cagcgagaga gctaataagc tcgctgcacc gagtgtgtca   780
cacgtatccc cgcgcaagaa tccgagtgta gttatcaagc tgaagcctg ttctccacaa   840
ttcggcaaaa catccttccc gacaaaggag tccttctccg ccaacatgtc tctgcctcac   900
ccttgtcaga ccgagtcagg ctacaaaccg ctggtcggta gagaggatag taagcccac    960
tctctgcgcg gagattccat aaagcaggag gaagcccaga gtccttcgt cgattcttgg   1020
cgtcaaagga gcaataccca gggttctatc ctcattaact gctcctgaa gcaacctttg   1080
atccccggct ctccctctc cctgtgtcat ctgctgtcca gctcttccga gtccccagct   1140
ggcacaccgc tgcaacctcc cggcttcggc tccactctcg cgggcatgtc aggactgagg   1200
acgaccggca gctatgacgg ttccttctct ctctccgcct gcgcgaagc gcagaacttg   1260
gcattcacgg gattgaacct ggttgctagg aacgagtgct cacgtgacgg agatccagcc   1320
gaaggtggac gcagagcctt ccttttgtgc caactgcccg gtgctgttca cttcttgcca   1380
ctggtgcagt tcttcatcgg tttgcactgt caagctctgc aggatctggc ggccgctaaa   1440
agatccggtg ctccgggtga ctcacccact catagctcat cgtctcttc cggtgtggaa   1500
acgaatccgg aggatagtgt atgcattctg gagggtttct cagttaccgc gctctccatt   1560
ctgcagcacc tggtgtgcca ttcaggcgcc gttgtcagtc tcctgctgtc tggagtcgga   1620
gcggactcag ccgcgggtga gggtaaccgc tccctcgtcc atcgcctgtc tgacggcgac   1680
atgaccagcg ctttgcgtgg agtcgcagat gaccaaggtc agcatcccct cttgaagatg   1740
ctgctgcatc tgttggcatt ttcctccgca gctactggtc acctccaagc cagcgtgttg   1800
acccagtgtc tcaaagtgct ggtcaaactg gcggagaaca caagttgcga cttcttgcct   1860
cgcttccaat gcgtgttcca agtactccct aagtgcttgt caccagaaac accgctgcca   1920

```
agtgtgctcc tggccgttga actgctgagt ctgctggctg accacgacca actggctccc    1980
cagctgtgca gtcacagtga aggttgtctg ctgctcctgc tctacatgta catcacgtca    2040
cgtcccgacc gtgtggcctt ggagactcaa tggttgcagc tggaacagga ggtcgtgtgg    2100
ctcctggcga aactgggagt gcagagtcca ctgccaccag ttacaggaag caactgtcag    2160
tgcaacgtag aggtggtgag agctctgaca gtcatgttgc atcgccaatg gctcactgta    2220
cgcagggcag gcggtccacc ccgtaccgat aacagcgcc gcaccgtaag atgtctgcgc    2280
gacactgttc tgctgctgca tggactgagc caaaaggaca aactgttcat gatgcactgc    2340
gtggaagtgc tgcaccagtt cgaccaagtc atgcccggcg tatccatgct catacgtgga    2400
ctgcccgatg taactgactg cgaggaagct gccctggacg atctgtgtgc tgcggaaact    2460
gacgtcgaag atcctgaggt tgaatgcggc taa                                 2493
```

<210> SEQ ID NO 3
<211> LENGTH: 2898
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Ala Ser Pro Ile Leu Gly Tyr Trp Lys Ile Lys Gly Leu Val Gln
1               5                   10                  15

Pro Thr Arg Leu Leu Leu Glu Tyr Leu Glu Glu Lys Tyr Glu Glu His
            20                  25                  30

Leu Tyr Glu Arg Asp Glu Gly Asp Lys Trp Arg Asn Lys Lys Phe Glu
        35                  40                  45

Leu Gly Leu Glu Phe Pro Asn Leu Pro Tyr Tyr Ile Asp Gly Asp Val
    50                  55                  60

Lys Leu Thr Gln Ser Met Ala Ile Ile Arg Tyr Ile Ala Asp Lys His
65                  70                  75                  80

Asn Met Leu Gly Gly Cys Pro Lys Glu Arg Ala Glu Ile Ser Met Leu
                85                  90                  95

Glu Gly Ala Val Leu Asp Ile Arg Tyr Gly Val Ser Arg Ile Ala Tyr
            100                 105                 110

Ser Lys Asp Phe Glu Thr Leu Lys Val Asp Phe Leu Ser Lys Leu Pro
        115                 120                 125

Glu Met Leu Lys Met Phe Glu Asp Arg Leu Cys His Lys Thr Tyr Leu
    130                 135                 140

Asn Gly Asp His Val Thr His Pro Asp Phe Met Leu Tyr Asp Ala Leu
145                 150                 155                 160

Asp Val Val Leu Tyr Met Asp Pro Met Cys Leu Asp Ala Phe Pro Lys
                165                 170                 175

Leu Val Cys Phe Lys Lys Arg Ile Glu Ala Ile Pro Gln Ile Asp Lys
            180                 185                 190

Tyr Leu Lys Ser Ser Lys Tyr Ile Ala Trp Pro Leu Gln Gly Trp Gln
        195                 200                 205

Ala Thr Phe Gly Gly Gly Asp His Pro Pro Lys Ser Asp Gln Ile Thr
    210                 215                 220

Ser Leu Tyr Lys Lys Ala Gly Ser Asp Tyr Asp Ile Pro Thr Thr Glu
225                 230                 235                 240

Asn Leu Tyr Phe Gln Gly Asp Tyr Lys Asp Asp Asp Lys Met Gly
                245                 250                 255
```

-continued

```
Glu His Gly Leu Glu Leu Ala Ser Met Ile Pro Ala Leu Arg Glu Leu
            260                 265                 270

Gly Ser Ala Thr Pro Glu Glu Tyr Asn Thr Val Val Gln Lys Pro Arg
            275                 280                 285

Gln Ile Leu Cys Gln Phe Ile Asp Arg Ile Leu Thr Asp Val Asn Val
            290                 295                 300

Val Ala Val Glu Leu Val Lys Lys Thr Asp Ser Gln Pro Thr Ser Val
305                 310                 315                 320

Met Leu Leu Asp Phe Ile Gln His Ile Met Lys Ser Ser Pro Leu Met
                    325                 330                 335

Phe Val Asn Val Ser Gly Ser His Glu Ala Lys Gly Ser Cys Ile Glu
            340                 345                 350

Phe Ser Asn Trp Ile Ile Thr Arg Leu Leu Arg Ile Ala Ala Thr Pro
            355                 360                 365

Ser Cys His Leu Leu His Lys Lys Ile Cys Glu Val Ile Cys Ser Leu
    370                 375                 380

Leu Phe Leu Phe Lys Ser Lys Ser Pro Ala Ile Phe Gly Val Leu Thr
385                 390                 395                 400

Lys Glu Leu Leu Gln Leu Phe Glu Asp Leu Val Tyr Leu His Arg Arg
                    405                 410                 415

Asn Val Met Gly His Ala Val Glu Trp Pro Val Val Met Ser Arg Phe
            420                 425                 430

Leu Ser Gln Leu Asp Glu His Met Gly Tyr Leu Gln Ser Ala Pro Leu
            435                 440                 445

Gln Leu Met Ser Met Gln Asn Leu Glu Phe Ile Glu Val Thr Leu Leu
            450                 455                 460

Met Val Leu Thr Arg Ile Ile Ala Ile Val Phe Phe Arg Arg Gln Glu
465                 470                 475                 480

Leu Leu Leu Trp Gln Ile Gly Cys Val Leu Leu Glu Tyr Gly Ser Pro
                    485                 490                 495

Lys Ile Lys Ser Leu Ala Ile Ser Phe Leu Thr Glu Leu Phe Gln Leu
            500                 505                 510

Gly Gly Leu Pro Ala Gln Pro Ala Ser Thr Phe Phe Ser Ser Phe Leu
            515                 520                 525

Glu Leu Leu Lys His Leu Val Glu Met Asp Thr Asp Gln Leu Lys Leu
            530                 535                 540

Tyr Glu Glu Pro Leu Ser Lys Leu Ile Lys Thr Leu Phe Pro Phe Glu
545                 550                 555                 560

Ala Glu Ala Tyr Arg Asn Ile Glu Pro Val Tyr Leu Asn Met Leu Leu
                    565                 570                 575

Glu Lys Leu Cys Val Met Phe Glu Asp Gly Val Leu Met Arg Leu Lys
            580                 585                 590

Ser Asp Leu Leu Lys Ala Ala Leu Cys His Leu Leu Gln Tyr Phe Leu
            595                 600                 605

Lys Phe Val Pro Ala Gly Tyr Glu Ser Ala Leu Gln Val Arg Lys Val
            610                 615                 620

Tyr Val Arg Asn Ile Cys Lys Ala Leu Leu Asp Val Leu Gly Ile Glu
625                 630                 635                 640

Val Asp Ala Glu Tyr Leu Leu Gly Pro Leu Tyr Ala Ala Leu Lys Met
                    645                 650                 655

Glu Ser Met Glu Ile Ile Glu Gly Ile Gln Cys Gln Thr Gln Gln Glu
            660                 665                 670
```

```
Asn Leu Ser Ser Asn Ser Asp Gly Ile Ser Pro Lys Arg Arg Leu
            675                 680                 685

Ser Ser Ser Leu Asn Pro Ser Lys Arg Ala Pro Lys Gln Thr Glu Glu
    690                 695                 700

Ile Lys His Val Asp Met Asn Gln Lys Ser Ile Leu Trp Ser Ala Leu
705                 710                 715                 720

Lys Gln Lys Ala Glu Ser Leu Gln Ile Ser Leu Glu Tyr Ser Gly Leu
                725                 730                 735

Lys Asn Pro Val Ile Glu Met Leu Glu Gly Ile Ala Val Val Leu Gln
                740                 745                 750

Leu Thr Ala Leu Cys Thr Val His Cys Ser His Gln Asn Met Asn Cys
                755                 760                 765

Arg Thr Phe Lys Asp Cys Gln His Lys Ser Lys Lys Pro Ser Val
    770                 775                 780

Val Ile Thr Trp Met Ser Leu Asp Phe Tyr Thr Lys Val Leu Lys Ser
785                 790                 795                 800

Cys Arg Ser Leu Leu Glu Ser Val Gln Lys Leu Asp Leu Glu Ala Thr
                805                 810                 815

Ile Asp Lys Val Val Lys Ile Tyr Asp Ala Leu Ile Tyr Met Gln Val
                820                 825                 830

Asn Ser Ser Phe Glu Asp His Ile Leu Glu Asp Leu Cys Gly Met Leu
                835                 840                 845

Ser Leu Pro Trp Ile Tyr Ser His Ser Asp Asp Gly Cys Leu Lys Leu
                850                 855                 860

Thr Thr Phe Ala Ala Asn Leu Leu Thr Leu Ser Cys Arg Ile Ser Asp
865                 870                 875                 880

Ser Tyr Ser Pro Gln Ala Gln Ser Arg Cys Val Phe Leu Leu Thr Leu
                885                 890                 895

Phe Pro Arg Arg Ile Phe Leu Glu Trp Arg Thr Ala Val Tyr Asn Trp
                900                 905                 910

Ala Leu Gln Ser Ser His Glu Val Ile Arg Ala Ser Cys Val Ser Gly
                915                 920                 925

Phe Phe Ile Leu Leu Gln Gln Gln Asn Ser Cys Asn Arg Val Pro Lys
                930                 935                 940

Ile Leu Ile Asp Lys Val Lys Asp Ser Asp Ser Ile Val Lys Lys Glu
945                 950                 955                 960

Phe Ala Ser Ile Leu Gly Gln Leu Val Cys Thr Leu His Gly Met Phe
                965                 970                 975

Tyr Leu Thr Ser Ser Leu Thr Glu Pro Phe Ser Glu His Gly His Val
                980                 985                 990

Asp Leu Phe Cys Arg Asn Leu Lys Ala Thr Ser Gln His Glu Cys Ser
                995                 1000                1005

Ser Ser Gln Leu Lys Ala Ser Val Cys Lys Pro Phe Leu Phe Leu
    1010                1015                1020

Leu Lys Lys Lys Ile Pro Ser Pro Val Leu Ala Phe Ile Asp
    1025                1030                1035

Asn Leu His His Leu Cys Lys His Leu Asp Phe Arg Glu Asp Glu
    1040                1045                1050

Thr Asp Val Lys Ala Val Leu Gly Thr Leu Leu Asn Leu Met Glu
    1055                1060                1065

Asp Pro Asp Lys Asp Val Arg Val Ala Phe Ser Gly Asn Ile Lys
    1070                1075                1080

His Ile Leu Glu Ser Leu Asp Ser Glu Asp Gly Phe Ile Lys Glu
```

```
                1085                1090                1095
Leu Phe Val Leu Arg Met Lys Glu Ala Tyr Thr His Ala Gln Ile
                1100                1105                1110
Ser Arg Asn Asn Glu Leu Lys Asp Thr Leu Ile Leu Thr Thr Gly
                1115                1120                1125
Asp Ile Gly Arg Ala Ala Lys Gly Asp Leu Val Pro Phe Ala Leu
                1130                1135                1140
Leu His Leu Leu His Cys Leu Leu Ser Lys Ser Ala Ser Val Ser
                1145                1150                1155
Gly Ala Ala Tyr Thr Glu Ile Arg Ala Leu Val Ala Ala Lys Ser
                1160                1165                1170
Val Lys Leu Gln Ser Phe Phe Ser Gln Tyr Lys Lys Pro Ile Cys
                1175                1180                1185
Gln Phe Leu Val Glu Ser Leu His Ser Ser Gln Met Thr Ala Leu
                1190                1195                1200
Pro Asn Thr Pro Cys Gln Asn Ala Asp Val Arg Lys Gln Asp Val
                1205                1210                1215
Ala His Gln Arg Glu Met Ala Leu Asn Thr Leu Ser Glu Ile Ala
                1220                1225                1230
Asn Val Phe Asp Phe Pro Asp Leu Asn Arg Phe Leu Thr Arg Thr
                1235                1240                1245
Leu Gln Val Leu Leu Pro Asp Leu Ala Ala Lys Ala Ser Pro Ala
                1250                1255                1260
Ala Ser Ala Leu Ile Arg Thr Leu Gly Lys Gln Leu Asn Val Asn
                1265                1270                1275
Arg Arg Glu Ile Leu Ile Asn Asn Phe Lys Tyr Ile Phe Ser His
                1280                1285                1290
Leu Val Cys Ser Cys Ser Lys Asp Glu Leu Glu Arg Ala Leu His
                1295                1300                1305
Tyr Leu Lys Asn Glu Thr Glu Ile Glu Leu Gly Ser Leu Leu Arg
                1310                1315                1320
Gln Asp Phe Gln Gly Leu His Asn Glu Leu Leu Leu Arg Ile Gly
                1325                1330                1335
Glu His Tyr Gln Gln Val Phe Asn Gly Leu Ser Ile Leu Ala Ser
                1340                1345                1350
Phe Ala Ser Ser Asp Asp Pro Tyr Gln Gly Pro Arg Asp Ile Ile
                1355                1360                1365
Ser Pro Glu Leu Met Ala Asp Tyr Leu Gln Pro Lys Leu Leu Gly
                1370                1375                1380
Ile Leu Ala Phe Phe Asn Met Gln Leu Leu Ser Ser Val Gly
                1385                1390                1395
Ile Glu Asp Lys Lys Met Ala Leu Asn Ser Leu Met Ser Leu Met
                1400                1405                1410
Lys Leu Met Gly Pro Lys His Val Ser Ser Val Arg Val Lys Met
                1415                1420                1425
Met Thr Thr Leu Arg Thr Gly Leu Arg Phe Lys Asp Asp Phe Pro
                1430                1435                1440
Glu Leu Cys Cys Arg Ala Trp Asp Cys Phe Val Arg Cys Leu Asp
                1445                1450                1455
His Ala Cys Leu Gly Ser Leu Leu Ser His Val Ile Val Ala Leu
                1460                1465                1470
Leu Pro Leu Ile His Ile Gln Pro Lys Glu Thr Ala Ala Ile Phe
                1475                1480                1485
```

-continued

His Tyr Leu Ile Ile Glu Asn Arg Asp Ala Val Gln Asp Phe Leu
1490                1495                1500

His Glu Ile Tyr Phe Leu Pro Asp His Pro Glu Leu Lys Lys Ile
1505                1510                1515

Lys Ala Val Leu Gln Glu Tyr Arg Lys Glu Thr Ser Glu Ser Thr
1520                1525                1530

Asp Leu Gln Thr Thr Leu Gln Leu Ser Met Lys Ala Ile Gln His
1535                1540                1545

Glu Asn Val Asp Val Arg Ile His Ala Leu Thr Ser Leu Lys Glu
1550                1555                1560

Thr Leu Tyr Lys Asn Gln Glu Lys Leu Ile Lys Tyr Ala Thr Asp
1565                1570                1575

Ser Glu Thr Val Glu Pro Ile Ile Ser Gln Leu Val Thr Val Leu
1580                1585                1590

Leu Lys Gly Cys Gln Asp Ala Asn Ser Gln Ala Arg Leu Leu Cys
1595                1600                1605

Gly Glu Cys Leu Gly Glu Leu Gly Ala Ile Asp Pro Gly Arg Leu
1610                1615                1620

Asp Phe Ser Thr Thr Glu Thr Gln Gly Lys Asp Phe Thr Phe Val
1625                1630                1635

Thr Gly Val Glu Asp Ser Ser Phe Ala Tyr Gly Leu Leu Met Glu
1640                1645                1650

Leu Thr Arg Ala Tyr Leu Ala Tyr Ala Asp Asn Ser Arg Ala Gln
1655                1660                1665

Asp Ser Ala Ala Tyr Ala Ile Gln Glu Leu Leu Ser Ile Tyr Asp
1670                1675                1680

Cys Arg Glu Met Glu Thr Asn Gly Pro Gly His Gln Leu Trp Arg
1685                1690                1695

Arg Phe Pro Glu His Val Arg Glu Ile Leu Glu Pro His Leu Asn
1700                1705                1710

Thr Arg Tyr Lys Ser Ser Gln Lys Ser Thr Asp Trp Ser Gly Val
1715                1720                1725

Lys Lys Pro Ile Tyr Leu Ser Lys Leu Gly Ser Asn Phe Ala Glu
1730                1735                1740

Trp Ser Ala Ser Trp Ala Gly Tyr Leu Ile Thr Lys Val Arg His
1745                1750                1755

Asp Leu Ala Ser Lys Ile Phe Thr Cys Cys Ser Ile Met Met Lys
1760                1765                1770

His Asp Phe Lys Val Thr Ile Tyr Leu Leu Pro His Ile Leu Val
1775                1780                1785

Tyr Val Leu Leu Gly Cys Asn Gln Glu Asp Gln Gln Glu Val Tyr
1790                1795                1800

Ala Glu Ile Met Ala Val Leu Lys His Asp Asp Gln His Thr Ile
1805                1810                1815

Asn Thr Gln Asp Ile Ala Ser Asp Leu Cys Gln Leu Ser Thr Gln
1820                1825                1830

Thr Val Phe Ser Met Leu Asp His Leu Thr Gln Trp Ala Arg His
1835                1840                1845

Lys Phe Gln Ala Leu Lys Ala Glu Lys Cys Pro His Ser Lys Ser
1850                1855                1860

Asn Arg Asn Lys Val Asp Ser Met Val Ser Thr Val Asp Tyr Glu
1865                1870                1875

```
Asp Tyr Gln Ser Val Thr Arg Phe Leu Asp Leu Ile Pro Gln Asp
    1880                1885                1890

Thr Leu Ala Val Ala Ser Phe Arg Ser Lys Ala Tyr Thr Arg Ala
    1895                1900                1905

Val Met His Phe Glu Ser Phe Ile Thr Glu Lys Lys Gln Asn Ile
    1910                1915                1920

Gln Glu His Leu Gly Phe Leu Gln Lys Leu Tyr Ala Ala Met His
    1925                1930                1935

Glu Pro Asp Gly Val Ala Gly Val Ser Ala Ile Arg Lys Ala Glu
    1940                1945                1950

Pro Ser Leu Lys Glu Gln Ile Leu Glu His Glu Ser Leu Gly Leu
    1955                1960                1965

Leu Arg Asp Ala Thr Ala Cys Tyr Asp Arg Ala Ile Gln Leu Glu
    1970                1975                1980

Pro Asp Gln Ile Ile His Tyr His Gly Val Val Lys Ser Met Leu
    1985                1990                1995

Gly Leu Gly Gln Leu Ser Thr Val Ile Thr Gln Val Asn Gly Val
    2000                2005                2010

His Ala Asn Arg Ser Glu Trp Thr Asp Glu Leu Asn Thr Tyr Arg
    2015                2020                2025

Val Glu Ala Ala Trp Lys Leu Ser Gln Trp Asp Leu Val Glu Asn
    2030                2035                2040

Tyr Leu Ala Ala Asp Gly Lys Ser Thr Thr Trp Ser Val Arg Leu
    2045                2050                2055

Gly Gln Leu Leu Leu Ser Ala Lys Lys Arg Asp Ile Thr Ala Phe
    2060                2065                2070

Tyr Asp Ser Leu Lys Leu Val Arg Ala Glu Gln Ile Val Pro Leu
    2075                2080                2085

Ser Ala Ala Ser Phe Glu Arg Gly Ser Tyr Gln Arg Gly Tyr Glu
    2090                2095                2100

Tyr Ile Val Arg Leu His Met Leu Cys Glu Leu Glu His Ser Ile
    2105                2110                2115

Lys Pro Leu Phe Gln His Ser Pro Gly Asp Ser Ser Gln Glu Asp
    2120                2125                2130

Ser Leu Asn Trp Val Ala Arg Leu Glu Met Thr Gln Asn Ser Tyr
    2135                2140                2145

Arg Ala Lys Glu Pro Ile Leu Ala Leu Arg Arg Ala Leu Leu Ser
    2150                2155                2160

Leu Asn Lys Arg Pro Asp Tyr Asn Glu Met Val Gly Glu Cys Trp
    2165                2170                2175

Leu Gln Ser Ala Arg Val Ala Arg Lys Ala Gly His His Gln Thr
    2180                2185                2190

Ala Tyr Asn Ala Leu Leu Asn Ala Gly Glu Ser Arg Leu Ala Glu
    2195                2200                2205

Leu Tyr Val Glu Arg Ala Lys Trp Leu Trp Ser Lys Gly Asp Val
    2210                2215                2220

His Gln Ala Leu Ile Val Leu Gln Lys Gly Val Glu Leu Cys Phe
    2225                2230                2235

Pro Glu Asn Glu Thr Pro Pro Glu Gly Lys Asn Met Leu Ile His
    2240                2245                2250

Gly Arg Ala Met Leu Leu Val Gly Arg Phe Met Glu Glu Thr Ala
    2255                2260                2265

Asn Phe Glu Ser Asn Ala Ile Met Lys Lys Tyr Lys Asp Val Thr
```

```
              2270                2275                 2280

Ala Cys Leu Pro Glu Trp Glu Asp Gly His Phe Tyr Leu Ala Lys
    2285            2290                2295

Tyr Tyr Asp Lys Leu Met Pro Met Val Thr Asp Asn Lys Met Glu
    2300            2305                2310

Lys Gln Gly Asp Leu Ile Arg Tyr Ile Val Leu His Phe Gly Arg
    2315            2320                2325

Ser Leu Gln Tyr Gly Asn Gln Phe Ile Tyr Gln Ser Met Pro Arg
    2330            2335                2340

Met Leu Thr Leu Trp Leu Asp Tyr Gly Thr Lys Ala Tyr Glu Trp
    2345            2350                2355

Glu Lys Ala Gly Arg Ser Asp Arg Val Gln Met Arg Asn Asp Leu
    2360            2365                2370

Gly Lys Ile Asn Lys Val Ile Thr Glu His Thr Asn Tyr Leu Ala
    2375            2380                2385

Pro Tyr Gln Phe Leu Thr Ala Phe Ser Gln Leu Ile Ser Arg Ile
    2390            2395                2400

Cys His Ser His Asp Glu Val Phe Val Val Leu Met Glu Ile Ile
    2405            2410                2415

Ala Lys Val Phe Leu Ala Tyr Pro Gln Gln Ala Met Trp Met Met
    2420            2425                2430

Thr Ala Val Ser Lys Ser Ser Tyr Pro Met Arg Val Asn Arg Cys
    2435            2440                2445

Lys Glu Ile Leu Asn Lys Ala Ile His Met Lys Lys Ser Leu Glu
    2450            2455                2460

Lys Phe Val Gly Asp Ala Thr Arg Leu Thr Asp Lys Leu Leu Glu
    2465            2470                2475

Leu Cys Asn Lys Pro Val Asp Gly Ser Ser Thr Leu Ser Met
    2480            2485                2490

Ser Thr His Phe Lys Met Leu Lys Lys Leu Val Glu Glu Ala Thr
    2495            2500                2505

Phe Ser Glu Ile Leu Ile Pro Leu Gln Ser Val Met Ile Pro Thr
    2510            2515                2520

Leu Pro Ser Ile Leu Gly Thr His Ala Asn His Ala Ser His Glu
    2525            2530                2535

Pro Phe Pro Gly His Trp Ala Tyr Ile Ala Gly Phe Asp Asp Met
    2540            2545                2550

Val Glu Ile Leu Ala Ser Leu Gln Lys Pro Lys Lys Ile Ser Leu
    2555            2560                2565

Lys Gly Ser Asp Gly Lys Phe Tyr Ile Met Met Cys Lys Pro Lys
    2570            2575                2580

Asp Asp Leu Arg Lys Asp Cys Arg Leu Met Glu Phe Asn Ser Leu
    2585            2590                2595

Ile Asn Lys Cys Leu Arg Lys Asp Ala Glu Ser Arg Arg Arg Glu
    2600            2605                2610

Leu His Ile Arg Thr Tyr Ala Val Ile Pro Leu Asn Asp Glu Cys
    2615            2620                2625

Gly Ile Ile Glu Trp Val Asn Asn Thr Ala Gly Leu Arg Pro Ile
    2630            2635                2640

Leu Thr Lys Leu Tyr Lys Glu Lys Gly Val Tyr Met Thr Gly Lys
    2645            2650                2655

Glu Leu Arg Gln Cys Met Leu Pro Lys Ser Ala Ala Leu Ser Glu
    2660            2665                2670
```

```
Lys Leu Lys Val Phe Arg Glu Phe Leu Pro Arg His Pro Pro
    2675                2680                2685

Ile Phe His Glu Trp Phe Leu Arg Thr Phe Pro Asp Pro Thr Ser
    2690                2695                2700

Trp Tyr Ser Ser Arg Ser Ala Tyr Cys Arg Ser Thr Ala Val Met
    2705                2710                2715

Ser Met Val Gly Tyr Ile Leu Gly Leu Gly Asp Arg His Gly Glu
    2720                2725                2730

Asn Ile Leu Phe Asp Ser Leu Thr Gly Glu Cys Val His Val Asp
    2735                2740                2745

Phe Asn Cys Leu Phe Asn Lys Gly Glu Thr Phe Glu Val Pro Glu
    2750                2755                2760

Ile Val Pro Phe Arg Leu Thr His Asn Met Val Asn Gly Met Gly
    2765                2770                2775

Pro Met Gly Thr Glu Gly Leu Phe Arg Arg Ala Cys Glu Val Thr
    2780                2785                2790

Met Arg Leu Met Arg Asp Gln Arg Glu Pro Leu Met Ser Val Leu
    2795                2800                2805

Lys Thr Phe Leu His Asp Pro Leu Val Glu Trp Ser Lys Pro Val
    2810                2815                2820

Lys Gly His Ser Lys Ala Pro Leu Asn Glu Thr Gly Glu Val Val
    2825                2830                2835

Asn Glu Lys Ala Lys Thr His Val Leu Asp Ile Glu Gln Arg Leu
    2840                2845                2850

Gln Gly Val Ile Lys Thr Arg Asn Arg Val Thr Gly Leu Pro Leu
    2855                2860                2865

Ser Ile Glu Gly His Val His Tyr Leu Ile Gln Glu Ala Thr Asp
    2870                2875                2880

Glu Asn Leu Leu Cys Gln Met Tyr Leu Gly Trp Thr Pro Tyr Met
    2885                2890                2895

<210> SEQ ID NO 4
<211> LENGTH: 830
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Ser Trp Ser His Pro Gln Phe Glu Lys Ser Ala Gly Leu Glu
1               5                   10                  15

Thr Ser Leu Tyr Lys Lys Ala Gly Ser Asp Tyr Asp Ile Pro Thr Thr
                20                  25                  30

Glu Asn Leu Tyr Phe Gln Gly Met Ala Gly Thr Ser Ala Pro Gly Ser
            35                  40                  45

Lys Arg Arg Ser Glu Pro Pro Ala Pro Arg Gly Pro Pro Gly
    50                  55                  60

Thr Gly His Pro Pro Ser Lys Arg Ala Arg Gly Phe Ser Ala Ala Ala
65                  70                  75                  80

Ala Pro Asp Pro Asp Asp Pro Phe Gly Ala His Gly Asp Phe Thr Ala
                85                  90                  95

Asp Asp Leu Glu Glu Leu Asp Thr Leu Ala Ser Gln Ala Leu Ser Gln
            100                 105                 110

Cys Pro Ala Ala Ala Arg Asp Val Ser Ser Asp His Lys Val His Arg
```

-continued

```
            115                 120                 125
Leu Leu Asp Gly Met Ser Lys Asn Pro Ser Gly Lys Asn Arg Glu Thr
130                 135                 140

Val Pro Ile Lys Asp Asn Phe Glu Leu Glu Val Leu Gln Ala Gln Tyr
145                 150                 155                 160

Lys Glu Leu Lys Glu Lys Met Lys Val Met Glu Glu Val Leu Ile
                    165                 170                 175

Lys Asn Gly Glu Ile Lys Ile Leu Arg Asp Ser Leu His Gln Thr Glu
                180                 185                 190

Ser Val Leu Glu Glu Gln Arg Arg Ser His Phe Leu Glu Gln Glu
        195                 200                 205

Lys Thr Gln Ala Leu Ser Asp Lys Glu Lys Glu Phe Ser Lys Lys Leu
210                 215                 220

Gln Ser Leu Gln Ser Glu Leu Gln Phe Lys Asp Ala Glu Met Asn Glu
225                 230                 235                 240

Leu Arg Thr Lys Leu Gln Thr Ser Glu Arg Ala Asn Lys Leu Ala Ala
                245                 250                 255

Pro Ser Val Ser His Val Ser Pro Arg Lys Asn Pro Ser Val Val Ile
                260                 265                 270

Lys Pro Glu Ala Cys Ser Pro Gln Phe Gly Lys Thr Ser Phe Pro Thr
                275                 280                 285

Lys Glu Ser Phe Ser Ala Asn Met Ser Leu Pro His Pro Cys Gln Thr
                290                 295                 300

Glu Ser Gly Tyr Lys Pro Leu Val Gly Arg Glu Asp Ser Lys Pro His
305                 310                 315                 320

Ser Leu Arg Gly Asp Ser Ile Lys Gln Glu Glu Ala Gln Lys Ser Phe
                325                 330                 335

Val Asp Ser Trp Arg Gln Arg Ser Asn Thr Gln Gly Ser Ile Leu Ile
                340                 345                 350

Asn Leu Leu Leu Lys Gln Pro Leu Ile Pro Gly Ser Ser Leu Ser Leu
                355                 360                 365

Cys His Leu Leu Ser Ser Ser Glu Ser Pro Ala Gly Thr Pro Leu
                370                 375                 380

Gln Pro Pro Gly Phe Gly Ser Thr Leu Ala Gly Met Ser Gly Leu Arg
385                 390                 395                 400

Thr Thr Gly Ser Tyr Asp Gly Ser Phe Ser Leu Ser Ala Leu Arg Glu
                405                 410                 415

Ala Gln Asn Leu Ala Phe Thr Gly Leu Asn Leu Val Ala Arg Asn Glu
                420                 425                 430

Cys Ser Arg Asp Gly Asp Pro Ala Glu Gly Gly Arg Arg Ala Phe Pro
                435                 440                 445

Leu Cys Gln Leu Pro Gly Ala Val His Phe Leu Pro Leu Val Gln Phe
450                 455                 460

Phe Ile Gly Leu His Cys Gln Ala Leu Gln Asp Leu Ala Ala Lys
465                 470                 475                 480

Arg Ser Gly Ala Pro Gly Asp Ser Pro Thr His Ser Ser Cys Val Ser
                485                 490                 495

Ser Gly Val Glu Thr Asn Pro Glu Asp Ser Val Cys Ile Leu Glu Gly
                500                 505                 510

Phe Ser Val Thr Ala Leu Ser Ile Leu Gln His Leu Val Cys His Ser
                515                 520                 525

Gly Ala Val Val Ser Leu Leu Leu Ser Gly Val Gly Ala Asp Ser Ala
530                 535                 540
```

```
Ala Gly Glu Gly Asn Arg Ser Leu Val His Arg Leu Ser Asp Gly Asp
545                 550                 555                 560

Met Thr Ser Ala Leu Arg Gly Val Ala Asp Asp Gln Gly Gln His Pro
            565                 570                 575

Leu Leu Lys Met Leu Leu His Leu Leu Ala Phe Ser Ser Ala Ala Thr
                580                 585                 590

Gly His Leu Gln Ala Ser Val Leu Thr Gln Cys Leu Lys Val Leu Val
        595                 600                 605

Lys Leu Ala Glu Asn Thr Ser Cys Asp Phe Leu Pro Arg Phe Gln Cys
    610                 615                 620

Val Phe Gln Val Leu Pro Lys Cys Leu Ser Pro Glu Thr Pro Leu Pro
625                 630                 635                 640

Ser Val Leu Leu Ala Val Glu Leu Leu Ser Leu Leu Ala Asp His Asp
                645                 650                 655

Gln Leu Ala Pro Gln Leu Cys Ser His Ser Glu Gly Cys Leu Leu Leu
            660                 665                 670

Leu Leu Tyr Met Tyr Ile Thr Ser Arg Pro Asp Arg Val Ala Leu Glu
        675                 680                 685

Thr Gln Trp Leu Gln Leu Glu Gln Glu Val Val Trp Leu Leu Ala Lys
    690                 695                 700

Leu Gly Val Gln Ser Pro Leu Pro Pro Val Thr Gly Ser Asn Cys Gln
705                 710                 715                 720

Cys Asn Val Glu Val Val Arg Ala Leu Thr Val Met Leu His Arg Gln
                725                 730                 735

Trp Leu Thr Val Arg Arg Ala Gly Gly Pro Pro Arg Thr Asp Gln Gln
            740                 745                 750

Arg Arg Thr Val Arg Cys Leu Arg Asp Thr Val Leu Leu Leu His Gly
        755                 760                 765

Leu Ser Gln Lys Asp Lys Leu Phe Met Met His Cys Val Glu Val Leu
    770                 775                 780

His Gln Phe Asp Gln Val Met Pro Gly Val Ser Met Leu Ile Arg Gly
785                 790                 795                 800

Leu Pro Asp Val Thr Asp Cys Glu Glu Ala Ala Leu Asp Asp Leu Cys
                805                 810                 815

Ala Ala Glu Thr Asp Val Glu Asp Pro Glu Val Glu Cys Gly
            820                 825                 830
```

5-SUBSTITUTED 2-(MORPHOLIN-4-YL)-1,7-NAPHTHYRIDINES

This application is the U.S. national phase of International Application No. PCT/EP2017/050243 filed 6 Jan. 2017, which designated the U.S. and claims priority to EP Patent Application No. 16151209.0 filed 14 Jan. 2016, the entire contents of each of which are hereby incorporated by reference.

SEQUENCE LISTING

The instant application contains a Sequence Listing which has been submitted electronically in ASCII format and is hereby incorporated by reference in, its entirety. Said ASCII copy, created on Nov. 29, 2018, is named 6487-0213_SL.txt, and is 48,172 bytes in size.

FIELD OF APPLICATION OF THE INVENTION

The invention relates to substituted 5-alkyl- or 5-alkoxy-2-(morpholin-4-yl)-1,7-naphthyridine compounds, a process for their production and the use thereof.

BACKGROUND OF THE INVENTION

The integrity of the genome of eukaryotic cells is secured by complex signaling pathways, referred to as the DNA damage response (DDR), and multiple DNA repair mechanisms. Upon recognizing DNA damage activation of the DDR pathways results in cell cycle arrest, suppression of general translation, induction of DNA repair, and, finally, in cell survival or cell death. Proteins that directly recognize aberrant DNA structures, such as the MRE11-Rad50-Nbs1 complex recognizing DNA double strand breaks by binding to double-stranded DNA ends, or RPA (replication protein A) binding to single stranded DNA, recruit and activate the most upstream kinases of the DDR pathway, ATM (ataxia-telangiectasia mutated), ATR (ATM- and Rad3-related, UniProtKB/Swiss-Prot Q13535), and DNA-PKcs (DNA-dependent protein kinase). Whereas ATM is primarily activated by DNA double strand breaks, and DNA-PKcs is mainly involved in non-homologous end joining process of DNA repair, ATR responds to a broad spectrum of DNA damage, including double-strand breaks and lesions derived from interference with DNA replication. Major components of downstream signaling of ATM include Chk2 and p53, whereas ATR signaling involves Chk1 and cdc25. Knockout of the ATR gene in mice is embryonically lethal and ATR knockout cells develop chromosome breaks and undergo apoptosis [E. J. Brown, D. Baltimore: ATR disruption leads to chromosomal fragmentation and early embryonic lethality. Genes Dev. 14, 397-402, 2000]. In contrast, ATM is not essential for cell survival although ATM knockout cells are hypersensitive to ionizing radiation and agents which cause DNA double-strand breaks.

ATR, which forms a complex with ATRIP (ATR-interacting protein, UniProtKB/Swiss-Prot Q8WXE1) is mainly activated by long stretches of single-stranded DNA which are generated by the continuing DNA unwinding activity of helicases upon stalled replication. This replication stress with stalled replication forks may be induced by ultraviolet light, certain chemotherapeutic drugs, hydroxyurea, or aberrant oncogenic signaling resulting in increased replication initiation or origin firing. Activation of ATR results in inhibition of the cell cycle in S or G2 phase via the Chk1-cdc25 pathway and in suppression of late origin firing. The cell gains time to resolve the replication stress and, eventually, to restart replication after the source of stress has been removed. As the ATR pathway ensures cell survival after replication stress it potentially contributes to resistance to chemotherapy. Thus inhibition of ATR kinase activity could be useful for cancer treatment.

In oncogene-driven tumor cells (e.g. Ras mutation/upregulation, Myc upregulation, CyclinE overexpression) increased replication stress has been observed as compared to healthy normal cells. ATR suppression in Ras oncogene driven cells was reported to result in substantial tumor cell killing [O. Gilad, B Y Nabet, et al.: Combining ATR suppression with oncogenic Ras synergistically increases genomic instability, causing synthetic lethality or tumorigenesis in a dosage-dependent manner. Cancer Res. 70, 9693-9702, 2010].

Although ATM and ATR are principally activated by different types of DNA damage their signaling includes some cross-talk thus that they can, at least partially, substitute for each others function. This finding suggests some tumor-cell selectivity of pharmaceutical inhibition of ATR. A healthy normal cell, which has ATM and ATR pathways in parallel, arrests in G1 phase of the cell cycle upon induced DNA damage even in presence of an ATR inhibitor. In contrast, a tumor cell which most often deficient in ATM and/or p53 signaling relies on the ATR pathway and undergoes cell death in presence of an ATR inhibitor. This suggests that ATR inhibitors may be used for the treatment of tumors with deficient ATM signaling and/or p53 function.

Details of DDR signaling and the functional role of ATM and ATR were recently reviewed in: E. Fokas, R. Prevo et al.: Targeting ATR in DNA damage response and cancer therapeutics. Cancer Treatment Rev 40, 109-117, 2014. J. M. Wagner & S. H. Kaufmann: Prospects for the use of ATR inhibitors to treat cancer. Pharmaceuticals 3, 1311-1334, 2010. D. Woods & J. J. Tuchi: Chemotherapy induced DNA damage response. Cancer Biol. Thera. 14, 379-389, 2013. A. Marechal & L. Zou: DNA damage sensing by the ATM and ATR kinases. Cold Spring Harb. Perspect. Biol. 5, a012716, 2013. M. K. Zeman & K. A. Cimprich: Causes and consequences of replication stress. Nat. Cell Biol. 16, 2-9, 2014. S. Llona-Minguez, A. Höglund et al.: Chemical strategies for development of ATR inhibitors. Exp. Rev. Mol. Med. 16, e10, 2014.

Some inhibitors of ATR kinase are known (J. Med. Chem. 2013, 56, 2125-2138; Exp. Rev. Mol. Med. 16, e10, 2014; WO2010054398A1; WO2010071837A1; WO2010073034A1; WO2011143399A1; WO2011143419A1; WO2011143422A1; WO2011143423A2; WO2011143425A2; WO2011143426A1; WO2011154737A1; WO2011163527A1; WO2012138938A1; WO2012178123A1; WO2012178124A1; WO2012178125A1; WO2013049719A1; WO2013049720A1; WO2013049722A1; WO2013049859A1; WO2013071085A1; WO2013071088A1; WO2013071090A1; WO2013071093A1; WO2013071094A1; WO2013152298A1; WO2014062604A1; WO2014089379A1; WO2014143240).

WO 0058307 describe aryl fused 2,4-disubstituted pyridines as NK3 receptor ligands. However, no 1,7-naphthyridine compounds are exemplified.

WO 2006039718 describe aryl nitrogen-containing bicyclic compounds for the prophylaxis and treatment of protein kinase mediated diseases. However, no 1,7-naphthyridine compounds are exemplified.

WO 2008017461 and the Journal of Medicinal Chemistry 2011, 54(22), 7899-7910 describe 1,7-naphthyridine derivatives as p38 MAP kinase inhibitors. The 8-position of the 1,7-naphthyridine derivatives is substituted with a phenyl ring. No 1,7-naphthyridine compounds are exemplified, which are substituted with a heteroaryl group in the 8-position of the 1,7-naphthyridine.

There is a need for the development of ATR inhibitors for treating diseases, in particular hyperproliferative diseases. The problem to be solved by the present invention is to provide further compounds which inhibit ATR. It was found, surprisingly, that 5-alkyl- and 5-alkoxy-2-(morpholin-4-yl)-1,7-naphthyridines of general formula (I) or (Ib) inhibit ATR.

In accordance with a first aspect, the present invention covers compounds of general formula (I)

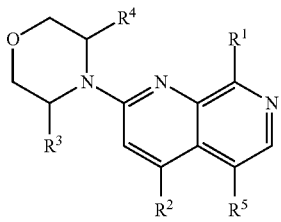

(I)

in which:
$R^1$ represents a group selected from:

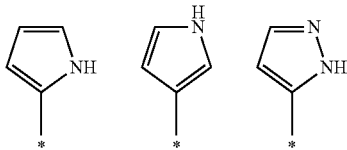

wherein * indicates the point of attachment of said group with the rest of the molecule;

$R^2$ represents hydrogen, halogen, $-NR^7R^8$, CN, $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, $C_4$-$C_6$-cycloalkenyl, 3- to 10-membered heterocycloalkyl, 4- to 10-membered heterocycloalkenyl, phenyl, heteroaryl, $-(CO)OR^7$, $-(CO)NR^7R^8$, $-(SO_2)R^9$, $-(SO)R^9$, $-SR^9$, $-(SO_2)NR^7R^8$, $-NR^7(SO_2)R^9$, $-((SO)=NR^{11})R^{10}$, $-N=(SO)R^9R^{10}$, $-SiR^{10}R^{11}R^{12}$, $-(PO)(OR^7)_2$, $-(PO)(OR^7)R^{10}$ or $-(PO)(R^{10})_2$, wherein each $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, 3- to 10-membered heterocycloalkyl, phenyl or heteroaryl is optionally substituted, one or more times, independently from each other, with halogen, OH, $-CN$, $-NR^7R^8$, $C_1$-$C_6$-alkyl, $C_1$-$C_6$-haloalkyl, $C_1$-$C_4$-hydroxyalkyl, phenyl-$C_1$-$C_4$-alkyl, ($C_1$-$C_4$-alkoxy)-($C_1$-$C_4$-alkyl)-, $C_1$-$C_6$-alkoxy, $C_3$-$C_6$-cycloalkyl, 3- to 6-membered heterocycloalkyl, phenyl, $-(CO)OR^7$, $-(CO)NR^7R^8$, $-NR^7(CO)R^{10}$, $-NR^8(CO)OR^7$, $-NR^8(CO)$ $NR^7R^8$, $-(SO_2)R^9$, $-(SO)R^9$, $-SR^9$, $-(SO_2)NR^7R^8$, $-NR^7(SO_2)R^9$, $-((SO)=NR^{11})R^{10}$, $-N=(SO)R^9R^{10}$, $-(PO)(OR^7)_2$, $-(PO)(OR^7)R^{10}$, $-(PO)(R^{10})_2$, with a heteroaryl group which is optionally substituted one or more times with $C_1$-$C_4$-alkyl, or wherein two substituents of said phenyl group attached to two adjacent phenyl ring atoms are linked to one another to jointly form a methylenedioxy, ethylenedioxy, ethyleneoxy or trimethyleneoxy group;

wherein each 4- to 10-membered heterocycloalkenyl is optionally substituted, one or more times, indepently from each other, with $C_1$-$C_4$-alkyl;

$R^3$, $R^4$ represent, independently from each other, hydrogen or methyl;

$R^5$ represents $C_1$-$C_6$-alkyl, $C_1$-$C_6$-haloalkyl or $C_1$-$C_6$-alkoxy;

$R^7$, $R^8$ represent, independently from each other, hydrogen, $C_1$-$C_6$-alkyl, $C_3$-$C_6$-cycloalkyl, phenyl or phenyl-$CH_2-$, which phenyl is optionally substituted, one or more times, with halogen; or $R^7$ and $R^8$ together represent a 4-, 5-, 6- or 7-membered cyclic amine group, which is optionally substituted, one or more times, independently from each other, with a substituent selected from $C_1$-$C_6$-alkyl, $C_1$-$C_6$-haloalkyl, said 4-, 5-, 6- or 7-membered cyclic amine group optionally containing one further heteroatom selected from the group consisting of O, N and S;

$R^9$ represents $C_1$-$C_4$-alkyl or phenyl, wherein each $C_1$-$C_4$-alkyl or phenyl is optionally substituted, one or more times, independently from each other, with $R^{13}$;

$R^{10}$ represents $C_1$-$C_4$-alkyl; or $R^9$ and $R^{10}$ together, in case of $-N=(SO)R^9R^{10}$ group, represent a 5- to 8-membered heterocycloalkyl group;

$R^{11}$ represents hydrogen, $C_1$-$C_4$-alkyl, $-(CO)OR^7$, $-(CO)NR^7R^8$ or CN;

$R^{12}$ represents hydrogen or $C_1$-$C_4$-alkyl;

$R^{13}$ represents halogen, OH, $-NR^7R^8$, CN, $NO_2$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_6$-cycloalkyl, $-(CO)OR^7$ or $-(CO)NR^7R^8$;

or a stereoisomer, a tautomer, an N-oxide, a hydrate, a solvate, or a salt thereof, or a mixture of same.

The terms as mentioned in the present text have the following meanings:

The term "halogen atom", "halo-" or "Hal-" is to be understood as meaning a fluorine, chlorine, bromine or iodine atom.

The term "$C_1$-$C_6$-alkyl" is to be understood as meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl or iso-propyl group.

The term "$C_1$-$C_6$-haloalkyl" is to be understood as meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said $C_1$-$C_6$-haloalkyl group is, for example, $-CF_3$, $-CHF_2$, $-CH_2F$, $-CF_2CF_3$ or $-CH_2CF_3$.

The term "$C_1$-$C_4$-hydroxyalkyl" is to be understood as meaning a linear or branched, saturated, monovalent hydrocarbon group in which the term "$C_1$-$C_4$-alkyl" is defined supra, and in which one or more hydrogen atoms is replaced by a hydroxy group, e.g. a hydroxymethyl, 1-hydroxyethyl, 2-hydroxyethyl, 1,2-dihydroxyethyl, 3-hydroxypropyl, 2-hydroxypropyl, 2,3-dihydroxypropyl, 1,3-dihydroxypropan-2-yl, 3-hydroxy-2-methyl-propyl, 2-hydroxy-2-methylpropyl, 1-hydroxy-2-methyl-propyl group.

The term "$C_1$-$C_6$-alkoxy" is to be understood as meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof. Particularly, said "$C_1$-$C_6$-alkoxy" can contain 1, 2, 3, 4 or 5 carbon atoms, (a "$C_1$-$C_5$-alkoxy"), preferably 1, 2, 3 or 4 carbon atoms ("$C_1$-$C_4$-alkoxy").

The term "$C_1$-$C_6$-haloalkoxy" is to be understood as meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said $C_1$-$C_6$-haloalkoxy group is, for example, —$OCF_3$, —$OCHF_2$, —$OCH_2F$, —$OCF_2CF_3$, or —$OCH_2CF_3$.

The term "$C_2$-$C_6$-alkenyl" is to be understood as meaning a linear or branched, monovalent hydrocarbon group, which contains one or more double bonds, and which has 2, 3, 4, 5 or 6 carbon atoms or 2, 3 or 4 carbon atoms ("$C_2$-$C_4$-alkenyl), particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_3$-$C_{10}$-cycloalkyl" is to be understood as meaning a saturated, monovalent, mono-, or bicyclic hydrocarbon ring which contains 3, 4, 5, 6, 7, 8, 9 or 10 carbon atoms ("$C_3$-$C_{10}$-cycloalkyl"). Said $C_3$-$C_{10}$-cycloalkyl group is for example, a monocyclic hydrocarbon ring, e.g. a cyclopropyl, cyclobutyl, cyclopentyl, cyclohexyl, cycloheptyl, cyclooctyl, cyclononyl or cyclodecyl, or a bicyclic hydrocarbon ring, e.g. a perhydropentalenylene or decalin ring. Particularly, said ring contains 3, 4, 5 or 6 carbon atoms ("$C_3$-$C_6$-cycloalkyl"), preferably cyclopropyl.

The term "$C_4$-$C_6$-cycloalkenyl" is to be understood as meaning a monovalent, monocyclic hydrocarbon ring which contains 4, 5 or 6 carbon atoms. Said $C_4$-$C_6$-cycloalkenyl group is for example, a cyclobutenyl, cyclopentenyl or cyclohexenyl group.

The term "3- to 10-membered heterocycloalkyl" is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl or $C_1$-$C_6$-haloalkyl group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused. Preferably, the 3- to 6-membered heterocycloalkyl is a tetrahydrofuranyl, tetrahydropyranyl or piperazinyl.

Said heterocycloalkyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "3- to 10-membered heterocycloalkoxy" of formula —O-heterocycloalkyl, in which the term "heterocycloalkyl" is defined supra, is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, a $C_1$-$C_6$-alkyl or $C_1$-$C_6$-haloalkyl group and which is connected to the rest of the molecule via an oxygen atom, e.g. a pyrrolidineoxy, tetrahydrofuraneoxy or tetrahydropyranoxy.

The term "4- to 10-membered heterocycloalkenyl" is to be understood as meaning an unsaturated, monovalent, mono- or bicyclic hydrocarbon ring which contains 3, 4, 5, 6, 7, 8 or 9 carbon atoms, and one or more heteroatom-containing groups selected from C(=O), O, S, S(=O), S(=O)$_2$, NRa, in which R$^a$ represents a hydrogen atom, or a $C_1$-$C_6$-alkyl or $C_1$-$C_6$-haloalkyl group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3,6-dihydro-2H-pyran-4-yl, 3,6-dihydro-2H-thiopyran-4-yl, 1,2,3,6-tetrahydropyridin-4-yl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, 4H-[1,4]thiazinyl or 5,6-dihydroimidazo[1,2-a]pyrazin-7(8H)-yl group or it may be benzo fused.

The term "heteroaryl" is understood as meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), 5 or 6 or 9 or 10 ring atoms (a "5- to 10-membered heteroaryl" group) or particularly 5 or 6 ring atoms ("5- to 6-membered heteroaryl" group), and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, oxepinyl or 1H-pyrrolo[2,3-b]pyridin-4-yl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

Further, as used herein, the term "$C_2$-$C_4$", as used throughout this text, e.g. in the context of "$C_2$-$C_4$-alkenyl" is to be understood as meaning a alkenyl group having a finite number of carbon atoms of 2 to 4, i.e. 2, 3 or 4 carbon atoms. It is to be understood further that said term "$C_2$-$C_4$" is to be interpreted as any sub-range comprised therein, e.g. $C_2$-$C_4$, $C_2$-$C_3$, $C_3$-$C_4$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention may contain sulphur atoms which are asymmetric, such as an asymmetric sulphoxide or sulphoximine group, of structure:

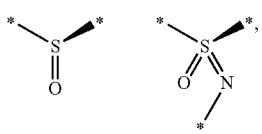

for example,
in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers.

Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

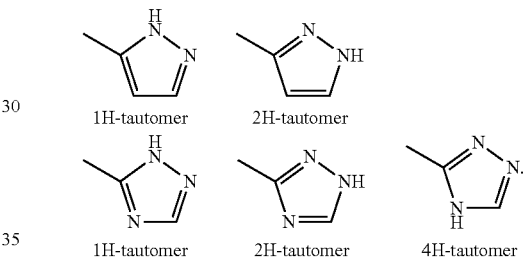

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

Furthermore, the present invention includes all possible crystalline forms, or polymorphs, of the compounds of the present invention, either as single polymorphs, or as a mixture of more than one polymorphs, in any ratio.

When radicals in the compounds of the present invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease (the term "disease" includes but is not limited a condition, a disorder, an injury or a health problem), or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease or a development or advancement of such states and/or the symptoms of such states.

The treatment or prevention of a disease may be partial or complete.

In another embodiment, the present invention covers compounds of general formula (I)

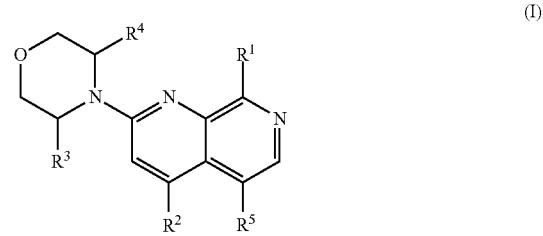

(I)

in which:

$R^1$ represents a group:

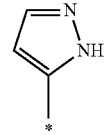

wherein * indicates the point of attachment of said group with the rest of the molecule;

$R^2$ represents hydrogen, halogen, $-NR^7R^8$, CN, $C_1$-$C_4$-alkyl, $C_1$-$C_4$-alkoxy, 3- to 6-membered heterocycloalkoxy, $C_3$-$C_6$-cycloalkyl, $C_4$-$C_6$-cycloalkenyl, 3- to 6-membered heterocycloalkyl, phenyl, heteroaryl, $-(CO)OR^7$, $-(CO)NR^7R^8$, $-(SO_2)R^9$, $-(SO)R^9$, $-SR^9$, $-(SO_2)NR^7R^8$, $-NR^7(SO_2)R^9$, $-((SO)=NR^{11})R^{10}$, $-N=(SO)R^9R^{10}$, $-(PO)(OR^7)_2$, $-(PO)(OR^7)R^{10}$ or $-(PO)(R^{10})_2$, wherein each $C_1$-$C_4$-alkyl, $C_1$-$C_4$-alkoxy, 3- to 6-membered heterocycloalkoxy, $C_3$-$C_6$-cycloalkyl, 3- to 6-membered heterocycloalkyl, phenyl or heteroaryl is optionally substituted, one or more times, independently from each other, with halogen, OH, $-CN$, $-NR^7R^8$, $C_1$-$C_4$-alkyl, $C_1$-$C_4$-haloalkyl, $C_1$-$C_4$-hydroxyalkyl, phenyl-$C_1$-$C_2$-alkyl, $(C_1$-$C_4$-alkoxy)-$(C_1$-$C_4$-alkyl)-, $C_1$-$C_4$-alkoxy, $C_3$-$C_6$-cycloalkyl, 3- to 6-membered heterocycloalkyl, phenyl, $-(CO)OR^7$, $-(CO)NR^7R^8$, $-NR^7(CO)R^{10}$, $-NR^8(CO)OR^7$, $-NR^8(CO)$ $NR^7R^8$, $-(SO_2)R^9$, $-(SO)R^9$, $-SR^9$, $-(SO_2)NR^7R^8$, $-NR^7(SO_2)R^9$, $-((SO)=NR^{11})R^{10}$, $-N=(SO)R^9R^{10}$, with a heteroaryl group which is optionally substituted one or more times with $C_1$-$C_4$-alkyl, or wherein two substituents of said phenyl group attached to two adjacent phenyl ring atoms are linked to one another to jointly form a methylenedioxy, ethylenedioxy, ethyleneoxy or trimethyleneoxy group;

$R^3$, $R^4$ represent, independently from each other, hydrogen or methyl;

$R^5$ represents $C_1$-$C_4$-alkyl;

$R^7$, $R^8$ represent, independently from each other, hydrogen, $C_1$-$C_6$-alkyl, $C_3$-$C_6$-cycloalkyl, phenyl or phenyl-$CH_2$—, which phenyl is optionally substituted, one or more times, with halogen; or $R^7$ and $R^8$ together represent a 5- or 6-membered cyclic amine group, which is optionally substituted, one or more times, independently from each other, with a substituent selected from $C_1$-$C_4$-alkyl, $C_1$-$C_4$-haloalkyl, said 5- or 6-membered cyclic amine group optionally containing one further heteroatom selected from the group consisting of O, N and S;

$R^9$ represents $C_1$-$C_4$-alkyl;

$R^{10}$ represents $C_1$-$C_4$-alkyl; or $R^9$ and $R^{10}$ together, in case of —N=(SO)$R^9R^{10}$ group, represent a 5- to 6-membered heterocycloalkyl group;

$R^{11}$ represents hydrogen or $C_1$-$C_4$-alkyl;

or a stereoisomer, a tautomer, an N-oxide, a hydrate, a solvate, or a salt thereof, or a mixture of same.

In an other embodiment, the present invention covers compounds of general formula (I)

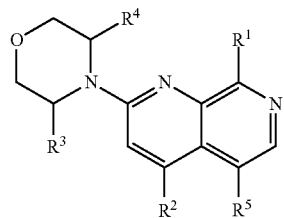

(I)

in which:

$R^1$ represents a group selected from:

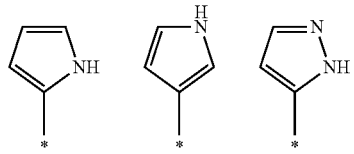

wherein * indicates the point of attachment of said group with the rest of the molecule;

$R^2$ represents hydrogen, halogen, —NR$^7$R$^8$, CN, $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, $C_4$-$C_6$-cycloalkenyl, 3- to 10-membered heterocycloalkyl, 4- to 10-membered heterocycloalkenyl, phenyl, heteroaryl, —(CO)OR$^7$, —(CO)NR$^7$R$^8$, —(SO$_2$)R$^9$, —(SO)R$^9$, —SR$^9$, —(SO$_2$)NR$^7$R$^8$, —NR$^7$(SO$_2$)R$^9$, —((SO)=NR$^{11}$)R$^{10}$, —N=(SO)R$^9$R$^{10}$, —SiR$^{10}$R$^{11}$R$^{12}$, —(PO)(OR$^7$)$_2$, —(PO)(OR$^7$)R$^{10}$ or —(PO)(R$^{10}$)$_2$, wherein each $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, 3- to 10-membered heterocycloalkyl, phenyl or heteroaryl is optionally substituted, one or more times, independently from each other, with halogen, OH, —CN, —NR$^7$R$^8$, $C_1$-$C_6$-alkyl, $C_1$—C-haloalkyl, $C_1$-$C_4$-hydroxyalkyl, phenyl-$C_1$-$C_4$-alkyl, ($C_1$-$C_4$-alkoxy)-($C_1$-$C_4$-alkyl)-, $C_1$-$C_6$-alkoxy, $C_3$-$C_6$-cycloalkyl, 3- to 6-membered heterocycloalkyl, phenyl, —(CO)OR$^7$, —(CO)NR$^7$R$^8$, —NR(CO)R$^{10}$, —NR$^8$(CO)OR$^7$, —NR$^8$(CO)NR$^7$R$^8$, —(SO$_2$)R$^9$, —(SO)R$^9$, —SR$^9$, —(SO$_2$)NR$^7$R$^8$, —NR$^7$(SO$_2$)R$^9$, —((SO)=NR$^{11}$)R$^{10}$, —N=(SO)R$^9$R$^{10}$, —(PO)(OR$^7$)$_2$, —(PO)(OR$^7$)R$^{10}$, —(PO)(R$^{10}$)$_2$, with a heteroaryl group which is optionally substituted one or more times with $C_1$-$C_4$-alkyl, or wherein two substituents of said phenyl group attached to two adjacent phenyl ring atoms are linked to one another to jointly form a methylenedioxy, ethylenedioxy, ethyleneoxy or trimethyleneoxy group;

wherein each 4- to 10-membered heterocycloalkenyl is optionally substituted, one or more times, indepently from each other, with $C_1$-$C_4$-alkyl;

$R^3$, $R^4$ represent, independently from each other, hydrogen or methyl;

$R^5$ represents hydrogen, $C_1$-$C_6$-alkyl, $C_1$-$C_6$-haloalkyl or $C_1$-$C_6$-alkoxy;

$R^7$, $R^8$ represent, independently from each other, hydrogen, $C_1$-$C_6$-alkyl, $C_3$-$C_6$-cycloalkyl, phenyl or phenyl-$CH_2$—, which phenyl is optionally substituted, one or more times, with halogen; or $R^7$ and $R^8$ together represent a 4-, 5-, 6- or 7-membered cyclic amine group, which is optionally substituted, one or more times, independently from each other, with a substituent selected from $C_1$-$C_6$-alkyl, $C_1$-$C_6$-haloalkyl, said 4-, 5-, 6- or 7-membered cyclic amine group optionally containing one further heteroatom selected from the group consisting of O, N and S;

$R^9$ represents $C_1$-$C_4$-alkyl or phenyl, wherein each $C_1$-$C_4$-alkyl or phenyl is optionally substituted, one or more times, independently from each other, with $R^{13}$;

$R^{10}$ represents $C_1$-$C_4$-alkyl; or $R^9$ and $R^{10}$ together, in case of —N=(SO)R$^9$R$^{10}$ group, represent a 5- to 8-membered heterocycloalkyl group;

$R^{11}$ represents hydrogen, $C_1$-$C_4$-alkyl, —(CO)OR$^7$, —(CO)NR$^7$R$^8$ or CN;

$R^{12}$ represents hydrogen or $C_1$-$C_4$-alkyl;

$R^{13}$ represents halogen, OH, —NR$^7$R$^8$, CN, NO$_2$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_6$-cycloalkyl, —(CO)OR$^7$ or —(CO)NR$^7$R$^8$;

or a stereoisomer, a tautomer, an N-oxide, a hydrate, a solvate, or a salt thereof, or a mixture of same.

In accordance with another embodiment the present invention covers compounds of general formula (Ib)

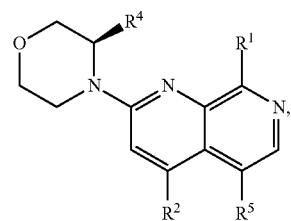

(Ib)

in which $R^1$, $R^2$, $R^4$, $R^5$, $R^7$, $R^8$, $R^9$, $R^{10}$, $R^{11}$, $R^{12}$ and $R^{13}$ are as defined for the compound of general formula (I) supra or infra.

In another embodiment the present invention covers compounds of general formula (Ib)
in which:
R¹ represents a group:

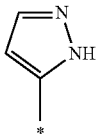

wherein * indicates the point of attachment of said group with the rest of the molecule;
R² represents —NR⁷R⁸, C₁-C₄-alkoxy, C₄-C₆-cycloalkenyl, 6-membered heterocycloalkyl, phenyl, heteroaryl, —(CO)OR⁷, —N═(SO)R⁹R¹⁰, —(PO)(OR⁷)R¹⁰ or —(PO)(R¹⁰)₂,
wherein each C₁-C₄-alkoxy, 6-membered heterocycloalkyl, phenyl or heteroaryl is optionally substituted, one or more times, independently from each other, with halogen, OH, —CN, —NR⁷R⁸, C₁-C₄-alkyl, hydroxymethyl, phenyl-CH₂—, methoxymethyl, C₁-C₄-alkoxy, 6-membered heterocycloalkyl, —(CO)OR⁷, —(CO)NR⁷R⁸, —(SO₂)R⁹, —(SO)R⁹, —SR⁹, —NR⁷(SO₂)R⁹, or
wherein two substituents of said phenyl group attached to two adjacent phenyl ring atoms are linked to one another to jointly form an ethylenedioxy group;
R⁴ represents methyl;
R⁵ represents methyl;
R⁷, R⁸ represent, independently from each other, hydrogen, C₁-C₆-alkyl, cyclopropyl, phenyl or phenyl-CH₂—, which phenyl is optionally substituted, one or more times, with halogen; or
R⁷ and R⁸ together represent a 5-membered cyclic amine group;
R⁹ represents methyl or ethyl;
R¹⁰ represents methyl or ethyl; or
R⁹ and R¹⁰ together, in case of —N═(SO)R⁹R¹⁰ group, represent a 5-membered heterocycloalkyl group;
or a stereoisomer, a tautomer, an N-oxide, a hydrate, a solvate, or a salt thereof, or a mixture of same.

In accordance with another embodiment the present invention covers compounds of general formula (Ib), in which
R¹ represents a group:

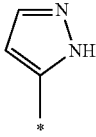

wherein * indicates the point of attachment of said group with the rest of the molecule;
R² represents —N-methyl-(2,2-dimethylpropyl), propan-2-yloxy, cyclopent-1-en-1-yl, 6-membered heterocycloalkyl, phenyl, heteroaryl, —(CO)O-methyl, —N═(SO)diethyl, —N═(SO)(CH₂)₄, —(PO)(O-ethyl)methyl, —(PO)(O-(2-methylpropyl))methyl or —(PO)(methyl)₂,
wherein each 6-membered heterocycloalkyl, phenyl or heteroaryl is optionally substituted, one or more times, independently from each other, with halogen, OH, —CN, —NR⁷R⁸, C₁-C₄-alkyl, hydroxymethyl, phenyl-CH₂—, methoxymethyl, C₁-C₄-alkoxy, 6-membered heterocycloalkyl, —(CO)OR⁷, —(CO)NR⁷R⁸, —(SO₂)R⁹, —(SO)R⁹, —SR⁹, —NR⁷(SO₂)R⁹, or
wherein two substituents of said phenyl group attached to two adjacent phenyl ring atoms are linked to one another to jointly form an ethylenedioxy group;
R⁴ represents methyl;
R⁵ represents methyl;
R⁷, R⁸ represent, independently from each other, hydrogen, C₁-C₅-alkyl, cyclopropyl, phenyl or unsubstituted phenyl-CH₂—, which phenyl is optionally substituted, one or more times, with halogen; or
R⁷ and R⁸ together represent a 5-membered cyclic amine group
R⁹ represents methyl or ethyl;
R¹⁰ represents methyl or ethyl; or
R⁹ and R¹⁰ together, in case of —N═(SO)R⁹R¹⁰ group, represent a tetramethylene group;
or a stereoisomer, a tautomer, an N-oxide, a hydrate, a solvate, or a salt thereof, or a mixture of same.

In accordance with another embodiment the present invention covers compounds of general formula (Ib), in which
R¹ represents a group:

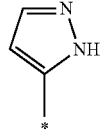

wherein * indicates the point of attachment of said group with the rest of the molecule;
R² represents propan-2-yloxy, —N═(SO)diethyl, —(PO)(O-ethyl)methyl, 1-methyl-1H-pyrazol-5-yl, morpholin-4-yl, 4-(hydroxymethyl)piperidin-1-yl, 4-(methylsulfonyl)piperazin-1-yl, 1-methyl-1H-imidazol-5-yl or 2-methyl-1,3-thiazol-5-yl;
R⁴ represents methyl;
R⁵ represents methyl;
or a stereoisomer, a tautomer, an N-oxide, a hydrate, a solvate, or a salt thereof, or a mixture of same.

In accordance with another embodiment the present invention covers compounds of general formula (Ib), in which
R¹ represents a group selected from:

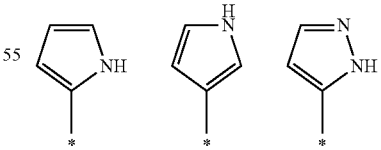

wherein * indicates the point of attachment of said group with the rest of the molecule;
or a stereoisomer, a tautomer, an N-oxide, a hydrate, a solvate, or a salt thereof, or a mixture of same.

In accordance with another embodiment the present invention covers compounds of general formula (Ib), in which $R^1$ represents:

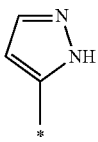

wherein * indicates the point of attachment of said group with the rest of the molecule;

or a stereoisomer, a tautomer, an N-oxide, a hydrate, a solvate, or a salt thereof, or a mixture of same.

In another embodiment the present invention relates to compounds of formula (I) or (Ib), in which $R^1$ represents a group selected from:

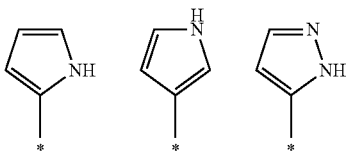

wherein * indicates the point of attachment of said group with the rest of the molecule;

or a stereoisomer, a tautomer, an N-oxide, a hydrate, a solvate, or a salt thereof, or a mixture of same.

In another embodiment the present invention relates to compounds of formula (I) or (Ib), in which $R^1$ represents a group selected from:

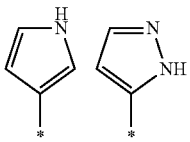

wherein * indicates the point of attachment of said group with the rest of the molecule;

or a stereoisomer, a tautomer, an N-oxide, a hydrate, a solvate, or a salt thereof, or a mixture of same.

In another embodiment the present invention relates to compounds of formula (I) or (Ib), in which $R^1$ represents

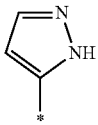

wherein * indicates the point of attachment of said group with the rest of the molecule;

or a stereoisomer, a tautomer, an N-oxide, a hydrate, a solvate, or a salt thereof, or a mixture of same.

In another embodiment the present invention relates to compounds of formula (I) or (Ib), in which
$R^2$ represents hydrogen, halogen, —$NR^7R^8$, CN, $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, $C_4$-$C_6$-cycloalkenyl, 3- to 10-membered heterocycloalkyl, 4- to 10-membered heterocycloalkenyl, phenyl, heteroaryl, —(CO)$OR^7$, —(CO)$NR^7R^8$, —($SO_2$)$R^9$, —(SO)$R^9$, —$SR^9$, —($SO_2$)$NR^7R^8$, —$NR^7(SO_2)R^9$, —((SO)=$NR^{11}$)$R^{10}$, —N=(SO)$R^9R^{10}$, —$SiR^{10}R^{11}R^{12}$, —(PO)($OR^7$)$_2$, —(PO)($OR^7$)$R^{10}$ or —(PO)($R^{10}$)$_2$, wherein each $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, 3- to 10-membered heterocycloalkyl, phenyl or heteroaryl is optionally substituted, one or more times, independently from each other, with halogen, OH, —CN, —$NR^7R^8$, $C_1$-$C_6$-alkyl, $C_1$—C-haloalkyl, $C_1$-$C_4$-hydroxyalkyl, phenyl-$C_1$-$C_4$-alkyl, ($C_1$-$C_4$-alkoxy)-($C_1$-$C_4$-alkyl)-, $C_1$-$C_6$-alkoxy, $C_3$-$C_6$-cycloalkyl, 3- to 6-membered heterocycloalkyl, phenyl, —(CO)$OR^7$, —(CO)$NR^7R^8$, —$NR^7(CO)R^{10}$, —$NR^8$(CO)$OR^7$, —$NR^8$(CO) $NR^7R^8$, —($SO_2$)$R^9$, —(SO)$R^9$, —$SR^9$, —($SO_2$)$NR^7R^8$, —$NR^7(SO_2)R^9$, —((SO)=$NR^{11}$)$R^{10}$, —N=(SO)$R^9R^{10}$, —(PO)($OR^7$)$_2$, —(PO)($OR^7$)$R^{10}$, —(PO)($R^{10}$)$_2$, with a heteroaryl group which is optionally substituted one or more times with $C_1$-$C_4$-alkyl, or wherein two substituents of said phenyl group attached to two adjacent phenyl ring atoms are linked to one another to jointly form a methylenedioxy, ethylenedioxy, ethyleneoxy or trimethyleneoxy group;

wherein each 4- to 10-membered heterocycloalkenyl is optionally substituted, one or more times, indepently from each other, with $C_1$-$C_4$-alkyl;

or a stereoisomer, a tautomer, an N-oxide, a hydrate, a solvate, or a salt thereof, or a mixture of same.

In another embodiment the present invention relates to compounds of formula (I) or (Ib), in which
$R^2$ represents hydrogen, halogen, —$NR^7R^8$, CN, $C_1$-$C_4$-alkyl, $C_1$-$C_4$-alkoxy, 3- to 6-membered heterocycloalkoxy, $C_3$-$C_6$-cycloalkyl, $C_4$-$C_6$-cycloalkenyl, 3- to 6-membered heterocycloalkyl, phenyl, heteroaryl, —(CO)$OR^7$, —(CO)$NR^7R^8$, —($SO_2$)$R^9$, —(SO)$R^9$, —$SR^9$, —($SO_2$)$NR^7R^8$, —$NR^7(SO_2)R^9$, —((SO)=$NR^{11}$)$R^{10}$, —N=(SO)$R^9R^{10}$, —(PO)($OR^7$)$_2$, —(PO)($OR^7$)$R^1$ or —(PO)($R^{10}$)$_2$, wherein each $C_1$-$C_4$-alkyl, $C_1$-$C_4$-alkoxy, 3- to 6-membered heterocycloalkoxy, $C_3$-$C_6$-cycloalkyl, 3- to 6-membered heterocycloalkyl, phenyl or heteroaryl is optionally substituted, one or more times, independently from each other, with halogen, OH, —CN, —$NR^7R^8$, $C_1$-$C_4$-alkyl, $C_1$-$C_4$-haloalkyl, $C_1$-$C_4$-hydroxyalkyl, phenyl-$C_1$-$C_2$-alkyl, ($C_1$-$C_4$-alkoxy)-($C_1$-$C_4$-alkyl)-, $C_1$-$C_4$-alkoxy, $C_3$-$C_6$-cycloalkyl, 3- to 6-membered heterocycloalkyl, phenyl, —(CO)$OR^7$, —(CO)$NR^7R^8$, —$NR^7(CO)R^{10}$, —$NR^8$(CO)$OR^7$, —$NR^8$(CO) $NR^7R^8$, —($SO_2$)$R^9$, —(SO)$R^9$, —$SR^9$, —($SO_2$)$NR^7R^8$, —$NR^7(SO_2)R^9$, —((SO)=$NR^{11}$)$R^{10}$, —N=(SO)$R^9R^{10}$, with a heteroaryl group which is optionally substituted one or more times with $C_1$-$C_4$-alkyl, or wherein two substituents of said phenyl group attached to two adjacent phenyl ring atoms are linked to one another to jointly form a methylenedioxy, ethylenedioxy, ethyleneoxy or trimethyleneoxy group;

in which two substituents of said phenyl group, when they are attached to adjacent ring atoms, are optionally linked to one another in such a way that they jointly form a methylenedioxy, ethylenedioxy, ethyleneoxy or trimethyleneoxy group;

or a stereoisomer, a tautomer, an N-oxide, a hydrate, a solvate, or a salt thereof, or a mixture of same.

In another embodiment the present invention relates to compounds of formula (I) or (Ib), in which $R^2$ represents —$NR^7R^8$, $C_1$-$C_4$-alkoxy, $C_4$-$C_6$-cycloalkenyl, 6-membered heterocycloalkyl, phenyl, heteroaryl, —(CO)$OR^7$, —N=(SO)$R^9R^{10}$, —(PO)(O$R^7$)$R^{10}$ or —(PO)($R^{10}$)$_2$, wherein each $C_1$-$C_4$-alkoxy, 6-membered heterocycloalkyl, phenyl or heteroaryl is optionally substituted, one or more times, independently from each other, with halogen, OH, —CN, —$NR^7R^8$, $C_1$-$C_4$-alkyl, hydroxymethyl, phenyl-$CH_2$—, methoxymethyl, $C_1$-$C_4$-alkoxy, 6-membered heterocycloalkyl, —(CO)$OR^7$, —(CO)$NR^7R^8$, —($SO_2$)$R^9$, —(SO)$R^9$, —$SR^9$, —$NR^7$($SO_2$)$R^9$, or wherein two substituents of said phenyl group attached to two adjacent phenyl ring atoms are linked to one another to jointly form an ethylenedioxy group;

or a stereoisomer, a tautomer, an N-oxide, a hydrate, a solvate, or a salt thereof, or a mixture of same.

In another embodiment the present invention relates to compounds of formula (I) or (Ib), in which $R^2$ represents —N-methyl-(2,2-dimethylpropyl), propan-2-yloxy, cyclopent-1-en-1-yl, 6-membered heterocycloalkyl, phenyl, heteroaryl, —(CO)O-methyl, —N=(SO)diethyl, —N=(SO)($CH_2$)$_4$, —(PO)(O-ethyl)methyl, —(PO)(O-(2-methylpropyl))methyl or —(PO)(methyl)$_2$, wherein each 6-membered heterocycloalkyl, phenyl or heteroaryl is optionally substituted, one or more times, independently from each other, with halogen, OH, —CN, —$NR^7R^8$, $C_1$-$C_4$-alkyl, hydroxymethyl, phenyl-$CH_2$—, methoxymethyl, $C_1$-$C_4$-alkoxy, 6-membered heterocycloalkyl, —(CO)$OR^7$, —(CO)$NR^7R^8$, —($SO_2$)$R^9$, —(SO)$R^9$, —$SR^9$, —$NR^7$($SO_2$)$R^9$, or wherein two substituents of said phenyl group attached to two adjacent phenyl ring atoms are linked to one another to jointly form an ethylenedioxy group;

or a stereoisomer, a tautomer, an N-oxide, a hydrate, a solvate, or a salt thereof, or a mixture of same.

In another embodiment the present invention relates to compounds of formula (I) or (Ib), in which $R^2$ represents propan-2-yloxy, —N=(SO)diethyl, —(PO)(O-ethyl)methyl, 1-methyl-1H-pyrazol-5-yl, morpholin-4-yl, 4-(hydroxymethyl)piperidin-1-yl, 4-(methylsulfonyl)piperazin-1-yl, 1-methyl-1H-imidazol-5-yl or 2-methyl-1,3-thiazol-5-yl;

or a stereoisomer, a tautomer, an N-oxide, a hydrate, a solvate, or a salt thereof, or a mixture of same.

In another embodiment the present invention relates to compounds of formula (I), in which $R^3$ represents methyl and $R^4$ represents H.

In another embodiment the present invention relates to compounds of formula (I), in which $R^3$ represents H and $R^4$ represents methyl.

In another embodiment the present invention relates to compounds of formula (I), in which $R^3$ represents H and $R^4$ represents H.

In another embodiment the present invention relates to compounds of formula (I), in which $R^3$ represents methyl and $R^4$ represents methyl.

In another embodiment the present invention relates to compounds of formula (I) or (Ib), in which $R^4$ represents H or methyl.

In another embodiment the present invention relates to compounds of formula (I) or (Ib), in which $R^4$ represents H.

In a preferred embodiment the present invention relates to compounds of formula (I) or (Ib), in which $R^4$ represents methyl.

In another preferred embodiment the present invention relates to compounds of formula (I) or (Ib), in which $R^4$ represents methyl in the absolute configuration R.

In another embodiment the present invention relates to compounds of formula (I) or (Ib), in which $R^5$ represents $C_1$-$C_6$-alkyl, $C_1$-$C_6$-haloalkyl or $C_1$-$C_6$-alkoxy.

In another embodiment the present invention relates to compounds of formula (I) or (Ib), in which $R^5$ represents $C_1$-$C_4$-alkyl, $C_1$-$C_4$-haloalkyl or $C_1$-$C_4$-alkoxy.

In another embodiment the present invention relates to compounds of formula (I) or (Ib), in which $R^5$ represents $C_1$-$C_4$-alkyl or $C_1$-$C_4$-haloalkyl.

In another embodiment the present invention relates to compounds of formula (I) or (Ib), in which $R^5$ represents $C_1$-$C_4$-alkyl or $C_1$-$C_4$-alkoxy.

In another embodiment the present invention relates to compounds of formula (I) or (Ib), in which $R^5$ represents methyl, ethyl, propyl, methoxy, ethoxy or propoxy.

In another embodiment the present invention relates to compounds of formula (I) or (Ib), in which $R^5$ represents $C_1$-$C_4$-alkyl.

In another embodiment the present invention relates to compounds of formula (I) or (Ib), in which $R^5$ represents methyl, ethyl or propyl.

In another embodiment the present invention relates to compounds of formula (I) or (Ib), in which $R^5$ represents methyl.

In another embodiment the present invention relates to compounds of formula (I) or (Ib), in which $R^5$ represents hydrogen.

In another embodiment the present invention relates to compounds of formula (I) or (Ib), in which $R^7$, $R^8$ represent, independently from each other, hydrogen, $C_1$-$C_6$-alkyl, $C_3$-$C_6$-cycloalkyl, phenyl or phenyl-$CH_2$—, which phenyl is optionally substituted, one or more times, with halogen; or $R^7$ and $R^8$ together represent a 4-, 5-, 6- or 7-membered cyclic amine group, which is optionally substituted, one or more times, independently from each other, with a substituent selected from $C_1$-$C_6$-alkyl, $C_1$-$C_6$-haloalkyl, said 4-, 5-, 6- or 7-membered cyclic amine group optionally containing one further heteroatom selected from the group consisting of O, N and S;

In another embodiment the present invention relates to compounds of formula (I) or (Ib), in which $R^7$, $R^8$ represent, independently from each other, hydrogen, $C_1$-$C_6$-alkyl, $C_3$-$C_6$-cycloalkyl, phenyl or phenyl-$CH_2$—, which phenyl is optionally substituted, one or more times, with halogen; or $R^7$ and $R^8$ together represent a 5- or 6-membered cyclic amine group, which is optionally substituted, one or more times, independently from each other, with a substituent selected from $C_1$-$C_4$-alkyl, $C_1$-$C_4$-haloalkyl, said 5- or 6-membered cyclic amine group optionally containing one further heteroatom selected from the group consisting of O, N and S;

In another embodiment the present invention relates to compounds of formula (I) or (Ib), in which $R^7$, $R^8$ represent, independently from each other, hydrogen, $C_1$-$C_5$-alkyl, cyclopropyl, phenyl or unsubstituted phenyl-$CH_2$—, which phenyl is optionally substituted, one or more times, with halogen; or $R^7$ and $R^8$ together represent a 5-membered cyclic amine group;

In another embodiment the present invention relates to compounds of formula (I) or (Ib), in which $R^7$ represents hydrogen and $R^8$ represents hydrogen.

In another embodiment the present invention relates to compounds of formula (I) or (Ib), in which $R^7$ represents hydrogen and $R^8$ represents $C_1$-$C_4$-alkyl.

In another embodiment the present invention relates to compounds of formula (I) or (Ib), in which $R^7$ represents hydrogen and $R^8$ represents $C_1$-$C_5$-alkyl, cyclopropyl or unsubstituted phenyl-$CH_2$—.

In another embodiment the present invention relates to compounds of formula (I) or (Ib), in which $R^7$ represents $C_1$-$C_4$-alkyl and $R^8$ represents $C_1$-$C_4$-alkyl.

In another embodiment the present invention relates to compounds of formula (I) or (Ib), in which $R^9$ represents methyl, ethyl, propyl or phenyl optionally substituted with $R^{13}$.

In another embodiment the present invention relates to compounds of formula (I) or (Ib), in which $R^9$ represents methyl, ethyl or propyl.

In another embodiment the present invention relates to compounds of formula (I) or (Ib), in which $R^9$ represents methyl or ethyl.

In another embodiment the present invention relates to compounds of formula (I) or (Ib), in which $R^{10}$ represents methyl, ethyl or propyl.

In another embodiment the present invention relates to compounds of formula (I) or (Ib), in which $R^{10}$ represents methyl or ethyl.

In another embodiment the present invention relates to compounds of formula (I) or (Ib), in which $R^{10}$ represents methyl.

In another embodiment the present invention relates to compounds of formula (I) or (Ib), in which $R^{10}$ represents ethyl.

In another embodiment the present invention relates to compounds of formula (I) or (Ib), in which $R^9$ and $R^{10}$ together, in case of —N=(SO)$R^9R^{10}$ group, represent a 5-membered heterocycloalkyl group.

In another embodiment the present invention relates to compounds of formula (I) or (Ib), in which $R^9$ and $R^{10}$ together, in case of —N=(SO)$R^9R^{10}$ group, represent a tetramethylene group.

In a further embodiment the invention relates to compounds of formula (I) or (Ib), according to any of the above-mentioned embodiments, in the form of or a stereoisomer, a tautomer, an N-oxide, a hydrate, a solvate, or a salt thereof, or a mixture of same.

It is to be understood that the present invention relates to any sub-combination within any embodiment or aspect of the present invention of compounds of general formula (I) or (Ib), supra.

More particularly still, the present invention covers the title compounds of general formula (I) or (Ib), which are disclosed in the Example section of this text, infra.

In accordance with another aspect, the present invention covers methods of preparing compounds of the present invention, said methods comprising the steps as described below in the schemes 1 to 6 and/or the Experimental Section.

In particular, the present invention covers a method to prepare compounds of general formula 5,

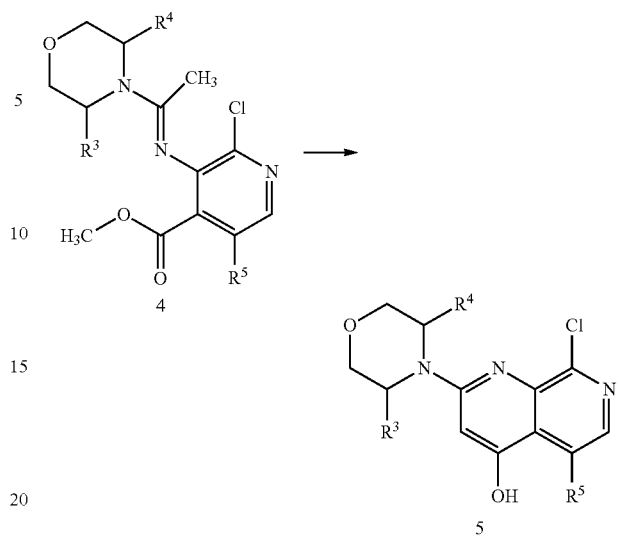

characterized in that compounds of general formula 4, in which $R^3$, $R^4$ and $R^5$ have the same meaning as defined for the compounds of general formula (I) or (Ib) are reacted in an organic solvent, preferably at a temperature between –20° C. and the boiling point of the solvent, preferably between –5° C. and 30° C., using a base, preferably a strong base, to obtain compounds of general formula (5). Preferably, the preparation of compounds of general formula 5 can be performed in an aprotic organic solvent, preferably in tetrahydrofuran or N,N-dimethylformamide.

Preferred strong bases which can be used for the preparation of compounds of general formula 5 are LiHMDS, KHMDS, NaHMDS or LDA.

In particular, the present invention covers a method to prepare compounds of general formula 8,

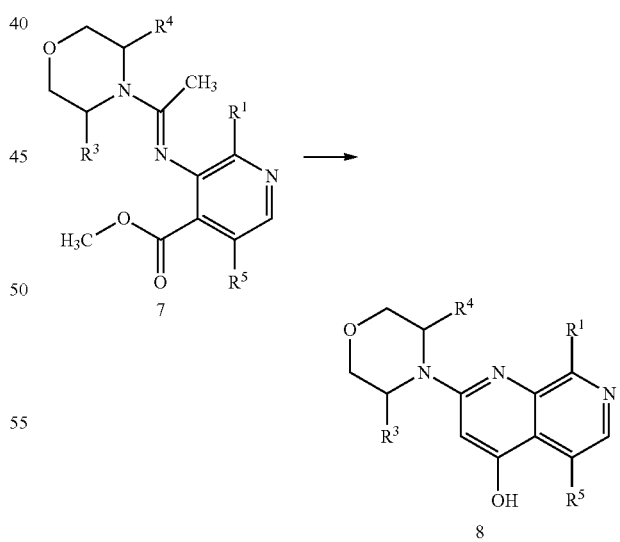

characterized in that compounds of general formula 7, in which $R^1$, $R^3$, $R^4$ and $R^5$ have the same meaning as defined for the compounds of general formula (I) or (Ib) are reacted in an organic solvent, preferably at a temperature between –20° C. and the boiling point of the solvent, preferably between –5° C. and 30° C., using a base, preferably a strong base to obtain compounds of general formula (8).

Preferably, the preparation of compounds of general formula 8 can be performed in an aprotic organic solvent, preferably in tetrahydrofuran or N,N-dimethylformamide.

Preferred strong bases which can be used for the preparation of compounds of general formula 8 are LiHMDS, KHMDS, NaHMDS or LDA.

In accordance with a further aspect, the present invention covers intermediate compounds which are useful in the preparation of compounds of the present invention of general formula (I) or (Ib), particularly in the methods described herein. In particular, the present invention covers compounds of general formula 5,

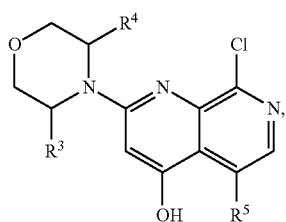

5 in which $R^3$, $R^4$ and $R^5$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 8,

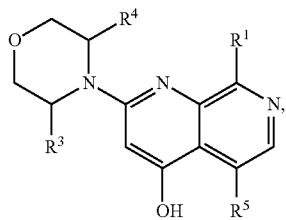

8 in which $R^1$, $R^3$, $R^4$ and $R^5$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 9,

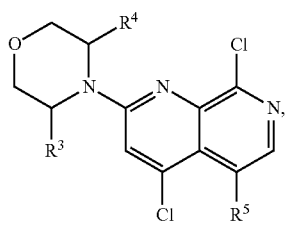

9 in which $R^3$, $R^4$ and $R^5$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 11,

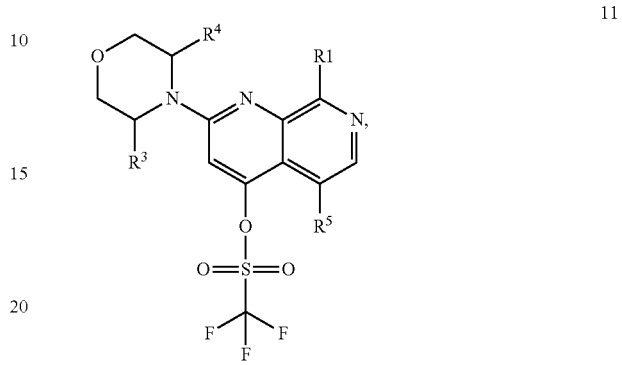

11 in which $R^1$, $R^3$, $R^4$ and $R^5$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 12,

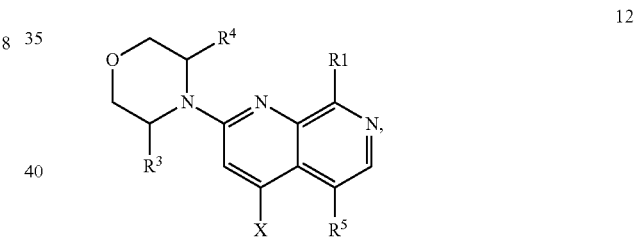

12 in which $R^1$, $R^3$, $R^4$ and $R^5$ are as defined for the compound of general formula (I) or (Ib), supra, and X is chloro, bromo or iodo.

In accordance with a further aspect, the present invention covers intermediate compounds which are useful in the preparation of compounds of the present invention of general formula (I) or (Ib), particularly in the methods described herein. In particular, the present invention covers compounds of general formula 15,

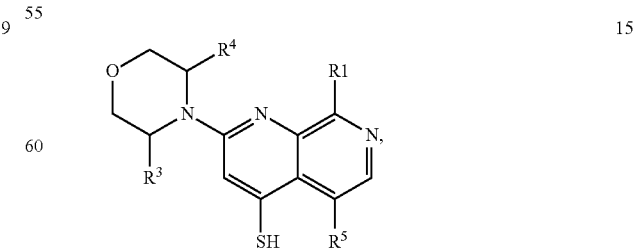

15 in which $R^1$, $R^3$, $R^4$ and $R^5$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 16,

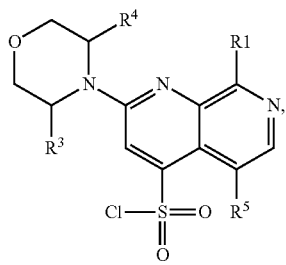

16 in which $R^1$, $R^3$, $R^4$ and $R^5$ are as defined for the compound of general formula (I) or (Ib) supra.

In accordance with a further aspect, the present invention covers intermediate compounds which are useful in the preparation of compounds of the present invention of general formula (Ib), particularly in the methods described herein. In particular, the present invention covers compounds of general formula 39,

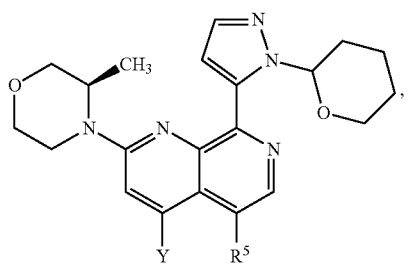

39 in which Y represents OH, —O—SO$_2$—CF$_3$, Cl, Br, I, SH or —SO$_2$Cl, preferably OH, —O—SO$_2$—CF$_3$ or Cl and $R^5$ is as defined for the compound of general formula (I) or (Ib) supra.

In accordance with yet another aspect, the present invention covers the use of the intermediate compounds of general formula 5,

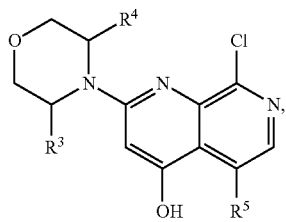

5 in which $R^3$, $R^4$ and $R^5$ are as defined for the compound of general formula (I) or (Ib) supra, for the preparation of a compound of general formula (I) or (Ib) as defined supra.

In accordance with yet another aspect, the present invention covers the use of the intermediate compounds of general formula 8,

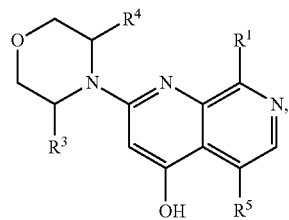

8 in which $R^1$, $R^3$, $R^4$ and $R^5$ are as defined for the compound of general formula (I) or (Ib) supra, for the preparation of a compound of general formula (I) or (Ib) as defined supra.

In accordance with yet another aspect, the present invention covers the use of the intermediate compounds of general formula 9,

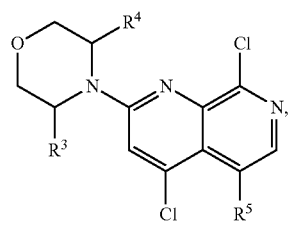

9 in which $R^3$, $R^4$ and $R^5$ are as defined for the compound of general formula (I) or (Ib) supra, for the preparation of a compound of general formula (I) or (Ib) as defined supra.

In accordance with yet another aspect, the present invention covers the use of the intermediate compounds of general formula 11,

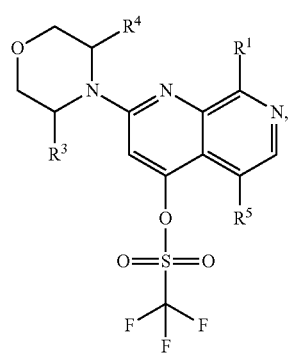

11 in which $R^1$, $R^3$, $R^4$ and $R^5$ are as defined for the compound of general formula (I) or (Ib) supra, for the preparation of a compound of general formula (I) or (Ib) as defined supra.

In accordance with yet another aspect, the present invention covers the use of the intermediate compounds of general formula 12,

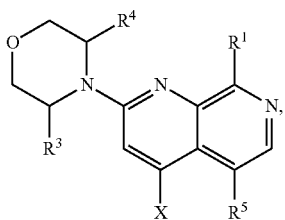

12 in which $R^1$, $R^3$, $R^4$ and $R^5$ are as defined for the compound of general formula (I) or (Ib), supra, and X is chloro, bromo or iodo, for the preparation of a compound of general formula (I) or (Ib) as defined supra.

In accordance with yet another aspect, the present invention covers the use of the intermediate compounds of general formula 15,

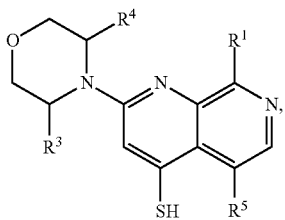

15 in which $R^1$, $R^3$, $R^4$ and $R^5$ are as defined for the compound of general formula (I) or (Ib) supra, for the preparation of a compound of general formula (I) or (Ib) as defined supra.

In accordance with yet another aspect, the present invention covers the use of the intermediate compounds of general formula 16,

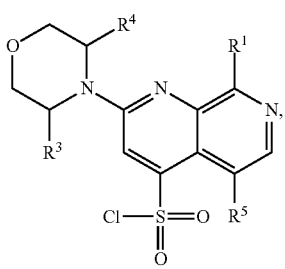

16 in which $R^1$, $R^3$, $R^4$ and $R^5$ are as defined for the compound of general formula (I) or (Ib) supra, for the preparation of a compound of general formula (I) or (Ib) as defined supra.

In accordance with yet another aspect, the present invention covers the use of the intermediate compounds of general formula 39,

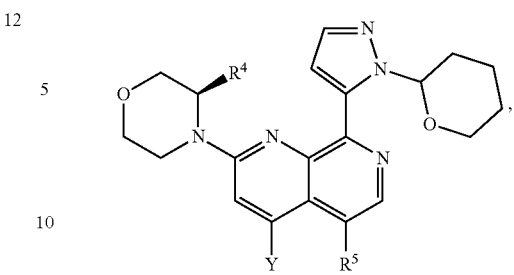

39 in which Y represents OH, —O—SO$_2$—CF$_3$, Cl, Br, I, SH or —SO$_2$Cl, preferably OH, —O—SO$_2$—CF$_3$ or Cl and $R^5$ is as defined for the compound of general formula (I) or (Ib) supra for the preparation of a compound of general formula (I) or (Ib) as defined supra, preferably $R^5$ is methyl.

The compounds of general formula (I) or (Ib) according to the invention show a valuable spectrum of action which could not have been predicted. They are therefore suitable for use as medicaments for the treatment and/or prophylaxis of diseases in humans and animals.

In particular, said compounds of the present invention have surprisingly been found to effectively inhibit ATR kinase and may therefore be used for the treatment or prophylaxis of diseases mediated by ATR kinase, in particular hyperproliferative diseases.

The present invention relates to the compounds of general formula (I) or (Ib) according to the invention for use in the treatment or prophylaxis of a disease, in particular a hyperproliferative disease.

The present invention relates to a method for using the compounds and/or pharmaceutical compositions of the present invention, to treat diseases, in particular hyperproliferative diseases. Compounds can be utilized to inhibit, block, reduce, decrease, etc., cell proliferation and/or cell division, and/or produce apoptosis. This method comprises administering to a mammal in need thereof, in particular a human, an amount of a compound of this invention which is effective to treat the disease. Hyperproliferative diseases include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those diseases also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These diseases have been well characterized in humans, but also exist with a similar etiology in other mammals, and can be treated by administering compounds or pharmaceutical compositions of the present invention.

The present invention relates to the treatment of hyperproliferative diseases with deficient ATM sinaling and/or p53 function, in particular of lung carcinoma, in particular small-cell lung cancer, colorectal cancer, bladder cancer, lymphomas, gliomas, and ovarian cancer.

In particular, the present invention relates to the treatment of lung carcinoma, in particular small-cell lung cancer, colorectal cancer, bladder cancer, lymphomas, in particular diffuse large B-cell lymphoma (DLBC) and mantle cell lymphoma (MCL), prostate cancer, in particular castration-resistant prostate cancer, gliomas, and ovarian cancer The present invention further provides for the use of the compounds of general formula (I) or (Ib) and/or of the pharmaceutical compositions of the present invention for the production of a medicament for the treatment and/or prophylaxis of diseases, especially of the aforementioned diseases, in particular of a hyperproliferative disease.

A further subject matter of the present invention is the use of the compounds of general formula (I) or (Ib) and/or of the pharmaceutical compositions of the present invention in the manufacture of a medicament for the treatment and/or prophylaxis of disorders, in particular the disorders mentioned above.

The present invention furthermore relates to the compounds of general formula (I) or (Ib) for use in a method for the treatment and/or prophylaxis of a disease, in particular of a hyper-proliferative disease.

The present invention further provides a method for treatment and/or prophylaxis of diseases, especially the aforementioned diseases, in particular of a hyperproliferative disease, using an effective amount of the compounds of general formula (I) or (Ib) and/or of the pharmaceutical compositions of the present invention.

The present invention further provides the compounds of general formula (I) or (Ib) and/or of the pharmaceutical compositions of the present invention for use in the treatment and/or prophylaxis of diseases, especially of the aforementioned diseases, in particular of a hyperproliferative disease. The present invention further provides the compounds of general formula (I) or (Ib) and/or of the pharmaceutical compositions of the present invention for use in a method for treatment and/or prophylaxis of the aforementioned diseases, in particular of a hyperproliferative disease.

The present invention further provides a pharmaceutical composition comprising the compound of general formula (I) or (Ib), or a stereoisomer, a tautomer, an N-oxide, a hydrate, a solvate, or a salt thereof, particularly a pharmaceutically acceptable salt thereof, or a mixture of same, with one or more excipient(s), in particular pharmaceutically acceptable excipients, which are inert and nontoxic. Conventional procedures for preparing such pharmaceutical compositions in appropriate dosage forms can be utilized.

The present invention furthermore relates to pharmaceutical compositions, in particular medicaments, which comprise at least one compound according to the invention, conventionally together with one or more pharmaceutically acceptable excipient, and to their use for the above mentioned purposes.

Pharmaceutically acceptable excipients include, inter alia,
fillers and excipients (for example cellulose, microcrystalline cellulose, such as, for example, Avicel®, lactose, mannitol, starch, calcium phosphate such as, for example, Di-Cafos®),
ointment bases (for example petroleum jelly, paraffins, triglycerides, waxes, wool wax, wool wax alcohols, lanolin, hydrophilic ointment, polyethylene glycols),
bases for suppositories (for example polyethylene glycols, cacao butter, hard fat)
solvents (for example water, ethanol, Isopropanol, glycerol, propylene glycol, medium chain-length triglycerides fatty oils, liquid polyethylene glycols, paraffins),
surfactants, emulsifiers, dispersants or wetters (for example sodium dodecyle sulphate, lecithin, phospholipids, fatty alcohols such as, for example, Lanette®, sorbitan fatty acid esters such as, for example, Span®, polyoxyethylene sorbitan fatty acid esters such as, for example, Tween®, polyoxyethylene fatty acid glycerides such as, for example, Cremophor®, polyoxethylene fatty acid esters, polyoxyethylene fatty alcohol ethers, glycerol fatty acid esters, poloxamers such as, for example, Pluronic®),
buffers and also acids and bases (for example phosphates, carbonates, citric acid, acetic acid, hydrochloric acid, sodium hydroxide solution, ammonium carbonate, trometamol, triethanolamine)
isotonicity agents (for example glucose, sodium chloride),
adsorbents (for example highly-disperse silicas)
viscosity-increasing agents, gel formers, thickeners and/or binders (for example polyvinylpyrrolidon, methylcellulose, hydroxypropylmethylcellulose, hydroxypropylcellulose, carboxymethylcellulose-sodium, starch, carbomers, polyacrylic acids such as, for example, Carbopol®, alginates, gelatine),
disintegrants (for example modified starch, carboxymethylcellulose-sodium, sodium starch glycolate such as, for example, Explotab®, cross-linked polyvinylpyrrolidon, croscarmellose-sodium such as, for example, AcDiSol®),
flow regulators, lubricants, glidant and mould release agents (for example magnesium stearate, stearic acid, talc, highly-disperse silicas such as, for example, Aerosil®), coating materials (for example sugar, shellac) and film formers for films or diffusion membranes which dissolve rapidly or in a modified manner (for example polyvinylpyrrolidones such as, for example, Kollidon®, polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®), capsule materials (for example gelatine, hydroxypropylmethylcellulose), synthetic polymers (for example polylactides, polyglycolides, polyacrylates, polymethacrylates such as, for example, Eudragit®, polyvinylpyrrolidones such as, for example, Kollidon®, polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

Further excipients and procedures are described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

The present invention furthermore relates to a pharmaceutical combination, in particular a medicament, comprising at least one compound according to the invention and at least one or more further active ingredients, in particular for the treatment and/or prophylaxis of the above mentioned diseases.

The present invention further provides a pharmaceutical combination comprising: one or more active ingredients selected from a compound of general formula (I) or (Ib), and one or more active ingredients selected from antihyperproliferative, cytostatic or cytotoxic substances for treatment of cancers.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein, for example, a first active ingredient and a second active ingredient are present together in one unit dosage or in a single entity. One example of a "fixed combination" is a pharmaceutical composition wherein a first active ingredient and a second active ingredient are present in admixture for simultaneous administration, such as in a formulation. Another example of a "fixed combination" is a pharmaceutical combination wherein a first active ingredient and a second active ingredient are present in one unit without being in admixture.

A non-fixed combination or "kit-of-parts" in the present invention is used as known to persons skilled in the art and is defined as a combination wherein a first active ingredient and a second active ingredient are present in more than one unit. One example of a non-fixed combination or kit-of-parts is a combination wherein the first active ingredient and the second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutically active ingredients where the combination causes no unacceptable adverse effects. The present invention relates also to such pharmaceutical combinations. For example, the compounds of this invention can be combined with known chemotherapeutic agents and/or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

For example, the compounds of the present invention can be combined with known antihyperproliferative, cytostatic or cytotoxic substances for treatment of cancers.

Examples of suitable antihyperproliferative, cytostatic or cytotoxic combination active ingredients include:

131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+ estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

In a preferred embodiment the pharmaceutical combination of the present invention comprises a compound of general formula (I) or (Ib), and one or more active ingredients selected from carboplatin and cisplatin.

Generally, the use of antihyperproliferative, cytostatic or cytotoxic combination active ingredients in combination with a compound or pharmaceutical composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

In addition, the compounds of general formula (I) can also be used in combination with radiotherapy and/or surgical intervention.

In a further embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In another embodiment of the present invention, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

The compounds of general formula (I) or (Ib) can act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds of general formula (I) or (Ib) can be administered in administration forms suitable for these administration routes.

Suitable administration forms for oral administration are those which release the compounds of general formula (I) or (Ib) in a rapid and/or modified manner, work according to the prior art and contain the compounds of general formula (I) or (Ib) in crystalline and/or amorphous and/or dissolved form, for example tablets (uncoated or coated tablets, for example with enteric or retarded-dissolution or insoluble coatings which control the release of the compound of general formula (I) or (Ib)), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardial, intraspinal or intralumbal route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are pharmaceutical forms for inhalation or inhalation medicaments (including powder inhalers, nebulizers), nasal drops, solutions or sprays; tablets, films/wafers or capsules for lingual, sublingual or buccal administration, films/wafers or capsules, suppositories, ear or eye preparations (for example eye baths, ocular insert, ear drops, ear powders, ear-rinses, ear tampons), vaginal capsules, aqueous suspensions (lotions, shaking mixtures), lipophilic suspensions, ointments, creams, transdermal therapeutic systems (for example patches), milk, pastes, foams, dusting powders, implants, intrauterine coils, vaginal rings or stents.

The compounds of general formula (I) or (Ib) can be converted to the administration forms mentioned. This can be done in a manner known per se, by mixing with pharmaceutically acceptable excipients.

Based upon standard laboratory techniques known to evaluate compounds useful for the treatment of hyperproliferative diseases by standard toxicity tests and by standard pharmacological assays for the determination of treatment of the conditions identified above in mammals, and by comparison of these results with the results of known active ingredients or medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The percentages in the tests and examples which follow are, unless indicated otherwise, percentages by weight; parts are parts by weight. Solvent ratios, dilution ratios and concentration data for liquid/liquid solutions are based in each case on volume.

Syntheses of Compounds (Overview):

The compounds of the present invention can be prepared as described in the following section. The schemes and the procedures described below illustrate general synthetic routes to the compounds of general formula (I) of the invention and are not intended to be limiting. It is clear to the person skilled in the art that the order of transformations as exemplified in the schemes can be modified in various ways.

The order of transformations exemplified in the schemes is therefore not intended to be limiting. In addition, interconversion of any of the substituents can be achieved before and/or after the exemplified transformations. These modifications can be such as the introduction of protecting groups, cleavage of protecting groups, exchange, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example P. G. M. Wuts and T. W. Greene in "Protective Groups in Organic Synthesis", 4$^{th}$ edition, Wiley 2006). Specific examples are described in the subsequent paragraphs. Further, it is possible that two or more successive steps may be performed without work-up being performed between said steps, e.g. a "one-pot" reaction, as is well-known to the person skilled in the art.

The syntheses of the 2-(morpholin-4-yl)-1,7-naphthyridine derivatives according to the present invention are preferably carried out according to the general synthetic sequence, shown in schemes 1-6.

Scheme 1:

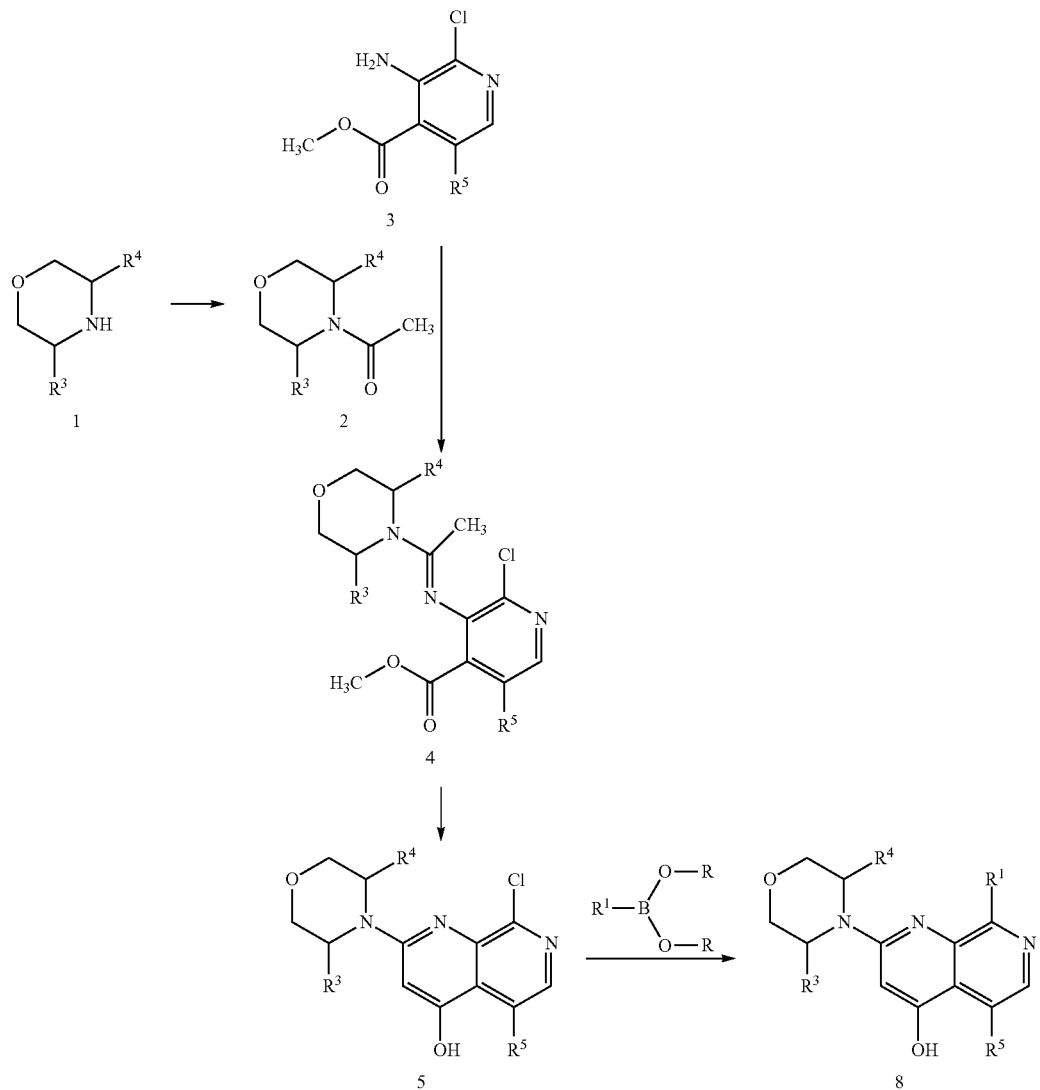

Route for the preparation of compounds of general formula 8, wherein $R^1$, $R^3$, $R^4$ and $R^5$ have the meaning as given for general formula (I). In addition, the substituents $R^1$ can bear a protecting group and the interconversion of any of the substituents $R^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

The starting materials of formula 3 are commercially available or can be prepared according to the literature.

Step 1→2 (Scheme 1)

Amide Formation

In the first step (scheme 1), morpholine derivative 1 (which is commercially available or described in the literature) can be converted to the corresponding acetamide 2 using an acetylating agent. The starting morpholine could either be used as a salt (e.g. HCl salt) or as the free amine.

For example the morpholine 1 can be acetylated using acetyl chloride in an organic solvent such as dichloromethane in the presence of a base such as $K_2CO_3$. The acetylation can also be performed using acetic anhydride in pyridine. Alternatively, acetic acid, a base and an activating reagent generating an active ester in situ in an organic solvent can be used for the transformation. For a review see: C. A. G. N. Montalbetti and V. Falque *Tetrahedron* 2005, 61, 10827-10852 and references therein).

Step 3→4 (Scheme 1)
Amidine Formation

A compound of formula 3 is reacted with a morpholine amide of formula 2 in an amidine forming reaction to give compounds of the general formula 4. Typically the reaction is performed with $POCl_3$ neat or in an organic solvent at a temperature range between 0° C. and the boiling point of the selected solvent. Preferably a halogenated solvent such as chloroform, DCE or DCM is used for the reaction.

Step 4→5 (Scheme 1)
Naphthyridine Formation

The amidines of formula 4 can be converted to the corresponding compounds of formula 5. Typically the reaction is performed in an organic solvent at a temperature between −20° C. and the boiling point of the selected solvent using a strong base. Preferably LiHMDS, KHMDS, NaHMDS or LDA are used as base.

Step 5→8 (Scheme 1)
Palladium Catalyzed Reaction with Boronic Acids

The chloronaphthyridines of formula 5 can be reacted with a boronic acid derivative $R^1$—$B(OR)_2$ to give a compound of formula 8. The boronic acid derivative may be a boronic acid (R═—H) or an ester of the boronic acid, e.g. its isopropyl ester (R═—$CH(CH_3)_2$), preferably an ester derived from pinacol in which the boronic acid intermediate forms a 2-aryl-4,4,5,5-tetramethyl-1,3,2-dioxaborolane (R—R═—$C(CH_3)_2$—$C(CH_3)_2$—). The NH groups of the heterocycle $R^1$ of the boronic acid derivatives may be masked by any suitable protecting group (see Green, Wuts, "*Protective groups in organic synthesis*" 1999, John Wiley & Sons and references cited therein). The corresponding protective group may be removed at any suitable step of the synthesis. Preferably THP (tetrahydropyranyl), BOC (tert-Butoxycarbonyl) or PMB (para-Methoxybenzyl) are used as protective groups during the synthesis.

The coupling reaction is catalyzed by palladium catalysts, e.g. by Pd(0) catalysts like tetrakis(triphenylphosphine)palladium(0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride.

The reaction is preferably carried out in a mixture of a solvent like 1,2-dimethoxyethane, dioxane, DMF, DME, THF, or isopropanol with water and in the presence of a base like potassium carbonate, sodium bicarbonate or potassium phosphate.

(review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (i.e. approx. 20° C.) to the boiling point of the respective solvent. Further on, the reaction can be performed at temperatures above the boiling point using pressure tubes and a microwave oven. The reaction is preferably completed after 1 to 36 hours of reaction time.

Scheme 2:
Route for the preparation of compounds of general formula 11, wherein $R^1$, $R^3$, $R^4$ and $R^5$ have the meaning as given for general formula (I). In addition, the substituents $R^1$ can bear a protecting group and the interconversion of any of the substituents $R^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

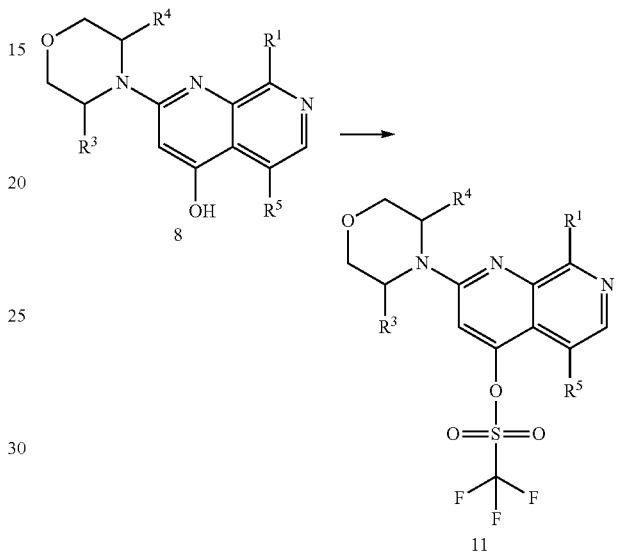

Step 8→11 (Scheme 2)
Triflate Formation

The hydroxy-naphthyridine of the general formula 8 can be converted to the corresponding triflate of formula 11. Typically the hydroxy-naphthyridine 8 is reacted with a triflating reagent such as for example N-Phenylbis(trifluoromethanesulfonimide) with or without a base in an organic solvent such as for example dichloromethane.

Scheme 3:
Route for the preparation of compounds of general formula 12 and 13, wherein R1, R3, R4 and R5 have the meaning as given for general formula (I), supra and R² has the meaning as C1-C6-alkyl or 3- to 10-membered heterocycloalkyl. R1 can bear a protecting group and the interconversion of any of the substituents R1 can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

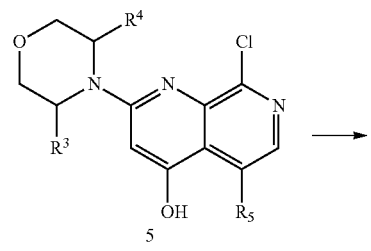

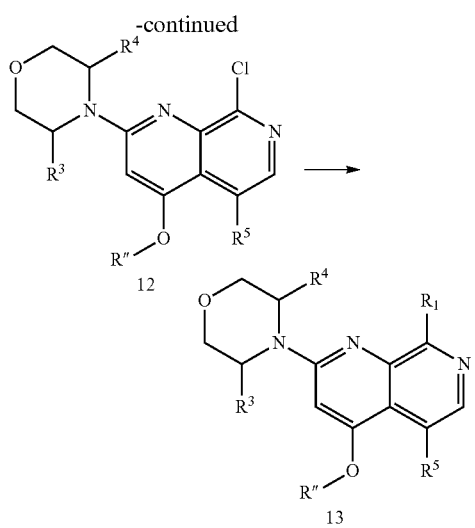

Step 5→12 (Scheme 3)
Conversion of Hydroxy to Ethers

Hydroxy-naphthyridines of formula 5 can be converted to the corresponding ether of general formula 13, in which R″ is $C_1$-$C_6$-alkyl or 3- to 10-membered heterocycloalkyl. The reaction is performed using halides (preferably Cl, Br or I), tosylates, mesylates or triflates. This reaction is performed in a solvent such as for example acetonitrile, DMF or a 1:1 mixture of methanol and water. The reaction is performed in the presence of a base such as for example $CsCO_3$ or $K_2CO_3$. The reaction is performed at temperatures ranging from room temperature to the boiling point of the respective solvent. Furthermore, the reaction can be performed at temperatures above the boiling point under pressure. The reaction is preferably completed after 1 to 16 hours.

Alternatively, the ether of general formula 12 can be synthesized via a Mitsunobu reaction from an alcohol in the presence of a phosphine (such as for example triphenylphoshine) and an azodicarboxylate (e.g. diisopropyl azodicarboxylate) in a solvent such as for example THF.

Step 12→13 (Scheme 3)
Palladium Catalyzed Reaction with Boronic Acids

The chloronaphthyridines of formula 12 can be reacted with a boronic acid derivative $R^1$—$B(OR)_2$ to give a compound of formula 13. The boronic acid derivative may be a boronic acid (R═—H) or an ester of the boronic acid, e.g. its isopropyl ester (R═—$CH(CH_3)_2$), preferably an ester derived from pinacol in which the boronic acid intermediate forms a 2-aryl-4,4,5,5-tetramethyl-1,3,2-dioxaborolane (R—R═—$C(CH_3)_2$—$C(CH_3)_2$—). The NH groups of the heterocycle $R^1$ of the boronic acid derivatives may be masked by any suitable protecting group (see Green, Wuts, "*Protective groups in organic synthesis*" 1999, John Wiley & Sons and references cited therein). The corresponding protective group may be removed at any suitable step of the synthesis. Preferably THP (tetrahydropyranyl), BOC (tert-Butoxycarbonyl) or PMB (para-Methoxybenzyl) are used as protective groups during the synthesis.

The coupling reaction is catalyzed by palladium catalysts, e.g. by Pd(0) catalysts like tetrakis(triphenylphosphine)palladium(0) [$Pd(PPh_3)_4$], tris(dibenzylideneacetone)di-palladium(0) [$Pd_2(dba)_3$], or by Pd(II) catalysts like dichlorobis(triphenylphosphine)-palladium(II) [$Pd(PPh_3)_2Cl_2$], palladium(II) acetate and triphenylphosphine or by [1,1'-bis(diphenylphosphino)ferrocene]palladium dichloride.

The reaction is preferably carried out in a mixture of a solvent like 1,2-dimethoxyethane, dioxane, DMF, DME, THF, or isopropanol with water and in the presence of a base like potassium carbonate, sodium bicarbonate or potassium phosphate.

(review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (i.e. approx. 20° C.) to the boiling point of the respective solvent. Further on, the reaction can be performed at temperatures above the boiling point using pressure tubes and a microwave oven. The reaction is preferably completed after 1 to 36 hours of reaction time.

Scheme 3:

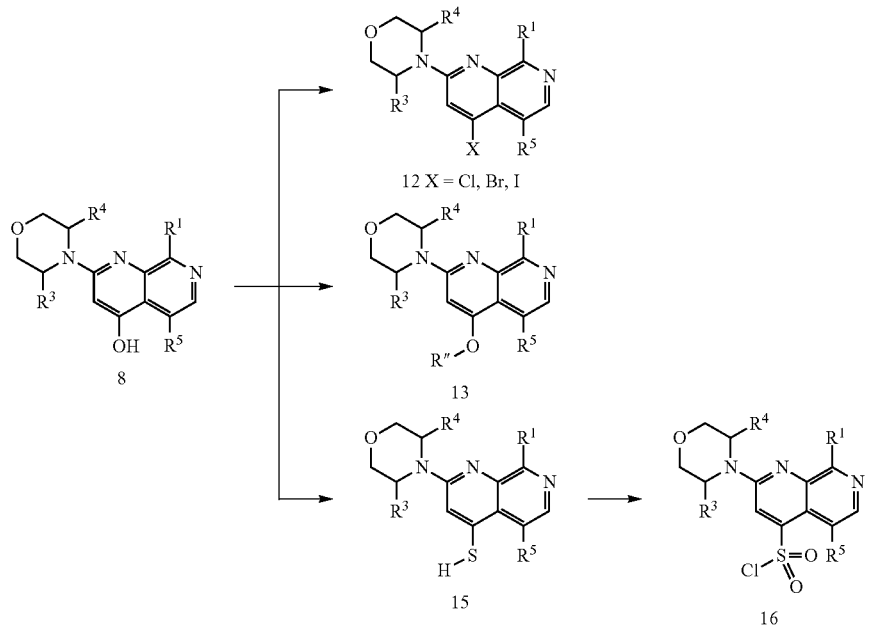

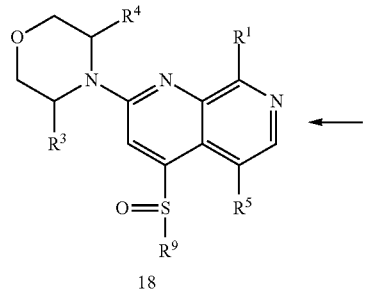 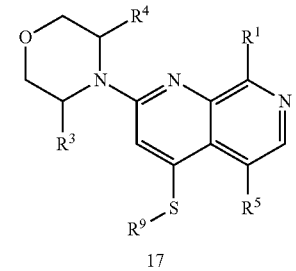 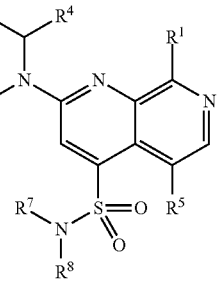

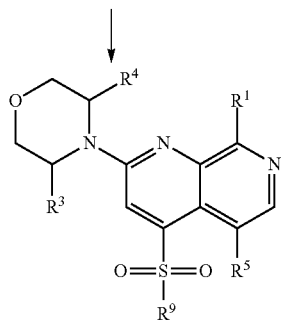

Route for the preparation of compounds of general formula 12, 13, 18, 19 and 20, wherein $R^1$, $R^3$, $R^4$, $R^5$, $R^7$, $R^8$ and $R^9$ have the meaning as given for general formula (I), supra and R" has the meaning as $C_1$—$C_6$-alkyl or 3-to 10-membered heterocycloalkyl. In addition, the substituents $R^1$ can bear a protecting group and the interconversion of any of the substituents $R^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

Step 8→12 (Scheme 3)
Conversion of Hydroxy to Halogen (F, Br, Cl, I)

The transformation of hydroxy-naphthyridine 8 to a halogen compound of formula 12 can be performed (for halogen=Cl) for example using chlorinating reagents such as trichlorophosphate with or without an organic solvent. Typically the reactions are performed at elevated temperatures. For halogen=Br reagents such as phosphorus tribromide or phosphorus oxytribromide can be used. For halogen=F see for example *J. of Org. Chem.*, 2013, 78, 4184-4189. For halogen=I see for example *Journal of Organic Chemistry*, 2009, 74, 5111-5114 and references therein.

Step 8→13 (Scheme 3)
Conversion of Hydroxy to Ethers

Hydroxy-naphthyridines of formula 8 can be converted to the corresponding ether of general formula 13, in which R" is $C_1$-$C_6$-alkyl or 3- to 10-membered heterocycloalkyl. The reaction is performed using halides (preferably Cl, Br or I), tosylates, mesylates or triflates. This reaction is performed in a solvent such as for example acetonitrile, DMF or a 1:1 mixture of methanol and water. The reaction is performed in the presence of a base such as for example $CsCO_3$ or $K_2CO_3$. The reaction is performed at temperatures ranging from room temperature to the boiling point of the respective solvent. Furthermore, the reaction can be performed at temperatures above the boiling point under pressure. The reaction is preferably completed after 1 to 16 hours.

Alternatively, the ether of general formula 13 can be synthesized via a Mitsunobu reaction from an alcohol in the presence of a phosphine (such as for example triphenylphosphine) and an azodicarboxylate (e.g. diisopropyl azodicarboxylate) in a solvent such as for example THF.

Step 8→15 (Scheme 3)
Conversion of Hydroxy to Thiol

For the conversion of hydroxy-naphthyridines of formula 8 to thiols of formula 15 for example Lawesson's reagent or diphosphorus pentasulfide in an organic solvent can be used. Typically these reactions are run at elevated temperatures.

Step 15→20 (Scheme 3)
Conversion of Thiol to Sulfonamide

Thiols of general formula 15 can be converted to the corresponding sulfonamides 20 via the intermediate sulfonylchlorides of formula 16 in analogy to literature procedures. For example see *European J. of Medicinal Chemistry* 2013, 60, 42-50 and references therein.

Step 15→17 (Scheme 3)
Conversion of Thiol to Thioether

Thiols of formula 15 can be alkylated to the corresponding thioethers 17. The reaction is performed using alkyl halides (preferably Cl, Br or I), tosylates, mesylates, or triflates. This reaction is performed in a solvent such as for example acetonitrile, DMF or a 1:1 mixture of methanol and water. The reaction is performed in the presence of a base such as for example $CsCO_3$ or $K_2CO_3$. The reaction is performed at temperatures ranging from room temperature to the boiling point of the respective solvent. Furthermore, the reaction can be performed at temperatures above the boiling point under pressure. The reaction is preferably completed after 1 to 16 hours.

Step 17→18 (Scheme 3)
Conversion of Thioether to Sulfoxide

Thioethers of formula 17 can be oxidized to the corresponding sulfoxides 18. Typically an oxidizing reagent in an organic solvent is used (for example 3-chloro-benzenecarboperoxoic acid in dichloromethane).

Step 17→19 (Scheme 3)
Conversion of Thioether to Sulfone

Thioethers of general formula 17 can be oxidized to the corresponding sulfoxides 19. Typically an oxidizing reagent in an organic solvent is used (for example 3-chloro-benzenecarboperoxoic acid in dichloromethane).

Scheme 4:

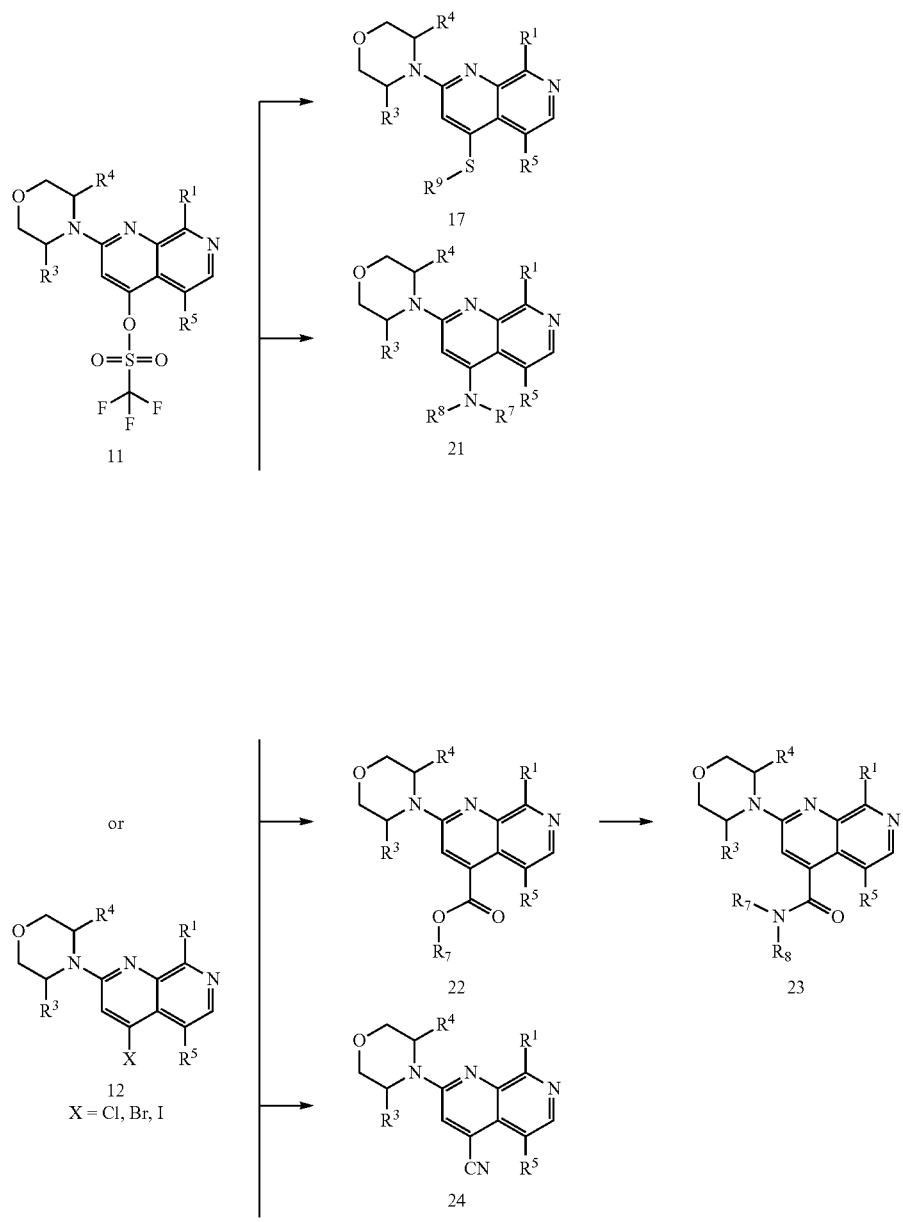

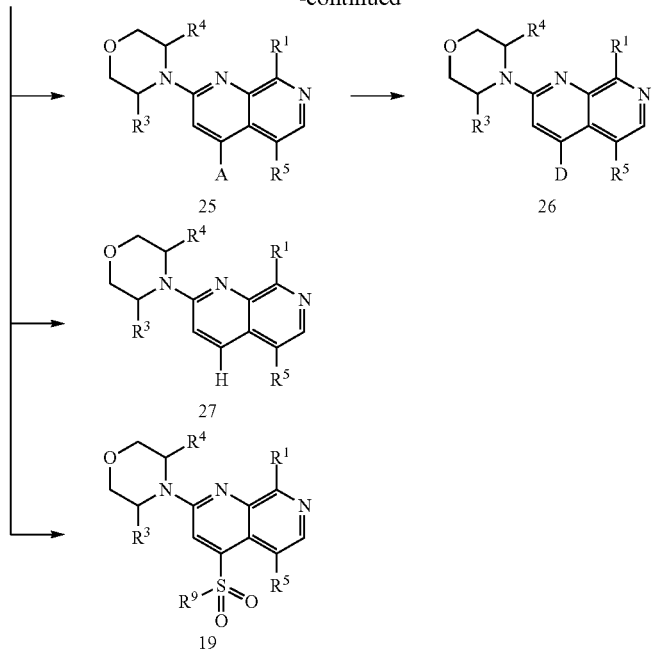

Route for the preparation of compounds of general formula 17, 19, 21, 23, 24, 26 and 27, wherein $R^1$, $R^3$, $R^4$, $R^5$, $R^7$, $R^8$ and $R^9$ have the meaning as given for general formula (I) supra. The group A represents $C_2$—$C_6$-alkenyl, $C_5$—$C_6$-cycloalkenyl, 4-to10-membered heterocycloalkenyl, aryl or heteroaryl and the group D represents $C_2$—$C_6$-alkyl, $C_5$—$C_6$-cycloalkyl, or 4-to 10-membered heterocycloalkyl. In addition, the substituents $R^1$ can bear a protecting group and the interconversion of any of the substituents $R^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

Step 12→17 (Scheme 4)
Conversion to Thioether

Halogen compounds of the general formula 12 can be converted to the corresponding thioethers of general formula 17 by nucleophilic substitution with thiols. Typically a base such as for example KOtBu, NaH, caesium carbonate, potassium carbonate in an organic solvent such as for example tert-butanol, DMSO or DMF are used. Typically the reaction is performed at elevated temperature. See for example: *Journal of Medicinal Chemistry*, 2008, 51, 3466-3479 and references therein.

Step 11 or 12→21 (Scheme 4)
C—N Cross Coupling Reaction or Nucleophilic Substitution Triflates of general formula 11 can be converted to the corresponding amines 21 by a C—N cross coupling reaction. Typically a metal catalyst, a ligand and a base in an organic solvent is used. For a recent review see for example: Chem. Soc. Rev., 2013, 42, 9283 or "*Metal-Catalyzed Cross-Coupling Reactions* (2 Volume Set)", 2004 by Armin de Meijere (Editor), François Diederich (Editor) and literature references therein.

Alternatively halogen compound of general formula 12 can be converted to the corresponding amines 21 via a nucleophilic substitution reaction. Typically nucleophilic amines in combination with a base (for example triethylamine, Hünig's base, potassium carbonate) in an organic solvent (for example iPrOH, DCM, DMSO, DMF) are used. See for example: *Bioorganic and Medicinal Chemistry Letters*, 2011, 21, 5502-5505 and references therein.

Step 11 or 12→22 (Scheme 4)
Hydrocarbonylation

Triflates of general formula 11 can be converted to the corresponding esters 22 by a metal catalyzed carbonylation reaction. Typically carbonmonoxide and a palladium catalyst with or without a ligand (for example: palladium acetate/1,3-bis-(diphenylphosphino)propane; bis-triphenyl-phosphine-palladium(II) chloride/triphenylphosphine), an alcohol as nucleophile (for example: methanol, ethanol) in an organic solvent (for example: DMF, methanol, ethanol) is used. See for example: *Journal of Medicinal Chemistry*, 2008, 51, 1649-1667 or *Synthesis*, 2001, 7, 1098-1109 and references therein.

Step 22→23 (Scheme 4)
Amide Formation

Esters of general formula 22 can be converted to the corresponding amides of general formula 23. Typically an amine is reacted in combination with a base (as for example sodium hydroxide or magnesium methanolate) in a solvent (as for example methanol, isopropanol, water). Alternatively the ester 22 can be reacted with an amine and n-butyllithium or trimethylaluminum in an organic solvent (such as for example THF, toluene) to form amides of formula 23. See for example *Chem. Commun.*, 2008, 1100-1102 and references therein.

Alternatively the ester of general formula 22 can be hydrolyzed to the corresponding carboxylic acid (using for example KOH, water, methanol as ester hydrolysis conditions) and reacted further to the corresponding amides 23 under classical amide coupling conditions. For a review for amide coupling conditions using the free carboxylic acid and an amine in combination with an activating agent see for example *Chem. Soc. Rev.*, 2009, 38, 606-631 and references therein.

Step 11 or 12→24 (Scheme 4)
Nitrile Formation

Halogen comounds of general formula 12 or triflates of general formula 11 can be converted to the corresponding nitriles 24. Typically a palladium catalyst and a ligand (such as for example 1,1'-bis-(diphenylphosphino)ferrocene/tris-(dibenzylideneacetone)dipalladium(0)), zinc (II) cyanide in solvent (such as for example N,N-dimethyl acetamide/water) is used. See for example *Tetrahedron Letters,* 2006, 47, 3303-3305 and references therein.

Step 11 or 12→25 (Scheme 4)
C—C Cross Coupling Reaction

Triflates of general formula 11 can be reacted with a boronic acid derivative A-B(OR)$_2$ to give a compound of formula 25. The group A represents $C_1$-$C_6$-alkyl, $C_2$-$C_6$-alkenyl, $C_3$-$C_6$-cycloalkyl, 3- to 10-membered heterocycloalkyl, 4- to 10-membered heterocycloalkenyl, phenyl, heteroaryl. The boronic acid derivative may be a boronic acid (R═—H) or an ester of the boronic acid, e.g. its isopropyl ester (R═—CH(CH$_3$)$_2$), preferably an ester derived from pinacol in which the boronic acid intermediate forms a 2-aryl-4,4,5,5-tetramethyl-1,3,2-dioxaborolane (R—R═—C(CH$_3$)$_2$—C(CH$_3$)$_2$—). The group A of the boronic acid derivatives may be masked by any suitable protecting group (see Green, Wuts, *"Protective groups in organic synthesis"* 1999, John Wiley & Sons). The corresponding protective group may be removed at any suitable step of the synthesis.

The coupling reaction is catalyzed by palladium catalysts, e.g. by Pd(0) catalysts like tetrakis(triphenylphosphine)palladium(0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride.

The reaction is preferably carried out in a mixture of a solvent like 1,2-dimethoxyethane, dioxane, DMF, DME, THF, or isopropanol with water and in the presence of a base like potassium carbonate, sodium bicarbonate or potassium phosphate.

(review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature to the boiling point of the solvent. Further on, the reaction can be performed at temperatures above the boiling point under pressure. The reaction is preferably completed after 1 to 36 hours.

Step 25→26 (Scheme 4)
Hydrogenation of Double Bond

Unsaturated derivatives of formula 25 (wherein the group A represents $C_2$-$C_6$-alkenyl, $C_5$-$C_6$-cycloalkenyl, 4- to 10-membered heterocycloalkenyl). can be hydrogenated to the corresponding saturated derivatives of general formula 26 (wherein the group D represents $C_2$-$C_6$-alkyl, $C_5$-$C_6$-cycloalkyl, 4- to 10-membered heterocycloalkyl). Typically hydrogen (at atmospheric or elevated pressure) is used in combination with a heterogeneous or homogeneous catalyst such as for example palladium on charcoal in an organic solvent such as ethyl acetate, methanol or acetic acid.

Step 12→27 (Scheme 4)
Dehalogenation Reaction

Halides of general formula 12 can be dehalogenated for example by a hydrogenation reaction to obtain naphthyridines of general formula 27. Typically hydrogen (at atmospheric or elevated pressure), a base as for example triethylamine and a heterogeneous metal catalyst such as for example palladium on activated carbon in an organic solvent such as for example ethanol, ethyl acetate, acetic acid is used.

Step 11 or 12→19 (Scheme 4)
Sulfonylation Reaction

A halide of general formula 12 or a triflate of general formula 11 can be converted to the corresponding sulfone of general formula 19 by reaction with an alkyl sulfinic acid sodium salt or aryl sulfinic acid sodium salt with a base such as for example 4-(N,N-dimethlyamino)pyridine or pyridine in an organic solvent as for example N,N-dimethyl-formamide. Typically the reaction is performed at elevated temperature. The reaction can also be mediated by copper (see for example *European Journal of Medicinal Chemistry,* 2004, vol. 39, 735-744).

Scheme 5:

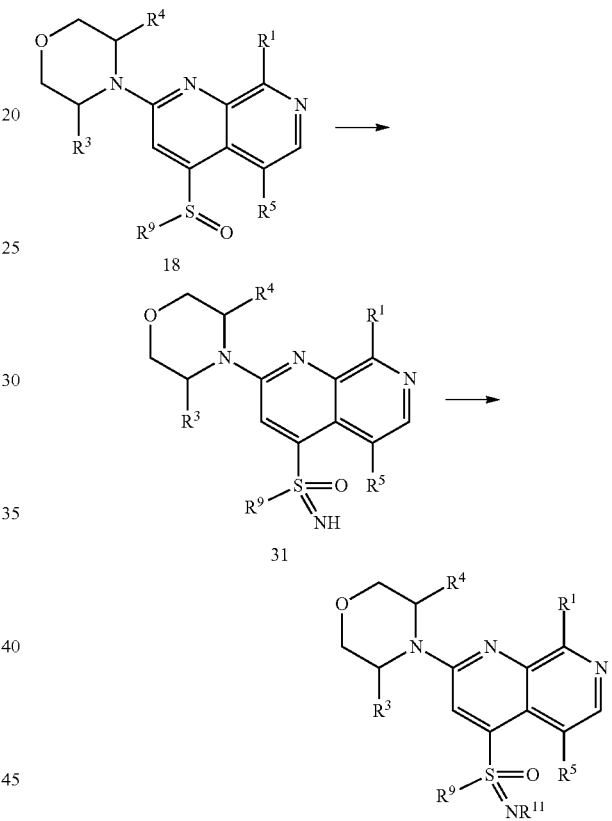

Route for the preparation of compounds of general formula 38, wherein $R^1$, $R^3$, $R^4$, $R^5$, $R^9$ and $R^{11}$ have the meaning as given for general formula (I), supra. In addition, the substituents $R^1$ can bear a protecting group and the interconversion of any of the substituents $R^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

Step 18→31 (Scheme 5)
Sulfoximine Formation

Sulfoxide 18 is converted to the corresponding sulfoximine 31 in a two step procedure. Typically, the sulfoxide 18 is converted to a protected sulfoximine intermediate using a described procedure (*Org. Lett.,* 2004, 6, 1305-1307 and references therein). Deprotection to the sulfoximine 31 is performed using a base such as for example K$_2$CO$_3$ in methanol. Additional options to convert the sulfoxide 18 to an unprotected sulfoximine 31 are the use of hydrazoic acid prepared in situ (e.g. *ChemMedChem,* 2013, 8, 1021) or the use of O-(mesitylenesulfonyl)hydroxylamine (MSH) (e.g. *J. Org. Chem.,* 1973, 38, 1239.

Step 31→38 (Scheme 5)

Functionalization of the Sulfoximine Nitrogen

Functionalization of the nitrogen of sulfoximines of general formula 31 can be performed using previously described methods: N-unprotected sulfoximines of formula 31 may be reacted to give N-functionalized derivatives of formula 38. There are multiple methods for the preparation of N-functionalized sulfoximines by functionalization of the nitrogen of the sulfoximine group:

- Alkylation: see for example: a) U. Lücking et al, US 2007/0232632; b) C. R. Johnson, J. Org. Chem. 1993, 58, 1922; c) C. Bolm et al, Synthesis 2009, 10, 1601.
- Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.
- Reaction with chloroformiates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al,
- Reaction with bromocyane: see for example: a) D. T. Sauer et al, Inorganic Chemistry 1972, 11, 238; b) C. Bolm et al, Org. Lett. 2007, 9, 2951; c) U. Lücking et al, WO 2011/29537.

Scheme 6:

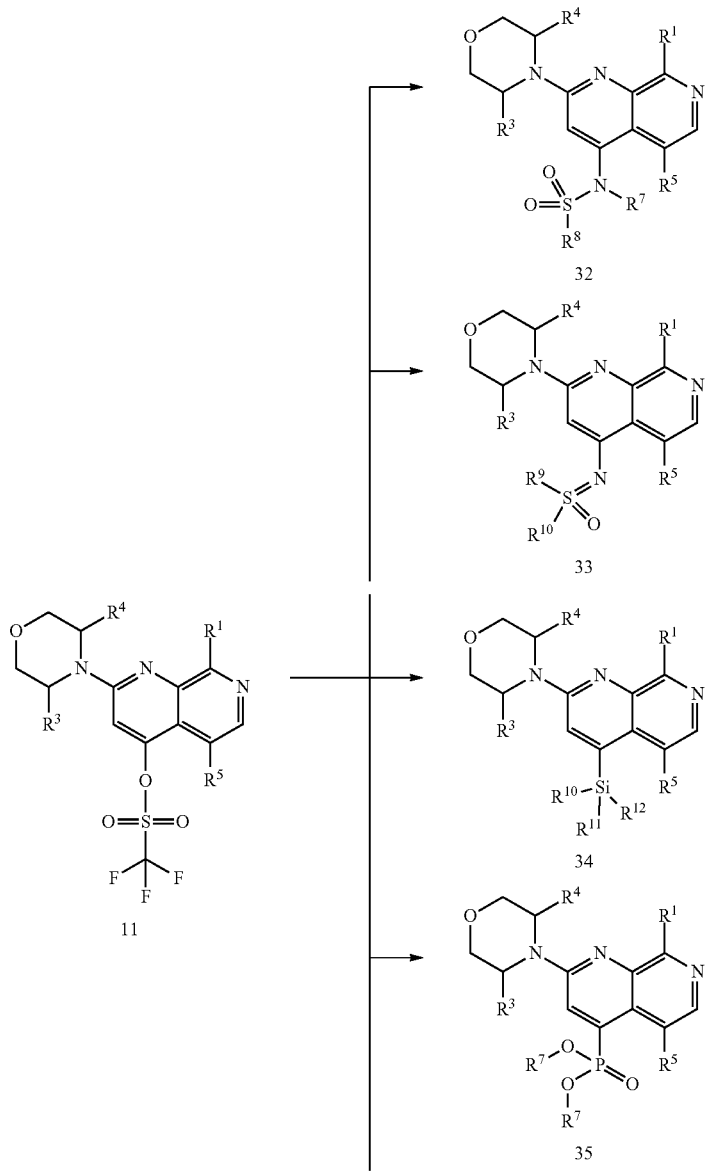

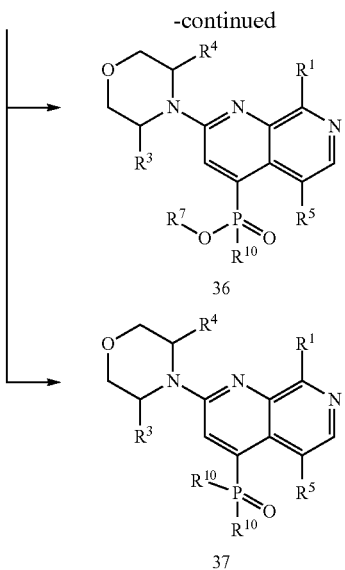

36

37

Route for the preparation of compounds of general formula 32, 33, 34, 35, 36 and 37, wherein $R^1$, $R^3$, $R^4$, $R^5$, $R^7$, $R^8$, $R^9$, $R^{10}$, $R^{11}$ and $R^{12}$ have the meaning as given for general formula (I), supra. In addition, the substituents $R^1$ can bear a protecting group and the interconversion of any of the substituents $R^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

Step 11→32 (Scheme 6)

A triflate of general formula 11 can be converted to the corresponding sulfonamide 32 under palladium catalysis in analogy to literature procedures. For example see *J. Am. Chem. Soc.*, 2009, 131, 16720-16734 and references therein.

Step 11→33 (Scheme 6)

A triflate of general formula 11 can be converted to the corresponding sulfoximines 33 under palladium catalysis in analogy to literature procedures. For example see US2001/144345.

Step 11→34 (Scheme 6)

A triflate of general formula 11 can be converted to the corresponding sililated compound 34 under palladium catalysis in analogy to literature procedures. For example see *Org. Lett.* 2007, 9, 3785-3788 and references therein.

Step 11→35 (Scheme 6)

A triflate of general formula 11 can be converted to the phosphonate 35 under palladium catalysis in analogy to literature procedures. For example see US2008/9465

Step 11→36 (Scheme 6)

A triflate of general formula 11 can be converted to the phosphinate 36 under palladium catalysis in analogy to literature procedures. For example see *Adv. Synth. Cat.*, 2013, 355, 1361-1373 and references therein.

Step 11→37 (Scheme 6)

A triflate of general formula 11 can be converted to the phosphine oxide 37 under palladium catalysis in analogy to literature procedures. For example see US2007/4648

EXPERIMENTAL SECTION

The following table lists the abbreviations used in this paragraph, and in the examples section.

Boc tert-butyloxycarbonyl
BuLi Butyllithium
conc. concentrated
DCE Dichloroethane
DCM Dichloromethane
DMAP N,N-Dimethylaminopyridine
DME Dimethoxyethane
DMF Dimethylformamide
DMSO Dimethyl sulfoxide
EA Ethyl acetate
EtOAc Ethyl acetate
EtOH Ethanol
HPLC, LC high performance liquid chromatography
h hour
LiHMDS Lithium bis(trimethylsilyl)amide
KHMDS Potassium bis(trimethylsilyl)amide
KOtBU Potassium tert-butoxide
min minute
LCMS, LC-MS, LC/MS Liquid chromatography-mass spectrometry
LDA Lithium diisopropylamide
MS mass spectroscopy
NMR nuclear magnetic resonance
NMO N-metylmorpholine-N-oxide
NaHMDS Sodium bis(trimethylsilyl)amide
PE Petrol ether
Pd(dppf)Cl$_2$ [1,1'-Bis-diphenylphosphino-ferrocene]palladium(II) dichloride
Rac Racemate
$R_f$ Retardation factor
$R_t$ Retention time
sat. saturated
rt, RT Room temperature
TFA Trifluoroacetic acid
THF Tetrahydrofuran
TLC thin-layer chromatography Chemical names were generated using ACD/Name Batch Version 12.01 or Autonom 2000.

All reagents, for which the synthesis is not described in the experimental part, are either commercially available or synthesized as described in literature references.

Analytical Methods

LC-MS Method 1:

column: Ascentis Express C18, 2.7 µm, 3 cm×2.1 mm
column temp.: 30° C.
injection volume: 1 µl
detection: MM-ES+APCI+DAD (254 nm)
fragment.potential: 50 V
mass range: 80-800 m/z
mobile phase A: water/0.1% formic acid
mobile phase B: methanol/0.1% formic acid
system time delay: 0.2 min
gradient:

| time in min | % A | % B | flow rate in ml/min |
|---|---|---|---|
| 1.0 | 95 | 5 | 0.8 |
| 4.0 | 0 | 100 | 0.8 |
| 5.0 | 0 | 100 | 0.8 |
| 6.0 | 95 | 5 | 0.8 |
| 6.5 | 95 | 5 | 0.8 |

LC-MS Method 2:

MS instrument type: Micromass Quatro Micro; HPLC instrument type: Agilent 1100 Series; UV DAD; column: Chromolith Flash RP-18E 25-2 mm; mobile phase A: 0.0375% TFA in water, mobile phase B: 0.01875% TFA in acetonitrile; gradient: 0.0 min 100% A→1.0 min 95% A→3.0 min 95% A→3.5 min 5% A→3.51 min 5% A→4.0 min 95% A; flow rate: 0.8 ml/min; column temp: 50° C.; UV detection: 220 nm & 254 nm.

LC-MS Method 3:
System: MS (LBA639)
Binary Solvent Manager
Sample Manager
Organizer
Column Manger
PDA
ELSD
Injection volume: 1 µl
Column: Acquity UPLC BEH C18 1.7 50×2.1 mm
Eluent A1: H2O+0.1% Vol. HCOOH (99%)
A2: H2O+0.2% Vol. NH3 (32%)
B1: Acetonitril
Flow rate: 0.8 ml/min
Temperature: 60° C.
Eluent Gradient A1+B1: 0-1.6 min 1-99% B1; 1.6-2.0 min 99% B1

LC-MS Method 4:

Instrument MS: Waters ZQ; Instrument HPLC: Waters UPLC Acquity; Column: Acquity BEH C18 (Waters), 50 mm×2.1 mm, 1.7 µm; eluent A: water+0.1 vol % formic acid, eluent B: acetonitrile (Lichrosolv Merck); gradient: 0.0 min 99% A-1.6 min 1% A-1.8 min 1% A-1.81 min 99% A-2.0 min 99% A; temperature: 60° C.; flow: 0.8 mL/min; UV-Detection PDA 210-400 nmnm-plus fixed wavelength 254 nm; MS ESI (+), Scan region 170-800 m/z LC-MS Method 5:

System: UPLC Acquity (Waters) with PDA Detector and Waters ZQ mass spectrometer; Column: Acquity BEH C18 1.7 µm 2.1×50 mm; Temperature: 60° C.; Solvent A: Water+ 0.1% Formic Acid; Solvent B: Acetonitrile; Gradient: 99% A to 1% A (1.6 min) to 1% A (0.4 min); Flow: 0.8 mL/min; Injektion Volume: 1.0 µl (0.1 mg-1 mg/mL Sample Concentration); Detection: PDA Scan Region 210-400 nm-plus fixed wavelength 254 nm; MS ESI (+), Scan region 170-800 m/z Preparative HPLC Autopurifier: Acidic Conditions

| System: | Waters Autopurificationsystem: Pump 2545, Sample Manager 2767, CFO, DAD 2996, ELSD 2424, SQD |
|---|---|
| Column: | XBrigde C18 5 µm 100 × 30 mm |
| Solvent: | A = H₂O + 0.1% Vol. HCOOH (99%) B = MeCN |
| Gradient: | 0.00-0.50 min 5% B, 25 ml/min 0.51-5.50 min 10-100% B, 70 ml/min 5.51-6.50 min 100% B, 70 mL/min |
| Temperature: | RT |
| Solution: | max. 250 mg/max. 2.5 mL DMSO or DMF |
| Injection: | 1 × 2.5 ml |
| Detection: | DAD scan range 210-400 nm MS ESI+, ESI−, scan range 160-1000 m/z |

Autopurifier: Basic Conditions

| System: | Waters Autopurificationsystem: Pump 2545, Sample Manager 2767, CFO, DAD 2996, ELSD 2424, SQD |
|---|---|
| Column: | XBrigde C18 5 µm 100 × 30 mm |
| Solvent: | A = H₂O + 0.2% Vol. NH₃ (32%) B = MeCN |
| Gradient: | 0.00-0.50 min 5% B, 25 ml/min 0.51-5.50 min 10-100% B, 70 ml/min 5.51-6.50 min 100% B, 70 ml/min |
| Temperature: | RT |
| Solution: | max. 250 mg/max. 2.5 mL DMSO or DMF |
| Injection: | 1 × 2.5 ml |
| Detection: | DAD scan range 210-400 nm MS ESI+, ESI−, scan range 160-1000 m/z |

Preparation of Intermediates

Intermediate-1

Step a methyl 3-[(tert-butoxycarbonyl)amino]-2-chloro-5-methylisonicotinate

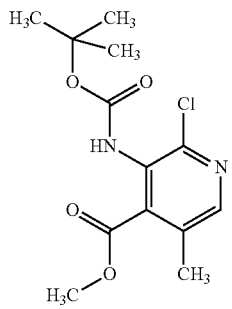 [SMILES: COC(=O)c1c(C)cnc(Cl)c1NC(=O)OC(C)(C)C]

A solution of trimethylsilyldiazomethane in diethyl ether (2M; 0.35 mL; 0.7 mmol) was added dropwise to a stirred solution of 3-[(tert-butoxycarbonyl)amino]-2-chloro-5-methylisonicotinic acid (100 mg; 0.35 mmol) in THF (1.30 mL) and MeOH (0.14 mL) at 0° C. The mixture was stirred overnight, slowly coming to RT. The mixture was diluted wit EE, washed with an aqueous solution of sodium chloride, filtered using a Whatman filter and concentrated to give the crude product (106 mg) that was used without further purification.

¹H NMR (400 MHz, DMSO): δ [ppm]=1.42 (9H), 2.28 (3H), 3.83 (3H), 8.27 (1H), 9.21 (1H).

Step b methyl 3-amino-2-chloro-5-methylisonicotinate hydrochloride

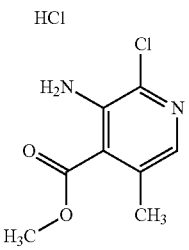

A solution of HCl in dioxane (4N; 56.5 mL; 226 mmol) was added to a solutuion of crude methyl 3-[(tert-butoxycarbonyl)amino]-2-chloro-5-methylisonicotinate (5.10 g) in DCM (172 mL) and MeOH (17 mL). The mixture was stirred for 90 minutes at RT and concentrated. Co-evaporation with DCM (3×) gave the crude product (3.56 g) that was used without further purification.

$^1$H NMR (400 MHz, DMSO): δ [ppm]=2.22 (3H), 3.88 (3H), 5.99 (2H), 7.50-7.57 (1H).

Step c

1-[(3R)-3-methylmorpholin-4-yl]ethanone

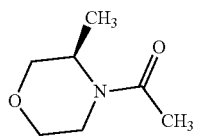

Acetic anhydride (14.0 mL; 148 mmol) was added dropwise to a stirred solution of (3R)-3-methylmorpholine (1.50 g; 14.8 mmol) in pyridine (36 mL) at RT. The reaction was stirred at RT for 72 hours and concentrated. Co-evaporation with toluene (3×) gave the desired crude product (2.27 g) that was used without further purification.

Step d methyl 2-chloro-5-methyl-3-[(E)-{1-[(3R)-3-methylmorpholin-4-yl]ethylidene}amino]isonicotinate

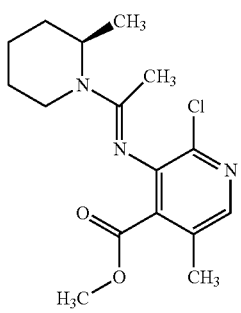 [SMILES: COC(=O)c1c(C)cnc(Cl)c1/N=C(\C)N1CCCC[C@H]1C]

Under argon, phosphorus oxychloride (7.60 g; 49.6 mmol) was added dropwise to a stirred solution of 1-[(3R)-3-methylmorpholin-4-yl]ethanone (4.95 g; 34.5 mmol) in DCE (22 mL) at 0° C. The mixture was stirred at RT for 30 minutes before crude methyl 3-amino-2-chloro-5-methylisonicotinate hydrochloride (3.56 g; 15.0 mmol) was added. The mixture was stirred at 80° C. for 2 hours. The mixture was added under stirring to a mixture of ice water and aqueous sodium bicarbonate solution. The mixture was stirred until the temperature reached RT. The mixture was extracted with DCM, filtered using at Whatman filter and concentrated. The residue was purified by column chromatography on silica gel (hexane to hexane/ethyl acetate 60%) to give the desired product (3.15 g; 9.7 mmol).

$^1$H NMR (400 MHz, DMSO): δ [ppm]=1H-NMR (400 MHz, DMSO-d6): Shift [ppm]=1.18 (3H), 1.74 (3H), 2.18 (3H), 3.06-3.22 (1H), 3.37-3.44 (1H), 3.50-3.59 (1H), 3.63-3.80 (m, 5H), 3.86 (1H), 4.15-4.35 (1H), 7.91 (s, 1H).

Step e 8-chloro-5-methyl-2-[(3R)-3-methylmorpholin-4-yl]-1,7-naphthyridin-4-ol

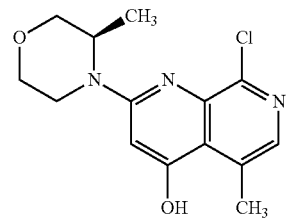 [SMILES: Cc1cnc(Cl)c2nc(N3CCOC[C@H]3C)cc(O)c12]

Under argon, a solution of of lithium bis(trimethylsilyl)amide in THF (1M; 29.0 mL, 29.0 mmol) was added dropwise to a stirred solution of methyl 2-chloro-5-methyl-3-[(E)-{1-[(3R)-3-methylmorpholin-4-yl]ethylidene}amino]isonicotinate (3.15 g; 9.7 mmol) in THF (120 mL) at 0° C. The mixture was stirred overnight, slowly warming to RT. The mixture was cooled to 0° C. and ice water was added under stirring. The pH was adjusted to 5.5 by the addition of HCl (2N). Solid NaCl was added before the mixture was extracted with EE/THF (1:1). The organic phase was filtered using a Whatman filter and concentrated. The residue was purified by column chromatography on silica gel (hexane/ethyl acetate 30% to 50%) to give the desired product (1.20 g; 4.1 mmol). $^1$H NMR (400 MHz, DMSO): δ [ppm]=1.20 (3H), 2.63 (3H), 3.11-3.30 (1H), 3.39-3.54 (1H), 3.65 (1H), 3.77 (1H), 3.98 (1H), 4.11 (1H), 4.34 (1H), 6.54 (1H), 7.72 (1H).

Intermediate-2

8-chloro-4-isopropoxy-5-methyl-2-[(3R)-3-methylmorpholin-4-yl]-1,7-naphthyridine

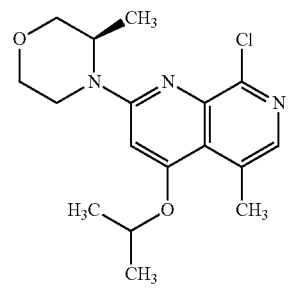 [SMILES: Cc1cnc(Cl)c2nc(N3CCOC[C@H]3C)cc(OC(C)C)c12]

Potassium carbonate (141 mg; 1.02 mmol) was added to a stirred solution of 8-chloro-5-methyl-2-[(3R)-3-methylmorpholin-4-yl]-1,7-naphthyridin-4-ol (200 mg; 0.68 mmol) in MeCN (11 mL) followed by 2-iodopropane (289 mg; 1.70 mmol). The mixture was stirred at 60° C. overnight. After cooling the mixture was diluted with EE, washed with aqueous sodium chloride solution, filtered using a Whatman filter and concentrated to give the crude product (247 mg) that was used without further purification.

1H NMR (400 MHz, DMSO): δ [ppm]=1.21 (3H), 1.40 (6H), 2.60 (3H), 3.13-3.23 (1H), 3.36-3.55 (1H), 3.66 (1H), 3.78 (1H), 3.95-4.04 (1H), 4.23-4.31 (1H), 4.60 (1H), 5.03 (1H), 6.70 (1H), 7.74 (1H).

Intermediate-3

5-methyl-2-[(3R)-3-methylmorpholin-4-yl]-8-{1-[tetrahydro-2H-pyran-2-yl]-1H-pyrazol-5-yl}-1,7-naphthyridin-4-ol

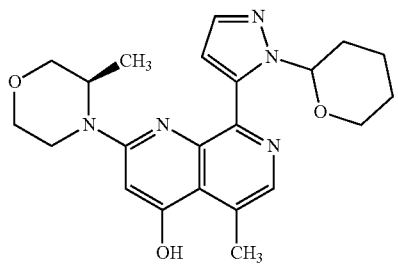 [SMILES: Cc1cnc(-c2ccnn2C2CCCCO2)c2nc(N3CCOC[C@H]3C)cc(O)c12]

Under argon, a mixture of 8-chloro-4-isopropoxy-5-methyl-2-[(3R)-3-methylmorpholin-4-yl]-1,7-naphthyridine (300 mg; 1.02 mmol), 1-(tetrahydro-2H-pyran-2-yl)-5-(4,4,5,5-tetramethyl-1,3,2-dioxaborolan-2-yl)-1H-pyrazole (426 mg; 1.53 mmol), [1,1'-bis(diphenylphosphino)ferrocene]dichloropalladium(II), complex with dichloromethane (83 mg; 0.10 mmol) and caesium carbonate (525 mg; 1.61 mmol) in dioxane (2.7 mL) was stirred at 80° C. for 150 min. After cooling, the mixture was diluted with DCM. Saturated aqueous ammonium chloride solution was added and the mixture was stirred for 10 min. The organic phase was filtered using a Whatman filter and concentrated. The residue was purified by column chromatography on silica gel (ethyl acetate) to give the desired product (369 mg; 0.90 mmol).

1H-NMR (400 MHz, DMSO): δ [ppm]=1.17 (5H), 1.39-1.61 (2H), 2.30-2.40 (1H), 2.71 (3H), 3.04-3.15 (1H), 3.19-3.31 (1H), 3.38-3.50 (1H), 3.60 (1H), 3.67-3.77 (2H), 3.83-4.06 (3H), 4.14-4.30 (1H), 5.89-5.99 (1H), 6.54 (1H), 6.77 (1H), 7.57 (1H), 8.07 (1H), 11.38 (1H).

Intermediate-4

5-methyl-2-[(3R)-3-methylmorpholin-4-yl]-8-{1-[tetrahydro-2H-pyran-2-yl]-1H-pyrazol-5-yl}-1,7-naphthyridin-4-yl trifluoromethanesulfonate

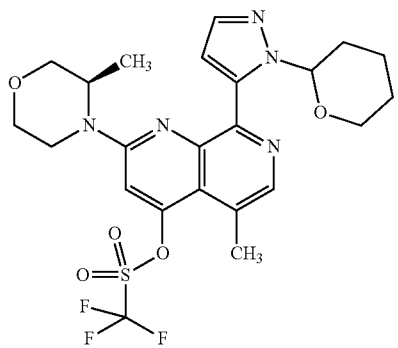 [SMILES: Cc1cnc(-c2ccnn2C2CCCCO2)c2nc(N3CCOC[C@H]3C)cc(OS(=O)(=O)C(F)(F)F)c12]

Under argon, N,N-diisopropyl ethylamine (0.17 mL; 0.98 mmol) was added to a stirred mixture of 5-methyl-2-[(3R)-3-methylmorpholin-4-yl]-8-{1-[tetrahydro-2H-pyran-2-yl]-1H-pyrazol-5-yl}-1,7-naphthyridin-4-ol (200 mg; 0.49 mmol) and 1,1,1-trifluoro-N-phenyl-N-[(trifluoromethyl)sulfonyl]methanesulfonamide (195 mg; 0.55 mmol) in DCM (2.8 mL). The mixtures was stirred for 2 h at RT before it was concentrated. The residue was purified by column chromatography on silica gel (hexane to hexane/ethyl acetate 50%) to give the desired product (228 mg; 0.42 mmol).

1H-NMR (400 MHz, DMSO): δ [ppm]=1.16-1.26 (3H), 1.40-1.63 (3H), 1.90-2.02 (2H), 2.30-2.41 (1H), 2.70 (3H), 3.18-3.30 (2H), 3.38-3.52 (1H), 3.59-3.80 (3H), 3.94-4.09 (2H), 4.40 (1H), 5.91-5.98 (1H), 6.84 (1H), 7.42 (1H), 7.62 (1H), 8.32 (1H).

Intermediate-5 methyl 5-methyl-2-[(3R)-3-methylmorpholin-4-yl]-8-{1-[(tetrahydro-2H-pyran-2-yl]-1H-pyrazol-5-yl}-1,7-naphthyridine-4-carboxylate

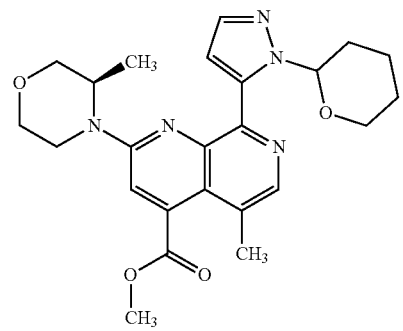 [SMILES: COC(=O)c1cc(N2CCOC[C@H]2C)nc2c(-c3ccnn3C3CCCCO3)ncc(C)c12]

In an autoclave, a mixture of 5-methyl-2-[(3R)-3-methylmorpholin-4-yl]-8-{1-[tetrahydro-2H-pyran-2-yl]-1H-pyrazol-5-yl}-1,7-naphthyridin-4-yl trifluoromethanesulfonate (1000 mg; 1.85 mmol), 1,3-bis(diphenylphosphino)propane (79 mg; 0.19 mmol), palladium(II) acetate (41 mg; 0.19 mmol) and triethylamine (0.5 mL) in DMF (13 mL) and methanol (7 mL) was purged with carbon monoxide at room temperature. The autoclave was pressured with carbonmonoxide to 13.8 bar and the mixture was stirred at room temperature for 30 minutes. The autoclave was depressurized and then pressured with carbon monoxide to 15.5 bar. The mixture was stirred at 80° C. for 21 hours. The autoclave was depressurized and after cooling, the mixture was diluted with an aqueous solution of sodium chloride and extracted with ethyl acetate (2×). The combined organic phases were dried (Na$_2$SO$_4$), filtered and concentrated. The residue was purified by column chromatography (gradient from Hex/EtOAc 505 to 100% EtOAc) to give the desired product (350 mg; 0.78 mmol).

$^1$H-NMR (400 MHz, DMSO-d6): δ [ppm]=1.13-1.30 (4H), 1.38-1.63 (3H), 1.89-2.01 (2H), 2.32-2.46 (4H), 3.14-3.31 (2H), 3.35-3.50 (1H), 3.57-3.78 (3H), 3.92-4.16 (5H), 4.46 (1H), 5.87-5.98 (1H), 6.80 (1H), 7.61 (1H), 8.27 (1H).

Example 1

5-methyl-2-[(3R)-3-methylmorpholin-4-yl]-4-(propan-2-yloxy)-8-(1H-pyrazol-5-yl)-1,7-naphthyridine

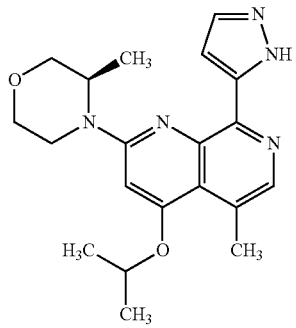 [SMILES: Cc1cnc(-c2ccn[nH]2)c2nc(N3CCOC[C@H]3C)cc(OC(C)C)c12]

Under argon, bis(triphenylphosphine)palladium(II) dichloride (21 mg; 0.03 mmol) was added to a mixture of 8-chloro-4-isopropoxy-5-methyl-2-(3-methylmorpholin-4-yl)-1,7-naphthyridine (100 mg; 0.30 mmol), 1-(tetrahydro-2H-pyran-2-yl)-5-(4,4,5,5-tetramethyl-1,3,2-dioxaborolan-2-yl)-1H-pyrazole (248 mg; 0.89 mmol) and potassium carbonate (123 mg; 0.89 mmol) in DME (0.8 mL) and water (0.4 mL). The mixture was stirred at 130° C. for 10 minutes in a microwave oven. After cooling, the reaction mixture was diluted with EE and filtered using a Whatman filter and concentrated.

The residue was dissolved in MeOH (3.2 mL) and an aqueous solution of hydrogen chloride (2N; 0.8 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (9 mg; 0.02 mmol).

$^1$H-NMR (400 MHz, DMSO-d6): δ [ppm]=1.25 (3H), 1.42 (6H), 2.69 (3H), 3.15-3.31 (1H), 3.56 (1H), 3.71 (1H), 3.82 (1H), 4.04 (1H), 4.11 (1H), 4.56 (1H), 5.04 (1H), 6.74 (1H), 7.27 (1H), 7.57 (1H), 8.07 (1H), 13.29 (1H).

Example 2

5-methyl-2-[(3R)-3-methylmorpholin-4-yl]-4-(1-methyl-1H-pyrazol-5-yl)-8-(1H-pyrazol-5-yl)-1,7-naphthyridine

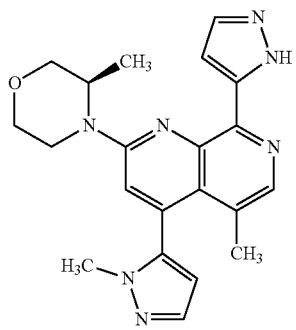 [SMILES: Cc1cnc(-c2ccn[nH]2)c2nc(N3CCOC[C@H]3C)cc(-c3ccnn3C)c12]

A suspension of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (110 mg; 0.20 mmol), 1-methyl-5-(4,4,5,5-tetramethyl-1,3,2-dioxaborolan-2-yl)-1H-pyrazole (42 mg; 0.20 mmol), [1,1'-bis(diphenylphosphino)ferrocene]dichloropalladium(II) complex with dichloromethane (1:1, Pd(dppf)Cl$_2$; 17 mg; 0.02 mmol)) and potassium carbonate (70 mg; 0.51 mmol) in MeCN (4.2 mL) and water (1.4 mL) was degased with argon. Under argon, the reaction mixture was stirred at 130° C. for 10 minutes in a microwave reactor. After cooling the reaction mixture was diluted with EE and washed with saturated aqueous sodium chloride solution. The organic phase was filtered using a Whatman filter and then concentrated.

The residue was dissolved in MeOH (1.5 mL) and an aqueous solution of hydrogen chloride (2N; 0.4 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (10 mg; 0.03 mmol).

$^1$H-NMR (400 MHz, DMSO-d6): δ [ppm]=1.24-1.33 (3H), 1.80 (3H), 3.48-3.62 (4H), 3.64-3.75 (1H), 3.81 (1H), 4.03 (1H), 4.19 (1H), 4.60 (1H), 6.48 (1H), 7.34 (1H), 7.42 (1H), 7.59 (1H), 7.62 (1H), 8.16 (1H), 13.36 (1H).

Example 3

4-(2-fluoropyridin-3-yl)-5-methyl-2-[(3R)-3-methylmorpholin-4-yl]-8-(1H-pyrazol-5-yl)-1,7-naphthyridine

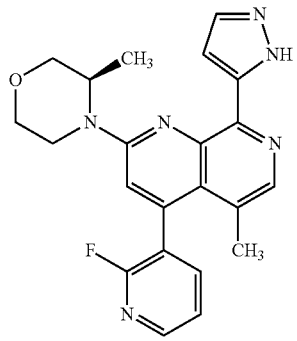 [SMILES: Cc1cnc(-c2ccn[nH]2)c2nc(N3CCOC[C@H]3C)cc(-c3cccnc3F)c12]

A suspension of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (110 mg; 0.20 mmol), (2-fluoropyridin-3-yl)boronic acid (29 mg; 0.20 mmol), [1,1'-bis(diphenylphosphino)ferrocene]-dichloropalladium(II) complex with dichloromethane (1:1, Pd(dppf)Cl$_2$; 17 mg; 0.02 mmol)) and potassium carbonate (70 mg; 0.51 mmol) in MeCN (4.2 mL) and water (1.4 mL) was degased with argon. Under argon, the reaction mixture was stirred at 130° C. for 10 minutes in a microwave reactor. After cooling the reaction mixture was diluted with EE and washed with saturated aqueous sodium chloride solution. The organic phase was filtered using a Whatman filter and then concentrated.

The residue was dissolved in MeOH (1.5 mL) and an aqueous solution of hydrogen chloride (2N; 0.4 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (30 mg; 0.07 mmol).

$^1$H-NMR (400 MHz, DMSO-d6): δ [ppm]=1.29 (3H), 1.86 (3H), 3.29-3.40 (1H), 3.55 (1H), 3.70 (1H), 3.81 (1H), 4.03 (1H), 4.18 (1H), 4.60 (1H), 7.34 (1H), 7.45 (1H), 7.54-7.59 (1H), 7.62 (1H), 8.00-8.23 (2H), 8.38-8.45 (1H), 13.36 (1H).

Example 4

5-methyl-4-[2-methyl-6-(methylsulfonyl)pyridin-3-yl]-2-[(3R)-3-methylmorpholin-4-yl]-8-(1H-pyrazol-5-yl)-1,7-naphthyridine

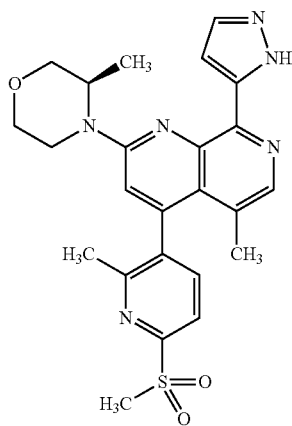 [SMILES: Cc1nc(S(C)(=O)=O)ccc1-c1cc(N2CCOC[C@H]2C)nc2c(-c3ccn[nH]3)ncc(C)c12]

A suspension of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (190 mg; 0.35 mmol), 2-methyl-6-(methylsulfonyl)-3-(4,4,5,5-tetramethyl-1,3,2-dioxaborolan-2-yl)pyridine (104 mg; 0.35 mmol), [1,1'-bis(diphenylphosphino)ferrocene]dichloropalladium(II) complex with dichloromethane (1:1, Pd(dppf)Cl$_2$; 29 mg; 0.04 mmol)) and potassium carbonate (121 mg; 0.88 mmol) in MeCN (7.4 mL) and water (2.5 mL) was degased with argon. Under argon, the reaction mixture was stirred at 130° C. for 10 minutes in a microwave reactor. After cooling the reaction mixture was diluted with EE and washed with saturated aqueous sodium chloride solution. The organic phase was filtered using a Whatman filter and then concentrated.

The residue was dissolved in MeOH (1.6 mL) and an aqueous solution of hydrogen chloride (2N; 0.4 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (68 mg; 0.14 mmol).

$^1$H-NMR (400 MHz, DMSO-d6): δ [ppm]=1.23-1.31 (3H), 1.74 (3H), 2.33 (3H), 3.35-3.37 (3H), 3.56 (1H), 3.66-3.85 (2H), 4.03 (1H), 4.12-4.22 (1H), 4.56 (1H), 7.36 (1H), 7.39 (1H), 7.53-7.67 (1H), 8.02 (1H), 8.08 (2H), 13.31-13.40 (1H).

Example 5

4-(2-chloro-1-methyl-1H-imidazol-5-yl)-5-methyl-2-[(3R)-3-methylmorpholin-4-yl]-8-(1H-pyrazol-5-yl)-1,7-naphthyridine

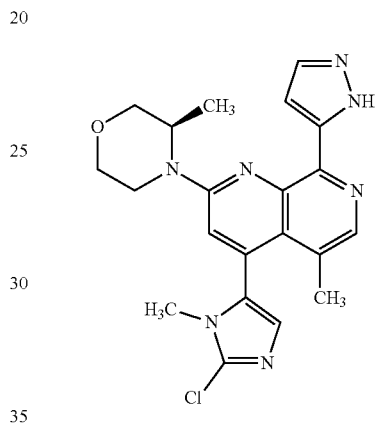

A suspension of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (190 mg; 0.35 mmol), 2-chloro-1-methyl-5-(4,4,5,5-tetramethyl-1,3,2-dioxaborolan-2-yl)-1H-imidazole (85 mg; 0.35 mmol), [1,1'-bis(diphenylphosphino)ferrocene]dichloropalladium(II) complex with dichloromethane (1:1, Pd(dppf)Cl$_2$; 29 mg; 0.04 mmol)) and potassium carbonate (121 mg; 0.88 mmol) in MeCN (7.4 mL) and water (2.5 mL) was degased with argon. Under argon, the reaction mixture was stirred at 130° C. for 10 minutes in a microwave reactor. After cooling the reaction mixture was diluted with EE and washed with saturated aqueous sodium chloride solution. The organic phase was filtered using a Whatman filter and then concentrated.

The residue was dissolved in MeOH (1.6 mL) and an aqueous solution of hydrogen chloride (2N; 0.4 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (22 mg; 0.05 mmol).

$^1$H-NMR (400 MHz, DMSO-d6): δ [ppm]=1.23-1.32 (3H), 1.92 (3H), 3.29 (3H), 3.35-3.41 (1H), 3.46-3.63 (1H), 3.66-3.74 (1H), 3.81 (1H), 4.03 (1H), 4.17 (1H), 4.57 (1H), 7.07 (1H), 7.33 (1H), 7.47 (1H), 7.61 (1H), 8.14-8.18 (1H), 13.35 (1H).

Example 6

4-[2-fluoro-4-(piperazin-1-yl)phenyl]-5-methyl-2-[(3R)-3-methylmorpholin-4-yl]-8-(1H-pyrazol-5-yl)-1,7-naphthyridine

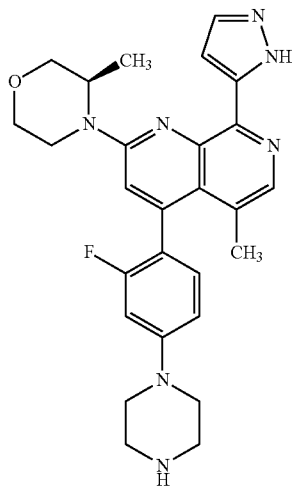 [SMILES: Cc1cnc(-c2ccn[nH]2)c2nc(N3CCOC[C@H]3C)cc(-c3ccc(N4CCNCC4)cc3F)c12]

A suspension of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (190 mg; 0.35 mmol), [2-fluoro-4-(piperazin-1-yl)phenyl]boronic acid (79 mg; 0.35 mmol), [1,1'-bis(diphenylphosphino)ferrocene]dichloropalladium(II) complex with dichloromethane (1:1, Pd(dppf)Cl$_2$; 29 mg; 0.04 mmol)) and potassium carbonate (121 mg; 0.88 mmol) in MeCN (7.4 mL) and water (2.5 mL) was degased with argon. Under argon, the reaction mixture was stirred at 130° C. for 10 minutes in a microwave reactor. After cooling the reaction mixture was diluted with EE and washed with saturated aqueous sodium chloride solution. The organic phase was filtered using a Whatman filter and then concentrated.

The residue was dissolved in MeOH (1.6 mL) and an aqueous solution of hydrogen chloride (2N; 0.4 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (16 mg; 0.03 mmol).

$^1$H-NMR (400 MHz, DMSO-d6): δ [ppm]=1.22-1.32 (3H), 1.96 (3H), 2.82-2.89 (4H), 3.11-3.24 (4H), 3.29 (1H), 3.54 (1H), 3.69 (1H), 3.79 (1H), 4.01 (1H), 4.15 (1H), 4.57 (1H), 6.82-6.93 (2H), 7.21-7.35 (3H), 7.61 (1H), 8.10 (1H), 13.32 (1H).

Example 7

4-(2,3-difluorophenyl)-5-methyl-2-[(3R)-3-methylmorpholin-4-yl]-8-(1H-pyrazol-5-yl)-1,7-naphthyridine

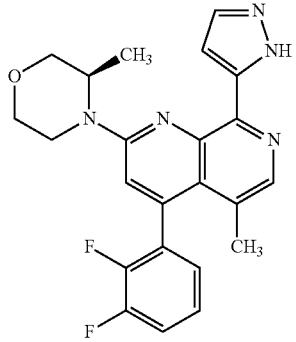 [SMILES: Cc1cnc(-c2ccn[nH]2)c2nc(N3CCOC[C@H]3C)cc(-c3cccc(F)c3F)c12]

A suspension of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (190 mg; 0.35 mmol), (2,3-difluorophenyl)boronic acid (55 mg; 0.35 mmol), [1,1'-bis(diphenylphosphino)ferrocene]-dichloropalladium(II) complex with dichloromethane (1:1, Pd(dppf)Cl$_2$; 29 mg; 0.04 mmol)) and potassium carbonate (121 mg; 0.88 mmol) in MeCN (7.4 mL) and water (2.5 mL) was degased with argon. Under argon, the reaction mixture was stirred at 130° C. for 10 minutes in a microwave reactor. After cooling the reaction mixture was diluted with EE and washed with saturated aqueous sodium chloride solution. The organic phase was filtered using a Whatman filter and then concentrated.

The residue was dissolved in MeOH (1.6 mL) and an aqueous solution of hydrogen chloride (2N; 0.4 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (56 mg; 0.13 mmol).

$^1$H-NMR (400 MHz, DMSO-d6): δ [ppm]=1.28 (3H), 1.89 (3H), 3.44-3.61 (1H), 3.69 (1H), 3.80 (1H), 4.02 (1H), 4.17 (1H), 4.58 (1H), 7.30-7.43 (4H), 7.56-7.67 (2H), 8.13 (1H), 13.35 (1H).

Example 8

N-5-methyl-2-[(3R)-3-methylmorpholin-4-yl]-8-(1H-pyrazol-5-yl)-1,7-naphthyridin-4-yltetrahydro-1H-1λ$^4$-thiophen-1-imine 1-oxide

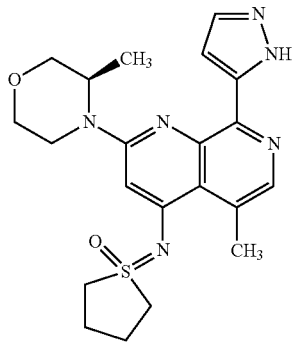 [SMILES: Cc1cnc(-c2ccn[nH]2)c2nc(N3CCOC[C@H]3C)cc(N=S3(=O)CCCC3)c12]

Under nitrogen, 4,5-bis(diphenylphosphino)-9,9-dimethylxanthene (11 mg; 0.018 mmol) and tris(dibenzylideneacetone)dipalladium(0) (8 mg; 0.009 mmol) were added to a mixture of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (100 mg; 0.185 mmol), tetrahydro-1H-1λ$^4$-thiophen-1-imine 1-oxide (29 mg; 0.24 mmol) and caesium carbonate (90 mg; 0.277 mmol) in toluene (1 mL). The mixture was stirred at 110° C. for 8 hours. After cooling, the reaction mixture was diluted with ethyl acetate and washed with water. The organic phase was filtered using a Whatman filter and concentrated to give the crude product that was used without further purification.

The residue was dissolved in MeOH (4 mL) and an aqueous solution of hydrogen chloride (2N; 0.2 mL) was added. The reaction mixture was stirred at room temperature for 2 hours. The mixture was basified by addition of an aqueous sodium bicarbonate solution and extracted with ethyl acetate (2×). The combined organic phases were filtered using a Whatman filter and concentrated. The residue was purified by preperative HPLC (Autopurifier: acidic conditions) to give the desired product (24 mg; 0.06 mmol).

$^1$H-NMR (400 MHz, DMSO-d6): δ [ppm]=1.24 (3H), 2.10-2.35 (4H), 2.77 (3H), 3.05-3.33 (2H), 3.36-3.63 (4H), 3.71 (1H), 3.81 (1H), 3.89-3.99 (1H), 4.04 (1H), 4.28-4.41 (1H), 6.60 (s, 1H), 7.24 (1H), 7.56 (1H), 8.03 (1H).

Example 9

4-[diethyl(oxido)-λ$^6$-sulfanylidene]amino-5-methyl-2-[(3R)-3-methylmorpholin-4-yl]-8-(1H-pyrazol-5-yl)-1,7-naphthyridine

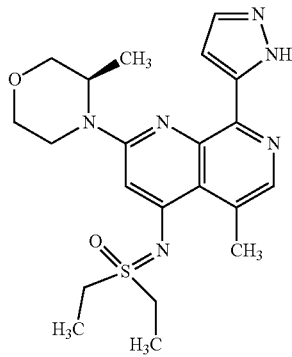 [SMILES: CCS(=O)(CC)=Nc1cc(N2CCOC[C@H]2C)nc2c(-c3ccn[nH]3)ncc(C)c12]

Under nitrogen 4,5-bis(diphenylphosphino)-9,9-dimethylxanthene (11 mg; 0.018 mmol) and tris(dibenzylideneacetone)dipalladium(0) (8 mg; 0.009 mmol) were added to a mixture of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (100 mg; 0.185 mmol), (S-ethylsulfonimidoyl)ethane (29 mg; 0.24 mmol) and caesium carbonate (90 mg; 0.277 mmol) in toluene (1 mL). The mixture was stirred at 110° C. for 7 hours. After cooling, the reaction mixture was diluted with ethyl acetate and washed with water. The organic phase was filtered using a Whatman filter and concentrated to give the crude product that was used without further purification.

The residue was dissolved in MeOH (4 mL) and an aqueous solution of hydrogen chloride (2N; 0.2 mL) was added. The reaction mixture was stirred at room temperature for 2 hours. The mixture was basified by addition of an aqueous sodium bicarbonate solution and extracted with ethyl acetate (2×). The combined organic phases were filtered using a Whatman filter and concentrated. The residue was purified by preperative HPLC (Autopurifier: acidic conditions) to give the desired product (29 mg; 0.07 mmol).

$^1$H-NMR (400 MHz, DMSO-d6): δ [ppm]=1.23 (3H), 1.31 (6H), 2.77 (3H), 3.24 (1H), 3.55 (5H), 3.70 (1H), 3.76-3.86 (1H), 3.88-3.98 (1H), 4.03 (1H), 4.18-4.40 (1H), 6.81 (1H), 7.23 (1H), 7.56 (1H), 8.02 (1H).

Example 10

5-methyl-2-[(3R)-3-methylmorpholin-4-yl]-4-(morpholin-4-yl)-8-(1H-pyrazol-5-yl)-1,7-naphthyridine

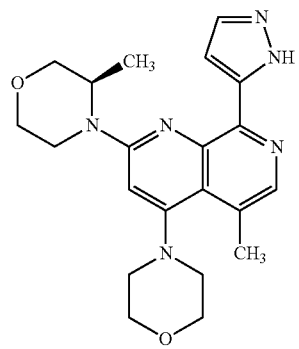 [SMILES: Cc1cnc(-c2ccn[nH]2)c2nc(N3CCOC[C@H]3C)cc(N3CCOCC3)c12]

A mixture of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (150 mg; 0.28 mmol) and morpholine (82 mg; 0.94 mmol) in MeCN (0.4 mL) was stirred for 10 hours at 70° C. After cooling, the mixture was diluted with EE and THF and washed with a saturated aqueous solution of sodium chloride. The organic phase was filtered using a Whatman filter and concentrated to give the crude product that was used without further purification.

The residue was dissolved in MeOH (1.3 mL) and an aqueous solution of hydrogen chloride (2N; 0.3 mL) was added. The reaction mixture was stirred at room temperature for 1 hour. The mixture was basified by addition of an aqueous sodium bicarbonate solution and extracted with EE/THF (1:1; 2×). The combined organic phases were filtered using a Whatman filter and concentrated. The residue was purified by preperative HPLC (Autopurifier: basic conditions) to give the desired product (17 mg; 0.04 mmol).

$^1$H-NMR (400 MHz, DMSO-d6): δ [ppm]=1.26 (3H), 2.76-2.93 (5H), 3.10-3.17 (2H), 3.21-3.33 (1H), 3.53 (1H), 3.66-3.91 (6H), 3.98-4.12 (2H), 4.51-4.58 (1H), 6.80 (1H), 7.24 (1H), 7.57 (1H), 8.07 (1H), 13.26 (1H).

Example 11

(1-{5-methyl-2-[(3R)-3-methylmorpholin-4-yl]-8-(1H-pyrazol-5-yl)-1,7-naphthyridin-4-yl}piperidin-4-yl)methanol

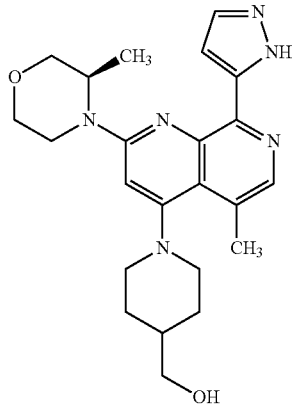 [SMILES: Cc1cnc(-c2ccn[nH]2)c2nc(N3CCOC[C@H]3C)cc(N3CCC(CO)CC3)c12]

A mixture of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (150 mg; 0.28 mmol) and piperidin-4-ylmethanol (108 mg; 0.94 mmol) in MeCN (0.4 mL) was stirred for 3 hours at 70° C. After cooling, the mixture was diluted with EE and THF and washed with a saturated aqueous solution of sodium chloride. The organic phase was filtered using a Whatman filter and concentrated to give the crude product that was used without further purification.

The residue was dissolved in MeOH (1.3 mL) and an aqueous solution of hydrogen chloride (2N; 0.3 mL) was added. The reaction mixture was stirred at room temperature for 1 hour. The mixture was basified by addition of an aqueous sodium bicarbonate solution and extracted with EE/THF (1:1; 2×). The combined organic phases were filtered using a Whatman filter and concentrated. The residue was purified by preperative HPLC (Autopurifier: basic conditions) to give the desired product (19 mg; 0.04 mmol).

$^1$H-NMR (400 MHz, DMSO-d6): δ [ppm]=1.25 (3H), 1.38-1.56 (2H), 1.69-1.85 (2H), 2.52-2.69 (2H), 2.76 (3H), 3.24-3.39 (6H), 3.52 (1H), 3.68 (1H), 3.80 (1H), 3.98-4.10 (2H), 4.48-4.58 (2H), 6.78 (1H), 7.23 (1H), 7.56 (1H), 8.06 (1H), 13.26 (1H).

Example 12

5-methyl-2-[(3R)-3-methylmorpholin-4-yl]-4-[4-(methylsulfonyl)piperazin-1-yl]-8-(1H-pyrazol-5-yl)-1,7-naphthyridine

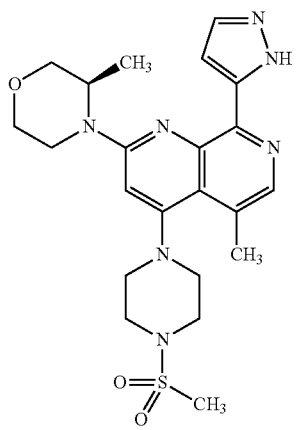 [SMILES: Cc1cnc(-c2ccn[nH]2)c2nc(N3CCOC[C@H]3C)cc(N3CCN(S(C)(=O)=O)CC3)c12]

A mixture of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (150 mg; 0.28 mmol) and 1-(methylsulfonyl)piperazine (155 mg; 0.94 mmol) in MeCN (0.4 mL) was stirred for 10 hours at 70° C. Additional 1-(methylsulfonyl)piperazine (155 mg; 0.94 mmol) was added and the mixture was stirred at 70° C. for 72 hours. After cooling, the mixture was diluted with EE and THF and washed with a saturated aqueous solution of sodium chloride. The organic phase was filtered using a Whatman filter and concentrated to give the crude product that was used without further purification.

The residue was dissolved in MeOH (1.3 mL) and an aqueous solution of hydrogen chloride (2N; 0.3 mL) was added. The reaction mixture was stirred at room temperature for 1 hour. The mixture was basified by addition of an aqueous sodium bicarbonate solution and extracted with EE/THF (1:1; 2×). The combined organic phases were filtered using a Whatman filter and concentrated. The residue was purified by preperative HPLC (Autopurifier: basic conditions) to give the desired product (34 mg; 0.07 mmol).

$^1$H-NMR (400 MHz, DMSO-d6): δ [ppm]=1.26 (3H), 2.78 (3H), 2.86 (3H), 2.99 (3H), 3.08-3.20 (3H), 3.24-3.32 (1H), 3.49-3.62 (3H), 3.68 (1H), 3.81 (1H), 3.99-4.06 (1H), 4.10 (1H), 4.55 (1H), 6.88 (1H), 7.24 (1H), 7.57 (1H), 8.09 (1H), 13.26 (1H).

Example 13

N-(2,2-dimethylpropyl)-N,5-dimethyl-2-[(3R)-3-methylmorpholin-4-yl]-8-(1H-pyrazol-5-yl)-1,7-naphthyridin-4-amine

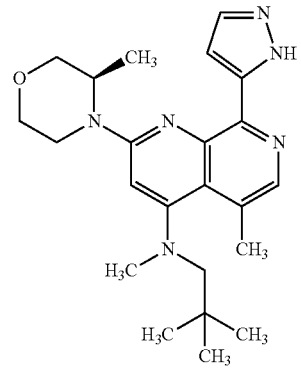 [SMILES: Cc1cnc(-c2ccn[nH]2)c2nc(N3CCOC[C@H]3C)cc(N(C)CC(C)(C)C)c12]

A mixture of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl-trifluoromethanesulfonate (150 mg; 0.28 mmol) and N,2,2-trimethylpropan-1-amine (95 mg; 0.94 mmol) in MeCN (0.4 mL) was stirred for 72 hours at 70° C. After cooling, the mixture was diluted with EE and THF and washed with a saturated aqueous solution of sodium chloride. The organic phase was filtered using a Whatman filter and concentrated to give the crude product that was used without further purification.

The residue was dissolved in MeOH (1.3 mL) and an aqueous solution of hydrogen chloride (2N; 0.3 mL) was added. The reaction mixture was stirred at room temperature for 1 hour. The mixture was basified by addition of an aqueous sodium bicarbonate solution and extracted with EE/THF (1:1; 2×). The combined organic phases were filtered using a Whatman filter and concentrated. The residue was purified by preperative HPLC (Autopurifier: basic conditions) to give the desired product (9 mg; 0.02 mmol).

$^{1}$H-NMR (400 MHz, DMSO-d6): δ [ppm]=0.88-0.95 (9H), 1.23 (3H), 2.66-2.82 (7H), 3.22-3.31 (1H), 3.50-3.73 (3H), 3.77-3.84 (1H), 4.01-4.15 (2H), 4.53 (1H), 6.99 (1H), 7.24 (1H), 7.56 (1H), 8.07 (1H), 13.26 (1H).

Example 14 methyl 5-methyl-2-[(3R)-3-methylmorpholin-4-yl]-8-(1H-pyrazol-5-yl)-1,7-naphthyridine-4-carboxylate

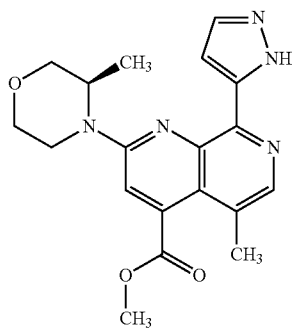 [SMILES: COC(=O)c1cc(N2CCOC[C@H]2C)nc2c(-c3ccn[nH]3)ncc(C)c12]

Methyl 5-methyl-2-[(3R)-3-methylmorpholin-4-yl]-8-{1-[(tetrahydro-2H-pyran-2-yl]-1H-pyrazol-5-yl}-1,7-naphthyridine-4-carboxylate (50 mg; 0.11 mmol) was dissolved in MeOH (0.5 mL) and an aqueous solution of hydrogen chloride (2N; 0.1 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated to give the desired product (30 mg; 0.08 mmol).

$^{1}$H-NMR (400 MHz, DMSO-d6): δ [ppm]=1.15-1.32 (3H), 2.39 (3H), 3.47-3.61 (1H), 3.69 (1H), 3.75-3.87 (1H), 3.95-4.05 (4H), 4.14 (1H), 4.57 (1H), 7.31 (1H), 7.60 (1H), 7.66 (1H), 8.23 (1H), 13.35 (1H).

Example 15

5-methyl-4-(1-methyl-1H-imidazol-5-yl)-2-[(3R)-3-methylmorpholin-4-yl]-8-(1H-pyrazol-5-yl)-1,7-naphthyridine

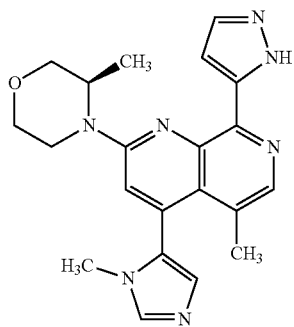 [SMILES: Cc1cnc(-c2ccn[nH]2)c2nc(N3CCOC[C@H]3C)cc(-c3cncn3C)c12]

A suspension of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (150 mg; 0.28 mmol), 1-methyl-5-(4,4,5,5-tetramethyl-1,3,2-dioxaborolan-2-yl)-1H-imidazole (115 mg; 0.55 mmol), [1,1'-bis(diphenylphosphino)ferrocene]dichloropalladium(II) complex with dichloromethane (1:1, Pd(dppf)Cl$_2$; 23 mg; 0.03 mmol)) and potassium carbonate (96 mg; 0.70 mmol) in MeCN (2.9 mL) and water (1.5 mL) was degased with argon. Under argon, the reaction mixture was stirred at 130° C. for 10 minutes in a microwave reactor. After cooling the reaction mixture was diluted with EE and washed with saturated aqueous sodium chloride solution. The organic phase was filtered using a Whatman filter and then concentrated.

The residue was dissolved in MeOH (2.4 mL) and an aqueous solution of hydrogen chloride (2N; 0.3 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (17 mg; 0.04 mmol).

$^{1}$H-NMR (400 MHz, DMSO-d6): δ [ppm]=1.28 (3H), 1.83 (3H), 3.34 (3H), 3.55 (1H), 3.69 (1H), 3.75-3.85 (1H), 3.97-4.07 (1H), 4.12-4.23 (1H), 4.59 (1H), 7.04 (1H), 7.28-7.42 (2H), 7.61 (1H), 7.82 (1H), 8.14 (1H), 13.34 (1H).

Example 16

5-methyl-2-[(3R)-3-methylmorpholin-4-yl]-4-(2-methyl-1,3-thiazol-5-yl)-8-(1H-pyrazol-5-yl)-1,7-naphthyridine

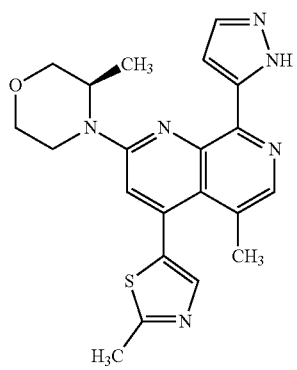 [SMILES: Cc1ncc(-c2cc(N3CCOC[C@H]3C)nc3c(-c4ccn[nH]4)ncc(C)c23)s1]

A suspension of 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (150 mg; 0.28 mmol), 2-methyl-5-(4,4,5,5-tetramethyl-1,3,2-dioxaborolan-2-yl)-1,3-thiazole (125 mg; 0.55 mmol), [1,1'-bis(diphenylphosphino)ferrocene]dichloropalladium(II) complex with dichloromethane (1:1, Pd(dppf)Cl$_2$; 23 mg; 0.03 mmol)) and potassium carbonate (96 mg; 0.70 mmol) in MeCN (2.9 mL) and water (1.5 mL) was degased with argon. Under argon, the reaction mixture was stirred at 130° C. for 10 minutes in a microwave reactor. After cooling the reaction mixture was diluted with EE and washed with saturated aqueous sodium chloride solution. The organic phase was filtered using a Whatman filter and then concentrated.

The residue was dissolved in MeOH (2.4 mL) and an aqueous solution of hydrogen chloride (2N; 0.3 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (5 mg; 0.01 mmol).

$^1$H-NMR (400 MHz, DMSO-d6): δ [ppm]=1.27 (3H), 2.08 (3H), 2.76 (3H), 3.54 (1H), 3.68 (1H), 3.80 (1H), 4.02 (1H), 4.15 (1H), 4.58 (1H), 7.32 (1H), 7.42 (1H), 7.61 (2H), 7.71 (1H), 8.14 (1H), 13.34 (1H).

Example 17 ethyl methyl{5-methyl-2-[(3R)-3-methylmorpholin-4-yl]-8-(1H-pyrazol-5-yl)-1,7-naphthyridin-4-yl}phosphinate

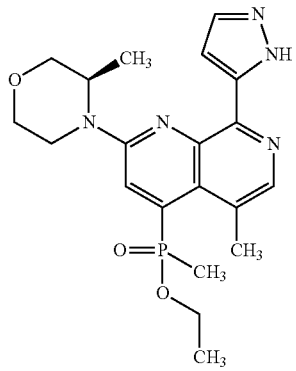 [SMILES: CCOP(C)(=O)c1cc(N2CCOC[C@H]2C)nc2c(-c3ccn[nH]3)ncc(C)c12]

A mixture 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (150 mg; 0.28 mmol), ethyl methylphosphinate (30 mg; 0.28 mmol), palladium(II) acetate (1 mg; 0.006 mmol), 1,1'-bis(diphenylphosphino)ferrocene (3 mg; 0.006 mmol) and ethyldiisopropylamine (47 mg; 0.36 mmol) in DMF (1.2 ml) and 1,2-dimethoxyethane (0.1 ml) was degased with argon. Under argon, the reaction mixture was stirred at room temperature for 10 minutes and then at 110° C. overnight. After cooling the reaction mixture was diluted with ethyl acetate and washed with saturated aqueous sodium bicarbonate solution and saturated aqueous sodium chloride solution. The organic phase was filtered using a Whatman filter and then concentrated to give the crude product that was used without further purification in the next step.

The residue was dissolved in MeOH (1.2 mL) and an aqueous solution of hydrogen chloride (2N; 0.3 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: basic conditions) to give the desired product (3 mg; 0.01 mmol).

$^1$H-NMR (400 MHz, DMSO-d6): δ [ppm]=1.10-1.34 (6H), 2.01-2.10 (3H), 2.89 (3H), 3.39-3.45 (1H), 3.46-3.61 (1H), 3.69 (1H), 3.75-3.89 (1H), 3.96-4.19 (4H), 4.53-4.63 (1H), 7.24 (1H), 7.60 (1H), 7.75 (1H), 8.25 (1H), 13.31 (1H).

Example 18

4-(dimethylphosphoryl)-5-methyl-2-[(3R)-3-methylmorpholin-4-yl]-8-(1H-pyrazol-5-yl)-1,7-naphthyridine

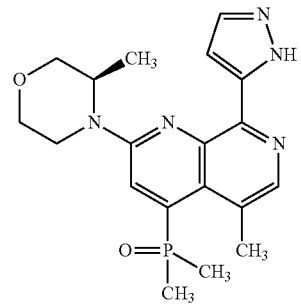 [SMILES: Cc1cnc(-c2ccn[nH]2)c2nc(N3CCOC[C@H]3C)cc(P(C)(C)=O)c12]

A mixture 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (150 mg; 0.28 mmol), dimethylphosphine oxide (22 mg; 0.28 mmol), palladium(II) acetate (1 mg; 0.006 mmol), 1,1'-bis(diphenylphosphino)ferrocene (3 mg; 0.006 mmol) and ethyldiisopropylamine (47 mg; 0.36 mmol) in DMF (1.2 ml) and 1,2-dimethoxyethane (0.1 ml) was degased with argon. Under argon, the reaction mixture was stirred at room temperature for 10 minutes and then at 110° C. overnight. After cooling the reaction mixture was diluted with ethyl acetate and washed with saturated aqueous sodium bicarbonate solution and saturated aqueous sodium chloride solution. The organic phase was filtered using a Whatman filter and then concentrated to give the crude product that was used without further purification in the next step.

The residue was dissolved in MeOH (1.3 mL) and an aqueous solution of hydrogen chloride (2N; 0.3 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: acidic conditions) to give the desired product (9 mg; 0.02 mmol).

$^1$H-NMR (400 MHz, DMSO-d6): δ [ppm]=1.30 (3H), 1.95 (6H), 2.99 (3H), 3.35-3.40 (1H), 3.54 (1H), 3.69 (1H), 3.83 (1H), 4.02-4.07 (1H), 4.14-4.20 (1H), 4.61 (1H), 7.24 (1H), 7.55-7.61 (2H), 8.24 (1H), 13.31 (1H).

Example 19

2-methylpropyl methyl{5-methyl-2-[(3R)-3-methyl-morpholin-4-yl]-8-(1H-pyrazol-5-yl)-1,7-naphthyridin-4-yl}phosphinate

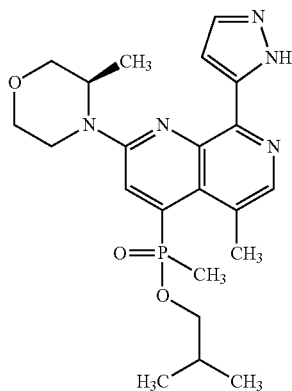 [SMILES: Cc1cnc(-c2ccn[nH]2)c2nc(N3CCOC[C@H]3C)cc(P(C)(=O)OCC(C)C)c12]

A mixture 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (150 mg; 0.28 mmol), isobutyl methylphosphinate (38 mg; 0.28 mmol), palladium(II) acetate (1 mg; 0.006 mmol), 1,1'-bis(diphenylphosphino)ferrocene (3 mg; 0.006 mmol) and ethyldiisopropylamine (47 mg; 0.36 mmol) in DMF (1.2 ml) and 1,2-dimethoxyethane (0.1 ml) was degased with argon. Under argon, the reaction mixture was stirred at room temperature for 10 minutes and then at 110° C. overnight. After cooling the reaction mixture was diluted with ethyl acetate and washed with saturated aqueous sodium bicarbonate solution and saturated aqueous sodium chloride solution.

The organic phase was filtered using a Whatman filter and then concentrated to give the crude product that was used without further purification in the next step.

The residue was dissolved in MeOH (1.2 mL) and an aqueous solution of hydrogen chloride (2N; 0.3 mL) was added. The reaction mixture was stirred at room temperature for 1 hour. The mixture was basified by addition of an aqueous sodium bicarbonate solution. Aqueous sodium chloride solution was added and the mixture was extracted with ethyl acetate/THF (1:1; 2×). The combined organic phases were filtered using a Whatman filter and concentrated. The residue was purified by preperative HPLC (Autopurifier: acidic conditions) to give the desired product (10 mg; 0.02 mmol).

$^1$H-NMR (400 MHz, DMSO-d6): δ [ppm]=0.72-0.96 (6H), 1.31 (3H), 1.84-2.00 (1H), 2.06 (3H), 2.90 (3H), 3.37-3.44 (1H), 3.48-3.64 (1H), 3.65-3.86 (3H), 4.05 (1H), 4.09-4.25 (2H), 4.58 (1H), 7.24 (1H), 7.60 (1H), 7.75 (1H), 8.24 (1H), 13.30 (1H).

The following examples were prepared by Automated Medicinal Chemistry methods using the following procedure:

To 0.2 mmol 5-methyl-2-[(3R)-3-methylmorpholin-4-yl]-8-{1-[(2R)-tetrahydro-2H-pyran-2-yl]-1H-pyrazol-5-yl}-1,7-naphthyridin-4-yl trifluoromethanesulfonate (0.25 M in NMP, 800 μL) were added 2 eq of boronic acid derivative, (0.4 mmol, 800 μL, 0.5 M in NMP) 40 μmol 1,1'-Bis(diphenylphosphino)ferrocene]dichloropalladium(II) (0.04 M in NMP, 1000 μL) and 0.6 mmol potassium carbonate (1 M in water, 600 μL) and the mixture was heated in a heating block at 110° C. overnight. After cooling, 1.2 mmol HCl (2M in water, 600 μL) were added and the mixture was heated in heating block for 10 hours at 50° C. After cooling, the mixture was filtered, washed with NMP and subjected to preparative HPLC to yield the target product.

| Example | Structure | Retention Time [min] | Mol Weight (calc) | Mol Weight (found) | Method |
|---|---|---|---|---|---|
| 20 | 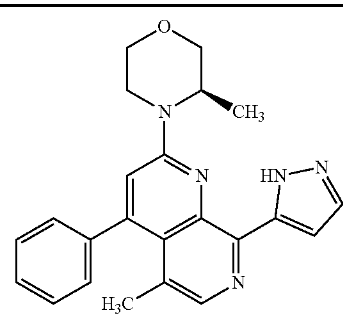 | 0.96 | 385.5 | 386.5 | 5 |
| 21 | 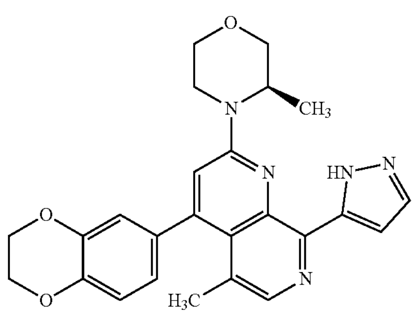 [SMILES: Cc1cnc(-c2ccn[nH]2)c2nc(N3CCOC[C@H]3C)cc(-c3ccc4c(c3)OCCO4)c12] | 0.94 | 443.5 | 444.5 | 5 |

-continued
| Example | Structure | Retention Time [min] | Mol Weight (calc) | Mol Weight (found) | Method |
|---|---|---|---|---|---|
| 22 | 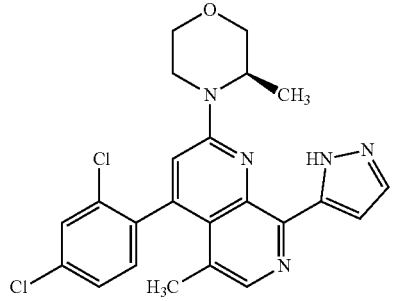 [SMILES: Cc1cnc(-c2ccn[nH]2)c2nc(N3CCOC[C@H]3C)cc(-c3ccc(Cl)cc3Cl)c12] | 1.15 | 454.4 | 455.4 | 5 |
| 23 | 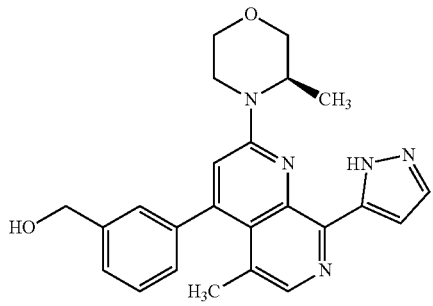 [SMILES: Cc1cnc(-c2ccn[nH]2)c2nc(N3CCOC[C@H]3C)cc(-c3cccc(CO)c3)c12] | 0.81 | 415.5 | 416.5 | 5 |
| 24 | 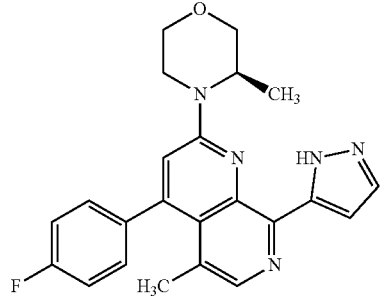 [SMILES: Cc1cnc(-c2ccn[nH]2)c2nc(N3CCOC[C@H]3C)cc(-c3ccc(F)cc3)c12] | 0.98 | 403.5 | 404.5 | 5 |
| 25 | 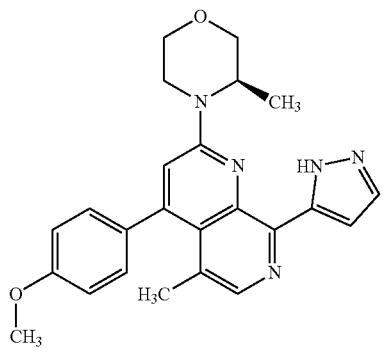 [SMILES: COc1ccc(-c2cc(N3CCOC[C@H]3C)nc3c(-c4ccn[nH]4)ncc(C)c23)cc1] | 0.97 | 415.5 | 416.5 | 5 |

-continued

| Example | Structure | Retention Time [min] | Mol Weight (calc) | Mol Weight (found) | Method |
|---------|-----------|----------------------|-------------------|--------------------|--------|
| 26 | 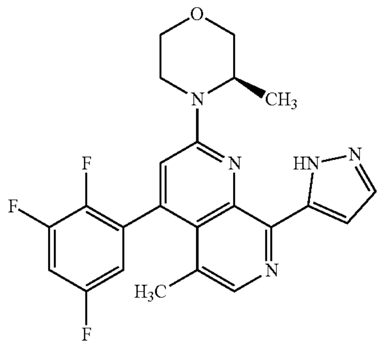 [SMILES: Cc1cnc(-c2ccn[nH]2)c2nc(N3CCOC[C@H]3C)cc(-c3cc(F)cc(F)c3F)c12] | 1.06 | 439.4 | 440.4 | 5 |
| 27 | 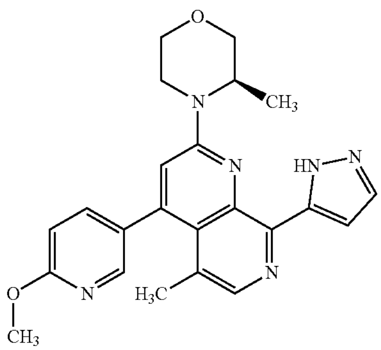 [SMILES: COc1ccc(-c2cc(N3CCOC[C@H]3C)nc3c(-c4ccn[nH]4)ncc(C)c23)cn1] | 0.89 | 416.5 | 417.5 | 5 |
| 28 | 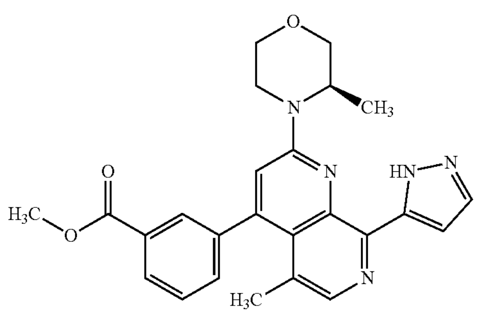 [SMILES: COC(=O)c1cccc(-c2cc(N3CCOC[C@H]3C)nc3c(-c4ccn[nH]4)ncc(C)c23)c1] | 0.96 | 443.5 | 444.5 | 5 |
| 29 | 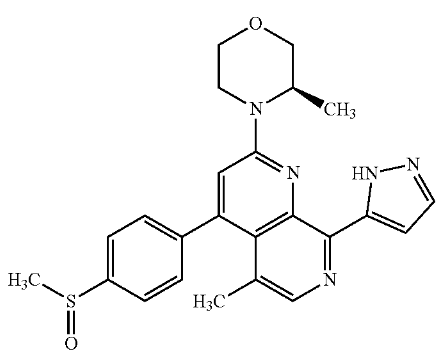 [SMILES: Cc1cnc(-c2ccn[nH]2)c2nc(N3CCOC[C@H]3C)cc(-c3ccc(S(C)=O)cc3)c12] | 0.75 | 447.6 | 448.6 | 5 |

-continued

| Example | Structure | Retention Time [min] | Mol Weight (calc) | Mol Weight (found) | Method |
|---|---|---|---|---|---|
| 30 | 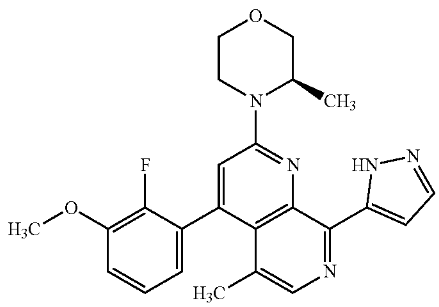 | 0.97 | 433.5 | 434.5 | 5 |
| 31 | 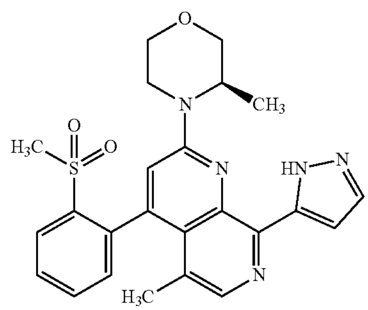 [SMILES: Cc1cnc(-c2ccn[nH]2)c2nc(N3CCOC[C@H]3C)cc(-c3ccccc3S(C)(=O)=O)c12] | 0.81 | 463.6 | 464.6 | 5 |
| 32 | 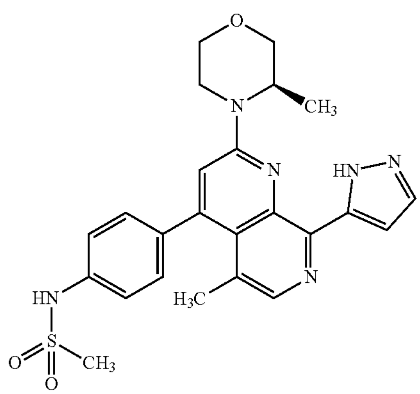 [SMILES: Cc1cnc(-c2ccn[nH]2)c2nc(N3CCOC[C@H]3C)cc(-c3ccc(NS(C)(=O)=O)cc3)c12] | 0.81 | 478.6 | 479.6 | 5 |
| 33 | 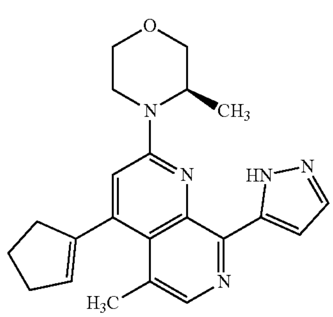 [SMILES: Cc1cnc(-c2ccn[nH]2)c2nc(N3CCOC[C@H]3C)cc(C3=CCCC3)c12] | 0.97 | 375.5 | 376.5 | 5 |

-continued

| Example | Structure | Retention Time [min] | Mol Weight (calc) | Mol Weight (found) | Method |
|---------|-----------|----------------------|-------------------|--------------------|--------|
| 34 | 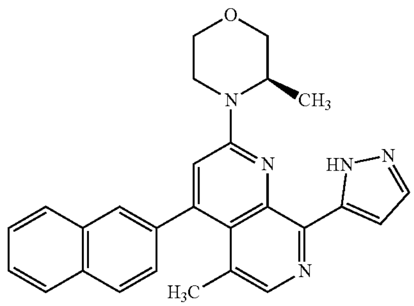 [SMILES: Cc1cnc(-c2ccn[nH]2)c2nc(N3CCOC[C@H]3C)cc(-c3ccc4ccccc4c3)c12] | 0.91 | 436.5 | 437.5 | 5 |
| 35 | 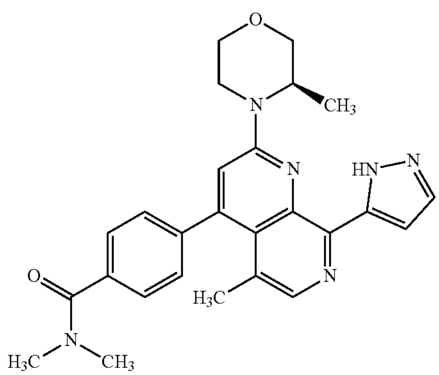 [SMILES: Cc1cnc(-c2ccn[nH]2)c2nc(N3CCOC[C@H]3C)cc(-c3ccc(C(=O)N(C)C)cc3)c12] | 0.81 | 456.5 | 457.5 | 5 |
| 36 | 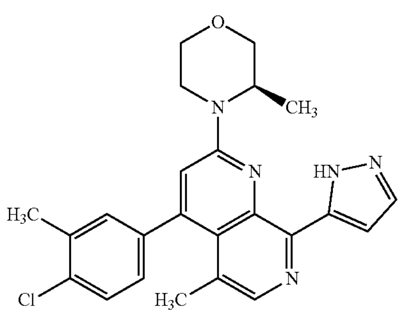 [SMILES: Cc1cc(-c2cc(N3CCOC[C@H]3C)nc3c(-c4ccn[nH]4)ncc(C)c23)ccc1Cl] | 1.14 | 433.9 | 434.9 | 5 |
| 37 | 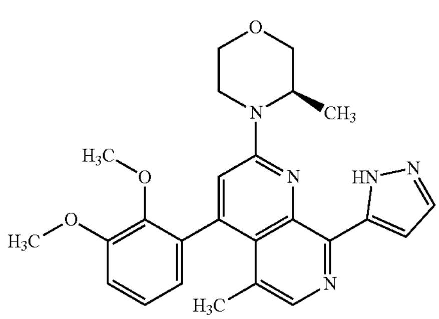 [SMILES: COc1cccc(-c2cc(N3CCOC[C@H]3C)nc3c(-c4ccn[nH]4)ncc(C)c23)c1OC] | 0.96 | 445.5 | 446.5 | 5 |

-continued

| Example | Structure | Retention Time [min] | Mol Weight (calc) | Mol Weight (found) | Method |
|---------|-----------|----------------------|-------------------|--------------------|--------|
| 38 | 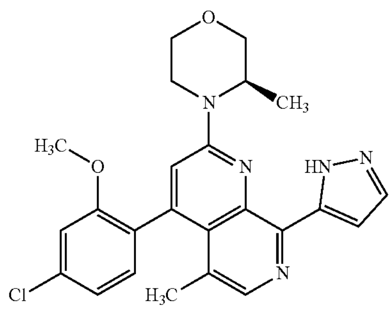 [SMILES: COc1cc(Cl)ccc1-c1cc(N2CCOC[C@H]2C)nc2c(-c3ccn[nH]3)ncc(C)c12] | 1.05 | 449.9 | 450.9 | 5 |
| 39 | 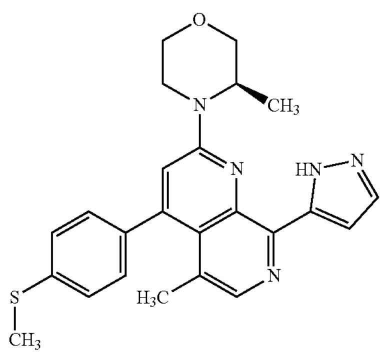 [SMILES: CSc1ccc(-c2cc(N3CCOC[C@H]3C)nc3c(-c4ccn[nH]4)ncc(C)c23)cc1] | 1.04 | 431.6 | 432.6 | 5 |
| 40 | 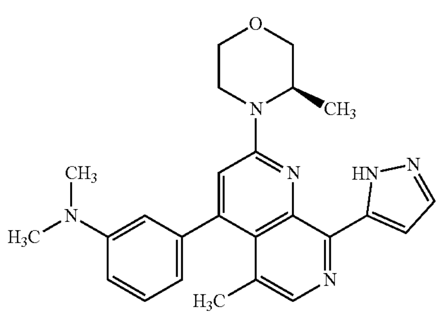 [SMILES: Cc1cnc(-c2ccn[nH]2)c2nc(N3CCOC[C@H]3C)cc(-c3cccc(N(C)C)c3)c12] | 1.01 | 428.5 | 429.5 | 5 |
| 41 | 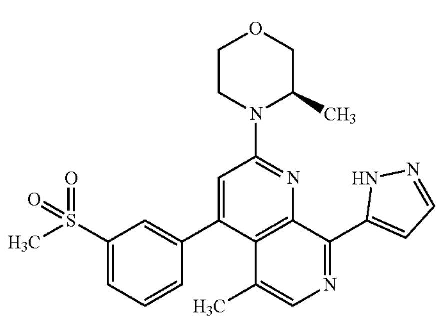 [SMILES: Cc1cnc(-c2ccn[nH]2)c2nc(N3CCOC[C@H]3C)cc(-c3cccc(S(C)(=O)=O)c3)c12] | 0.81 | 463.6 | 464.6 | 5 |

-continued

| Example | Structure | Retention Time [min] | Mol Weight (calc) | Mol Weight (found) | Method |
|---------|-----------|---------------------|-------------------|--------------------|--------|
| 42 | 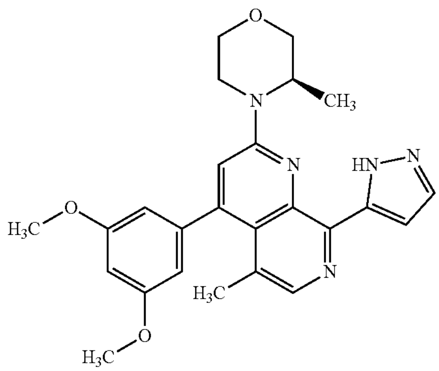 [SMILES: COc1cc(OC)cc(-c2cc(N3CCOC[C@H]3C)nc3c(-c4ccn[nH]4)ncc(C)c23)c1] | 1.00 | 445.5 | 446.5 | 5 |
| 43 | 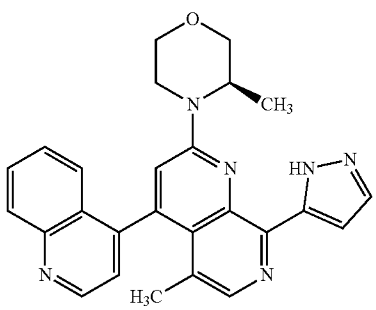 [SMILES: Cc1cnc(-c2ccn[nH]2)c2nc(N3CCOC[C@H]3C)cc(-c3ccnc4ccccc34)c12] | 0.86 | 436.5 | 437.5 | 5 |
| 44 | 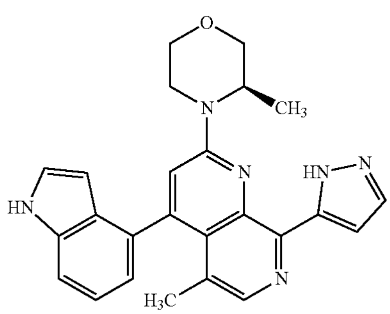 [SMILES: Cc1cnc(-c2ccn[nH]2)c2nc(N3CCOC[C@H]3C)cc(-c3cccc4[nH]ccc34)c12] | 0.92 | 424.5 | 425.5 | 5 |
| 45 | 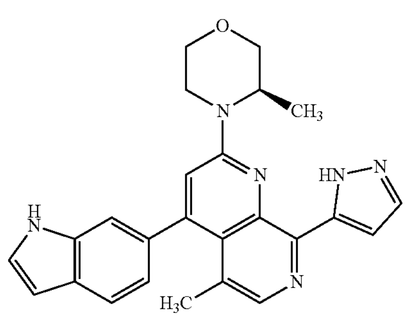 [SMILES: Cc1cnc(-c2ccn[nH]2)c2nc(N3CCOC[C@H]3C)cc(-c3ccc4cc[nH]c4c3)c12] | 0.97 | 424.5 | 425.5 | 5 |

-continued

| Example | Structure | Retention Time [min] | Mol Weight (calc) | Mol Weight (found) | Method |
|---|---|---|---|---|---|
| 46 | 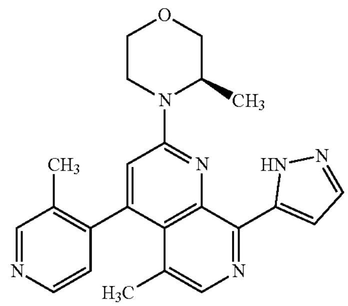 [SMILES: Cc1cnccc1-c1cc(N2CCOC[C@H]2C)nc2c(-c3ccn[nH]3)ncc(C)c12] | 0.70 | 400.5 | 401.5 | 5 |
| 47 | 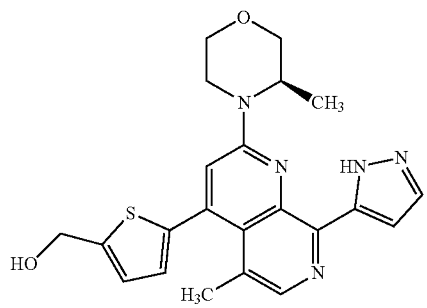 [SMILES: Cc1cnc(-c2ccn[nH]2)c2nc(N3CCOC[C@H]3C)cc(-c3ccc(CO)s3)c12] | 0.80 | 421.5 | 422.5 | 5 |
| 48 | 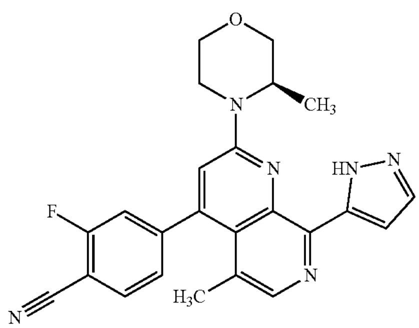 [SMILES: Cc1cnc(-c2ccn[nH]2)c2nc(N3CCOC[C@H]3C)cc(-c3ccc(C#N)c(F)c3)c12] | 0.96 | 428.5 | 429.5 | 5 |
| 49 | 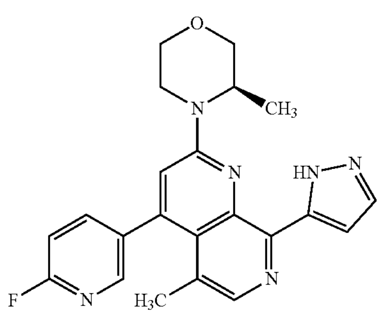 [SMILES: Cc1cnc(-c2ccn[nH]2)c2nc(N3CCOC[C@H]3C)cc(-c3ccc(F)nc3)c12] | 0.84 | 404.4 | 405.4 | 5 |
| 50 | 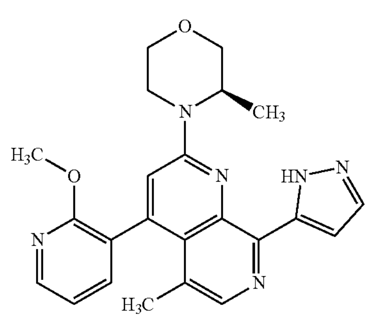 [SMILES: COc1ncccc1-c1cc(N2CCOC[C@H]2C)nc2c(-c3ccn[nH]3)ncc(C)c12] | 0.87 | 416.5 | 417.5 | 5 |

-continued

| Example | Structure | Retention Time [min] | Mol Weight (calc) | Mol Weight (found) | Method |
|---------|-----------|----------------------|-------------------|--------------------|--------|
| 51 | 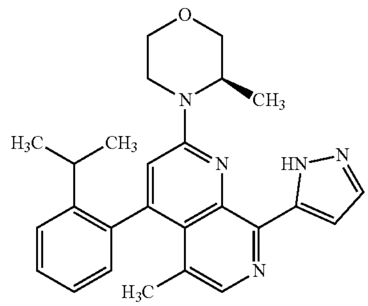 [SMILES: Cc1cnc(-c2ccn[nH]2)c2nc(N3CCOC[C@H]3C)cc(-c3ccccc3C(C)C)c12] | 1.13 | 427.5 | 428.5 | 5 |
| 52 | 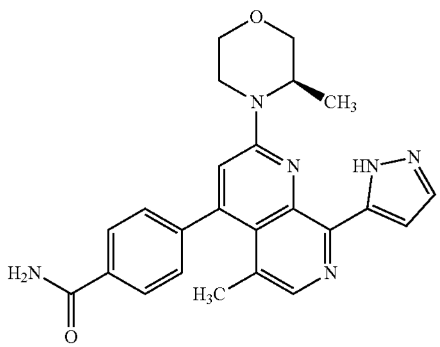 [SMILES: Cc1cnc(-c2ccn[nH]2)c2nc(N3CCOC[C@H]3C)cc(-c3ccc(C(N)=O)cc3)c12] | 0.72 | 428.5 | 429.5 | 5 |
| 53 | 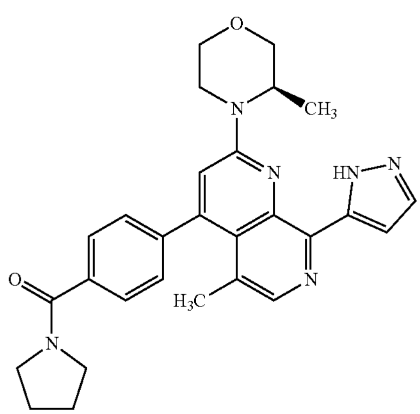 [SMILES: Cc1cnc(-c2ccn[nH]2)c2nc(N3CCOC[C@H]3C)cc(-c3ccc(C(=O)N4CCCC4)cc3)c12] | 0.86 | 482.6 | 483.6 | 5 |
| 54 | 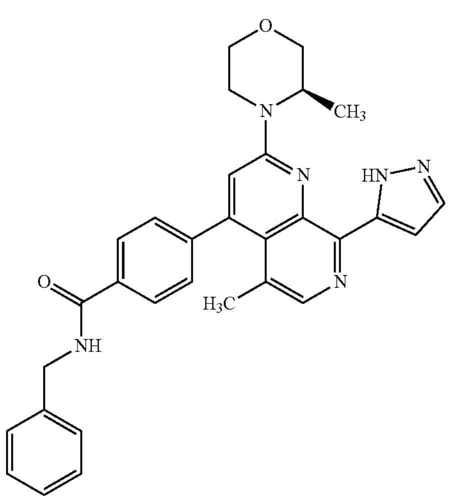 [SMILES: Cc1cnc(-c2ccn[nH]2)c2nc(N3CCOC[C@H]3C)cc(-c3ccc(C(=O)NCc4ccccc4)cc3)c12] | 0.97 | 518.6 | 519.6 | 5 |

-continued

| Example | Structure | Retention Time [min] | Mol Weight (calc) | Mol Weight (found) | Method |
|---------|-----------|----------------------|-------------------|--------------------|--------|
| 55 | 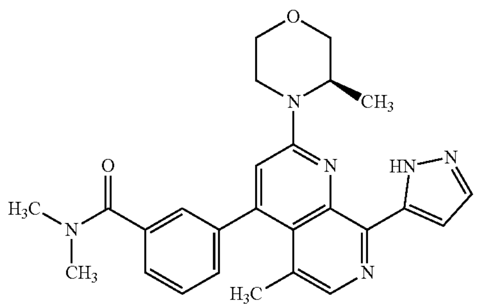 [SMILES: Cc1cnc(-c2ccn[nH]2)c2nc(N3CCOC[C@H]3C)cc(-c3cccc(C(=O)N(C)C)c3)c12] | 0.82 | 456.5 | 457.5 | 5 |
| 56 | 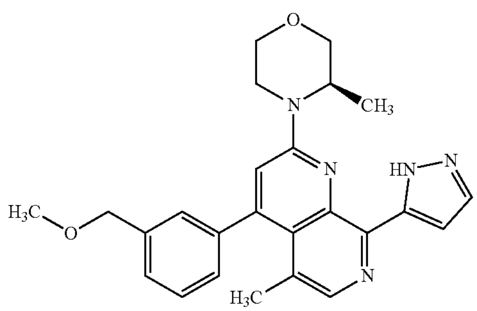 [SMILES: COCc1cccc(-c2cc(N3CCOC[C@H]3C)nc3c(-c4ccn[nH]4)ncc(C)c23)c1] | 0.96 | 429.5 | 430.5 | 5 |
| 57 | 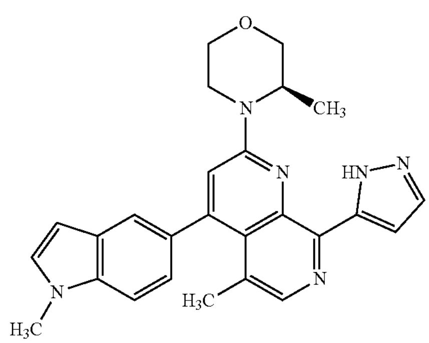 [SMILES: Cc1cnc(-c2ccn[nH]2)c2nc(N3CCOC[C@H]3C)cc(-c3ccc4c(ccn4C)c3)c12] | 1.01 | 438.5 | 439.5 | 5 |
| 58 | 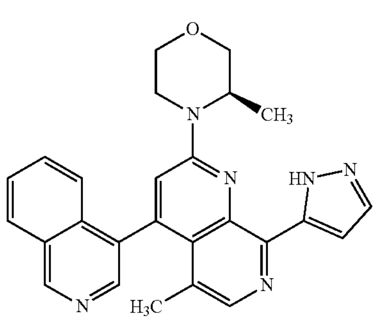 [SMILES: Cc1cnc(-c2ccn[nH]2)c2nc(N3CCOC[C@H]3C)cc(-c3cncc4ccccc34)c12] | 0.85 | 436.5 | 437.5 | 5 |

-continued

| Example | Structure | Retention Time [min] | Mol Weight (calc) | Mol Weight (found) | Method |
|---------|-----------|----------------------|-------------------|--------------------|--------|
| 59 | 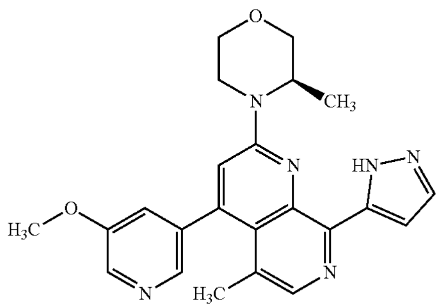 [SMILES: COc1cncc(-c2cc(N3CCOC[C@H]3C)nc3c(-c4ccn[nH]4)ncc(C)c23)c1] | 0.80 | 416.5 | 417.5 | 5 |
| 60 | 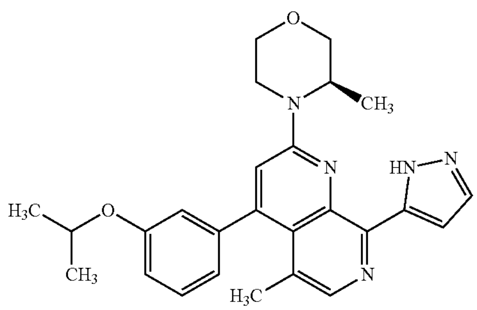 [SMILES: Cc1cnc(-c2ccn[nH]2)c2nc(N3CCOC[C@H]3C)cc(-c3cccc(OC(C)C)c3)c12] | 1.10 | 443.5 | 444.5 | 5 |
| 61 | 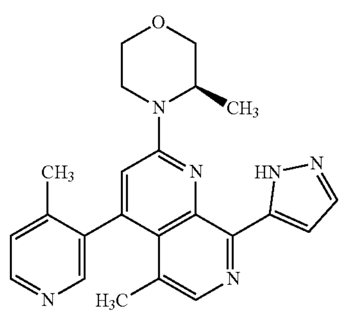 [SMILES: Cc1ccncc1-c1cc(N2CCOC[C@H]2C)nc2c(-c3ccn[nH]3)ncc(C)c12] | 0.71 | 400.5 | 401.5 | 5 |
| 62 | 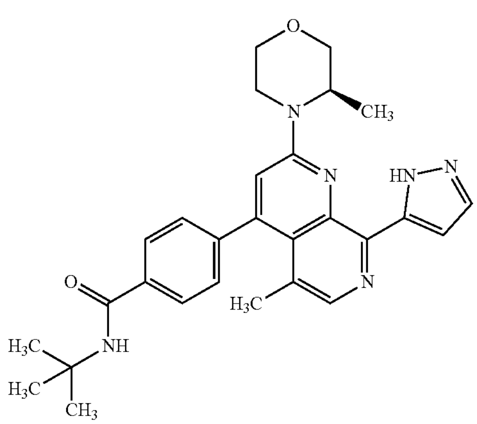 [SMILES: Cc1cnc(-c2ccn[nH]2)c2nc(N3CCOC[C@H]3C)cc(-c3ccc(C(=O)NC(C)(C)C)cc3)c12] | 0.97 | 484.6 | 485.6 | 5 |

-continued

| Example | Structure | Retention Time [min] | Mol Weight (calc) | Mol Weight (found) | Method |
|---------|-----------|----------------------|-------------------|--------------------|--------|
| 63 | 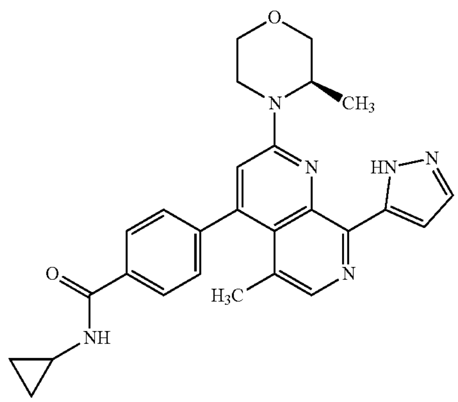 [SMILES: Cc1cnc(-c2ccn[nH]2)c2nc(N3CCOC[C@H]3C)cc(-c3ccc(C(=O)NC4CC4)cc3)c12] | 0.82 | 468.6 | 469.6 | 5 |
| 64 | 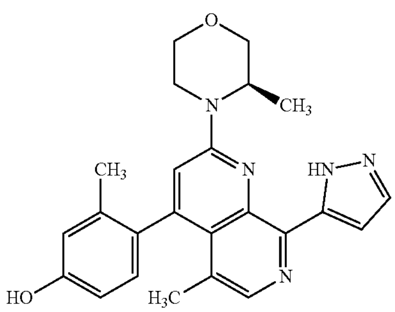 [SMILES: Cc1cc(O)ccc1-c1cc(N2CCOC[C@H]2C)nc2c(-c3ccn[nH]3)ncc(C)c12] | 0.84 | 415.5 | 416.5 | 5 |
| 65 | 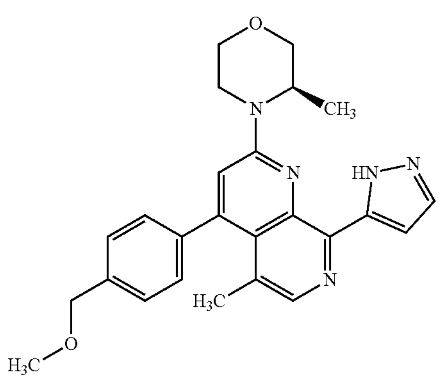 [SMILES: COCc1ccc(-c2cc(N3CCOC[C@H]3C)nc3c(-c4ccn[nH]4)ncc(C)c23)cc1] | 0.95 | 429.5 | 430.5 | 5 |
| 66 | 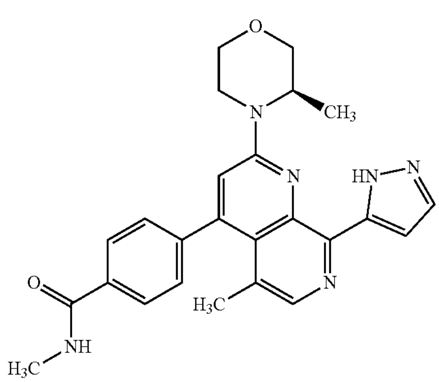 [SMILES: CNC(=O)c1ccc(-c2cc(N3CCOC[C@H]3C)nc3c(-c4ccn[nH]4)ncc(C)c23)cc1] | 0.76 | 442.5 | 443.5 | 5 |

The examples in the aforegoing table bear the names given in the following table:

| Example | Name |
|---|---|
| 20 | 5-methyl-2-[(3R)-3-methylmorpholin-4-yl]-4-phenyl-8-(1H-pyrazol-5-yl)-1,7-naphthyridine |
| 21 | 4-(2,3-dihydro-1,4-benzodioxin-6-yl)-5-methyl-2-[(3R)-3-methylmorpholin-4-yl]-8-(1H-pyrazol-5-yl)-1,7-naphthyridine |
| 22 | 4-(2,4-dichlorophenyl)-5-methyl-2-[(3R)-3-methylmorpholin-4-yl]-8-(1H-pyrazol-5-yl)-1,7-naphthyridine |
| 23 | (3-{5-methyl-2-[(3R)-3-methylmorpholin-4-yl]-8-(1H-pyrazol-5-yl)-1,7-naphthyridin-4-yl}phenyl)methanol |
| 24 | 4-(4-fluorophenyl)-5-methyl-2-[(3R)-3-methylmorpholin-4-yl]-8-(1H-pyrazol-5-yl)-1,7-naphthyridine |
| 25 | 4-(4-methoxyphenyl)-5-methyl-2-[(3R)-3-methylmorpholin-4-yl]-8-(1H-pyrazol-5-yl)-1,7-naphthyridine |
| 26 | 5-methyl-2-[(3R)-3-methylmorpholin-4-yl]-8-(1H-pyrazol-5-yl)-4-(2,3,5-trifluorophenyl)-1,7-naphthyridine |
| 27 | 4-(6-methoxypyridin-3-yl)-5-methyl-2-[(3R)-3-methylmorpholin-4-yl]-8-(1H-pyrazol-5-yl)-1,7-naphthyridine |
| 28 | methyl 3-{5-methyl-2-[(3R)-3-methylmorpholin-4-yl]-8-(1H-pyrazol-5-yl)-1,7-naphthyridin-4-yl}benzoate |
| 29 | 5-methyl-2-[(3R)-3-methylmorpholin-4-yl]-4-[4-(methylsulfinyl)phenyl]-8-(1H-pyrazol-5-yl)-1,7-naphthyridine |
| 30 | 4-(2-fluoro-3-methoxyphenyl)-5-methyl-2-[(3R)-3-methylmorpholin-4-yl]-8-(1H-pyrazol-5-yl)-1,7-naphthyridine |
| 31 | 5-methyl-2-[(3R)-3-methylmorpholin-4-yl]-4-[2-(methylsulfonyl)phenyl]-8-(1H-pyrazol-5-yl)-1,7-naphthyridine |
| 32 | N-(4-{5-methyl-2-[(3R)-3-methylmorpholin-4-yl]-8-(1H-pyrazol-5-yl)-1,7-naphthyridin-4-yl}phenyl)methanesulfonamide |
| 33 | 4-(cyclopent-1-en-1-yl)-5-methyl-2-[(3R)-3-methylmorpholin-4-yl]-8-(1H-pyrazol-5-yl)-1,7-naphthyridine |
| 34 | 5-methyl-2-[(3R)-3-methylmorpholin-4-yl]-8-(1H-pyrazol-5-yl)-4-(quinolin-3-yl)-1,7-naphthyridine |
| 35 | N,N-dimethyl-4-{5-methyl-2-[(3R)-3-methylmorpholin-4-yl]-8-(1H-pyrazol-5-yl)-1,7-naphthyridin-4-yl}benzamide |
| 36 | 4-(4-chloro-3-methylphenyl)-5-methyl-2-[(3R)-3-methylmorpholin-4-yl]-8-(1H-pyrazol-5-yl)-1,7-naphthyridine |
| 37 | 4-(2,3-dimethoxyphenyl)-5-methyl-2-[(3R)-3-methylmorpholin-4-yl]-8-(1H-pyrazol-5-yl)-1,7-naphthyridine |
| 38 | 4-(4-chloro-2-methoxyphenyl)-5-methyl-2-[(3R)-3-methylmorpholin-4-yl]-8-(1H-pyrazol-5-yl)-1,7-naphthyridine |
| 39 | 5-methyl-2-[(3R)-3-methylmorpholin-4-yl]-4-[4-(methylsulfanyl)phenyl]-8-(1H-pyrazol-5-yl)-1,7-naphthyridine |
| 40 | N,N-dimethyl-3-{5-methyl-2-[(3R)-3-methylmorpholin-4-yl]-8-(1H-pyrazol-5-yl)-1,7-naphthyridin-4-yl}aniline |
| 41 | 5-methyl-2-[(3R)-3-methylmorpholin-4-yl]-4-[3-(methylsulfonyl)phenyl]-8-(1H-pyrazol-5-yl)-1,7-naphthyridine |
| 42 | 4-(3,5-dimethoxyphenyl)-5-methyl-2-[(3R)-3-methylmorpholin-4-yl]-8-(1H-pyrazol-5-yl)-1,7-naphthyridine |
| 43 | 5-methyl-2-[(3R)-3-methylmorpholin-4-yl]-8-(1H-pyrazol-5-yl)-4-(quinolin-4-yl)-1,7-naphthyridine |
| 44 | 4-(1H-indol-4-yl)-5-methyl-2-[(3R)-3-methylmorpholin-4-yl]-8-(1H-pyrazol-5-yl)-1,7-naphthyridine |
| 45 | 4-(1H-indol-6-yl)-5-methyl-2-[(3R)-3-methylmorpholin-4-yl]-8-(1H-pyrazol-5-yl)-1,7-naphthyridine |
| 46 | 5-methyl-2-[(3R)-3-methylmorpholin-4-yl]-4-(3-methylpyridin-4-yl)-8-(1H-pyrazol-5-yl)-1,7-naphthyridine |
| 47 | (5-{5-methyl-2-[(3R)-3-methylmorpholin-4-yl]-8-(1H-pyrazol-5-yl)-1,7-naphthyridin-4-yl}thiophen-2-yl)methanol |
| 48 | 2-fluoro-4-{5-methyl-2-[(3R)-3-methylmorpholin-4-yl]-8-(1H-pyrazol-5-yl)-1,7-naphthyridin-4-yl}benzonitrile |
| 49 | 4-(6-fluoropyridin-3-yl)-5-methyl-2-[(3R)-3-methylmorpholin-4-yl]-8-(1H-pyrazol-5-yl)-1,7-naphthyridine |
| 50 | 4-(2-methoxypyridin-3-yl)-5-methyl-2-[(3R)-3-methylmorpholin-4-yl]-8-(1H-pyrazol-5-yl)-1,7-naphthyridine |
| 51 | 5-methyl-2-[(3R)-3-methylmorpholin-4-yl]-4-[2-(propan-2-yl)phenyl]-8-(1H-pyrazol-5-yl)-1,7-naphthyridine |
| 52 | 4-{5-methyl-2-[(3R)-3-methylmorpholin-4-yl]-8-(1H-pyrazol-5-yl)-1,7-naphthyridin-4-yl}benzamide |
| 53 | (4-{5-methyl-2-[(3R)-3-methylmorpholin-4-yl]-8-(1H-pyrazol-5-yl)-1,7-naphthyridin-4-yl}phenyl)(pyrrolidin-1-yl)methanone |
| 54 | N-benzyl-4-{5-methyl-2-[(3R)-3-methylmorpholin-4-yl]-8-(1H-pyrazol-5-yl)-1,7-naphthyridin-4-yl}benzamide |
| 55 | N,N-dimethyl-3-{5-methyl-2-[(3R)-3-methylmorpholin-4-yl]-8-(1H-pyrazol-5-yl)-1,7-naphthyridin-4-yl}benzamide |
| 56 | 4-[3-(methoxymethyl)phenyl]-5-methyl-2-[(3R)-3-methylmorpholin-4-yl]-8-(1H-pyrazol-5-yl)-1,7-naphthyridine |
| 57 | 5-methyl-4-(1-methyl-1H-indol-5-yl)-2-[(3R)-3-methylmorpholin-4-yl]-8-(1H-pyrazol-5-yl)-1,7-naphthyridine |

| Example | Name |
|---|---|
| 58 | 4-(isoquinolin-4-yl)-5-methyl-2-[(3R)-3-methylmorpholin-4-yl]-8-(1H-pyrazol-5-yl)-1,7-naphthyridine |
| 59 | 4-(5-methoxypyridin-3-yl)-5-methyl-2-[(3R)-3-methylmorpholin-4-yl]-8-(1H-pyrazol-5-yl)-1,7-naphthyridine |
| 60 | 5-methyl-2-[(3R)-3-methylmorpholin-4-yl]-4-[3-(propan-2-yloxy)phenyl]-8-(1H-pyrazol-5-yl)-1,7-naphthyridine |
| 61 | 5-methyl-2-[(3R)-3-methylmorpholin-4-yl]-4-(4-methylpyridin-3-yl)-8-(1H-pyrazol-5-yl)-1,7-naphthyridine |
| 62 | N-tert-butyl-4-{5-methyl-2-[(3R)-3-methylmorpholin-4-yl]-8-(1H-pyrazol-5-yl)-1,7-naphthyridin-4-yl}benzamide |
| 63 | N-cyclopropyl-4-{5-methyl-2-[(3R)-3-methylmorpholin-4-yl]-8-(1H-pyrazol-5-yl)-1,7-naphthyridin-4-yl}benzamide |
| 64 | 3-methyl-4-{5-methyl-2-[(3R)-3-methylmorpholin-4-yl]-8-(1H-pyrazol-5-yl)-1,7-naphthyridin-4-yl}phenol |
| 65 | 4-[4-(methoxymethyl)phenyl]-5-methyl-2-[(3R)-3-methylmorpholin-4-yl]-8-(1H-pyrazol-5-yl)-1,7-naphthyridine |
| 66 | N-methyl-4-{5-methyl-2-[(3R)-3-methylmorpholin-4-yl]-8-(1H-pyrazol-5-yl)-1,7-naphthyridin-4-yl}benzamide |

The title compounds described in the example section were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Expression of ATR/ATRIP in HEK 293-6E Cells:

The cDNAs encoding the protein sequences of full-length human ATR sequence (Q13535) with an N-terminally fused Flag tag as well as the full-length human ATRIP (Q8WXE1) were optimized for expression in eukaryotic cells and synthesized by the GeneArt Technology at Life Technologies. Both cDNAs also encoded att-site sequences at the 5' and 3' ends for subcloning into the following destination vectors using the Gateway Technology: pD-MamA (an in-house derivate of the vector pEAK from EdgeBioSystems but with a human CMV promotor) which provides a N-terminal fusion of a GST-tag to the integrated gene of interest; pD-MamB (an in-house derivative of pTT5 from NRCC, Y. Durocher) which provides a N-terminal fusion of a STREP II-tag to the integrated gene. The cDNAs of ATR and ATR-DN were cloned into pD-MamA and the ATRIP-FL into pD-MamB. The cDNA sequence of codon-optimized ATR including a GST tag is described in SEQ ID No. 1 of the attached sequence listing, its corresponding protein sequence in SEQ ID No. 3.

The cDNA sequence of codon-optimized ATRIP including a STREP II tag is described in SEQ ID No. 2, its corresponding protein sequence in SEQ ID No. 4.

Coexpression of ATR and ATRIP by Transient Transfection in HEK293-6E Cells:

For transient transfection of HEK293-6E suspension cells a Biostat Cultibag Bioreactor with 5 L culture volume (starting volume) in a 20 L culture bag was used. The cells were cultured in F17 Medium (Gibco, Invitrogen, Cat #05-0092DK) with the following supplements Pluronic F68 (10 mL/L of 10% solution, Gibco #24040), Gluta-Max (20 ml of 100× solution/L, L-Alanyl-Glutamine (200 mM, Invitrogen #25030), G418 (final concentration 25 µg/ml, PAA # P02-012). The applied culture conditions were 37° C., rocking rate 18 rpm, pH 7.0, pO2 55%. At the day of transfection the cell culture had reached a cell density of $1.6 \times 10^6$ cells/mL and a viability of 99%. For preparation of the transfection solution to 500 mL F17 medium (without the supplements) 4 mg of the ATR encoding plasmid, 1 mg of the ATRIP encoding plasmid and 10 mg PEI (Polyethylenimin, linear, Polysciences #23966, as 1 mg/mL stock solution) were subsequently added, carefully mixed and incubated at room temperature for 15 min. This transfection solution was then added to the 5 L cell culture in the culture bag. This cell culture was incubated for 5 h and afterwards 5 L of F17 medium with the mentioned supplements were added and the rocking rate increased to 19 rpm. 48 h after transfection the cells were harvested by centrifugation (30 min., 1000 g, 15° C.) and the cell pellets stored at −80° C.

Purification:

Purification of the ATR (Flag-Tag)/ATRIP(Strep-Tag) complex was achieved by affinity chromatography using anti-FLAG-resin (Sigma, # A220).

Cells were harvested by centrifugation (4000×g) and lysed in buffer A (50 mM Tris-HCl pH 7.5; 150 mM NaCl, 5% Glycerol, 1 mM Na3VO4, 1 mM NaF, 10 mM-glycerophosphate, 1% Tween 20; 0.1% NP40; Complete with EDTA) for 1 h at 4° C. The supernatant (20.000×g) was than bound to Flag-Agarose and eluted after several washing steps using Buffer B (50 mM Tris-HCl pH7.4; 150 mM NaCl; 10% Glycerin, 200 µg/ml Flag Peptides from Sigma, # F3290). Elution fractions were aliquoted and shock frozen using liquid nitrogen. The final concentration of ATR in the final preparation was 250 µg/ml calculated densitometrically using BSA as a standard in a Coomassie stained gel. The yield of copurified ATRIP was far below a 1:1 ratio compared to ATR but was essential for ATR activity.

Tracer A

3',6'-bis(dimethylamino)-N-(4-{[2-(1H-indol-4-yl)-6-(morpholin-4-yl)pyrimidin-4-yl]amino}butyl)-3-oxo-3H-spiro[2-benzofuran-1,9'-xanthene]-5-carboxamide Step a tert-butyl (4-{[2-(1H-indol-4-yl)-6-(morpholin-4-yl)pyrimidin-4-yl]amino}butyl)carbamate

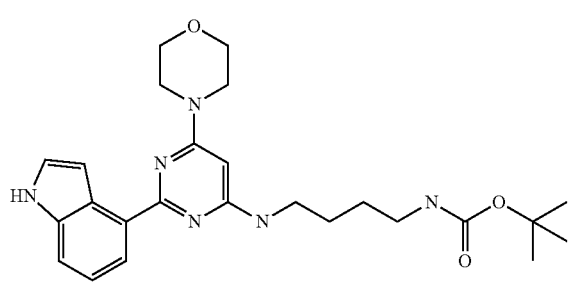 [SMILES: CC(C)(C)OC(=O)NCCCCNc1cc(N2CCOCC2)nc(-c2cccc3[nH]ccc23)n1]

The starting material 4-[4-chloro-6-(morpholin-4-yl)pyrimidin-2-yl]-1H-indole was synthesized according to the literature (WO2008/125833). A solution of 4-[4-chloro-6-(morpholin-4-yl)pyrimidin-2-yl]-1H-indole (980 mg, 3.11 mmol), diisopropylethylamine (805 mg, 1.09 ml, 6.23 mmol) and N—BOC-1,4-diaminobutane (879 mg, 4.67 mmol) in 1-methyl-2-pyrrolidinone (24.5 ml) was stirred overnight at 150° C. The mixture was allowed to cool to ambient temperature. Ethyl acetate (50 ml) and brine (50 ml) were added, the layers were separated and the organic layer was washed with brine (3×50 ml). The organic layer was dried over sodium sulphate and the solvent was removed under reduced pressure. The title compound was obtained as crude mixture (purity 40%, 2.37 g) and used without further purification in the next step.

Step b

N-[2-(1H-indol-4-yl)-6-(morpholin-4-yl)pyrimidin-4-yl]butane-1,4-diamine

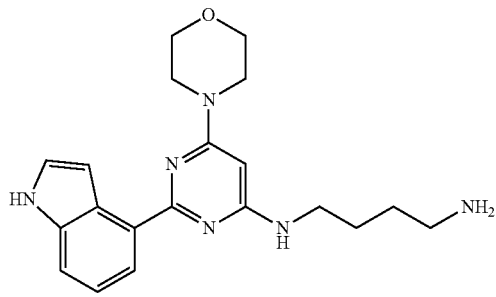 [SMILES: NCCCCNc1cc(N2CCOCC2)nc(-c2cccc3[nH]ccc23)n1]

Tert-butyl (4-{[2-(1H-indol-4-yl)-6-(morpholin-4-yl)pyrimidin-4-yl]amino}butyl)carbamate (2.37 g, 2.03 mmol) was dissolved in HCl/dioxane (4M, 20 ml) and stirred at ambient temperature for 10 minutes. Ethyl acetate (50 ml) and water (50 ml) were added and the phases separated. By addition of aqueous NaOH (2N, 50 ml) the pH of the aqueous layer was basified and extracted with ethyl acetate (2×50 ml). The combined organic layers were dried over sodium sulphate and the solvent was removed under reduced pressure. The title compound was obtained in 77% yield (770 mg) and used without further purification in the next step.

Step c

3',6'-bis(dimethylamino)-N-(4-{[2-(1H-indol-4-yl)-6-(morpholin-4-yl)pyrimidin-4-yl]amino}butyl)-3-oxo-3H-spiro[2-benzofuran-1,9'-xanthene]-6-carboxamide and 3',6'-bis(dimethylamino)-N-(4-{[2-(1H-indol-4-yl)-6-(morpholin-4-yl)pyrimidin-4-yl]amino}butyl)-3-oxo-3H-spiro[2-benzofuran-1,9'-xanthene]-5-carboxamide Isomer 1

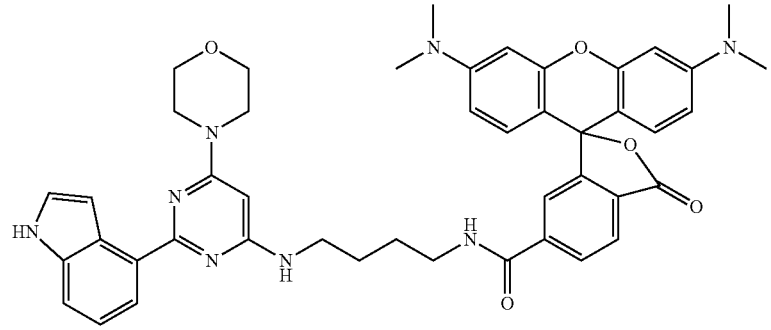

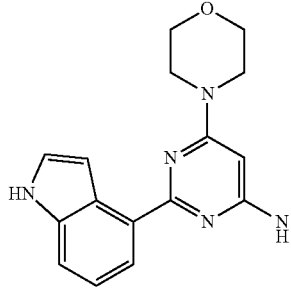
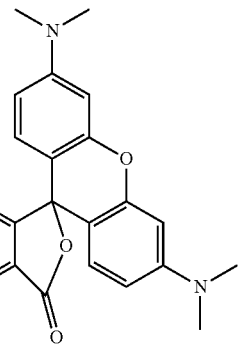

Isomer 2

N-[2-(1H-indol-4-yl)-6-(morpholin-4-yl)pyrimidin-4-yl]butane-1,4-diamine (70 mg, 0.14 mmol) was dissolved in DMF (3 mL). DIPEA (74 µl, 0.43 mmol, 3 eq.) and a mixture of commercially available 5-carboxytetramethylrhodamine N-succinimidyl ester and 6-carboxytetramethylrhodamine N-succinimidyl ester (75 mg, 0.14 mmol, 1 eq.) were added sequentially. The mixture was stirred for 15 minutes at ambient temperature and concentrated under reduced pressure. The two title compounds were separated by preparative HPLC (H$_2$O(NH$_4$OH)/CH$_3$CN: 85:15 to 45:55).

Isomer 1 was obtained in 22% yield (25 mg). $^1$H-NMR (300 MHz, DMSO-d$_6$): δ [ppm]: 1.56 (4H), 2.92 (12H), 3.49 (4H), 3.69 (4H), 5.53 (1H), 6.48 (6H), 6.74 (1H), 7.06 (1H), 7.33 (2H), 7.43 (1H), 7.63 (1H), 8.03 (2H), 8.15 (1H), 8.71 (1H), 11.11 (1H).

Isomer 2 was obtained in 34% yield (31 mg). $^1$H-NMR (400 MHz, DMSO-d$_6$): δ [ppm]: 1.67 (4H), 2.93 (12H), 3.38 (4H), 3.52 (4H), 3.71 (4H), 5.58 (1H), 6.47 (6H), 6.80 (1H), 7.09 (1H), 7.28 (1H), 7.36 (2H), 7.44 (1H), 8.02 (1H), 8.22 (1H), 8.44 (1H), 8.83 (1H).

Isomer 2 was used as ligand for the ATR binding assay which is described infra.

1. Binding Assay ATR

To determine of binding activity of the test compounds, full-length human ATR protein was expressed and purified together with ATRIP as described above. Furthermore, a fluorescently labelled compound (tracer A as described above) was used as a tracer molecule. Detection of the binding event of the tracer was achieved by time-resolved fluorescence energy transfer (TR-FRET). We used an anti-GST-Terbium antibody (CisBio) that binds to the GST-tag at the N-terminus of ATR-kinase. Excitation of Terbium with 337 nm light results in emission of fluorescent light with 545 nm. In case a tetrameric complex has formed (antiGST-Tb+GST-ATR+Strp2-ATRIP+tracer), part of the energy will be transferred from the Terbium to the fluorophore that itself emits light of 570 nm. Displacement of the fluorescent tracer by a test compound leads to a reduction of the TR-FRET-signal.

For the assay 50 nl of a 100-fold concentrated solution of the test compound in DMSO was pipetted into a black low volume 384 well microtiter plate (MTP, Greiner Bio-One, Frickenhausen, Germany). To prepare the ATR-working solution, ATR/ATRIP stock solution was diluted in assay buffer [50 mM HEPES (pH 7.0), 10 mM MgCl2, 1 mM DTT, 0.01% (w/v) Igepal, 0.01% (w/v) BSA] to 4.2 nM protein concentration (concentration may vary from lot to lot of protein preparation). AntiGST-Tb antibody was diluted to 4.2 nM. The ATR-working solution was incubated for 30 min at 22° C. prior to dispensing to pre-form the complex of antiGST-Tb+GST-ATR+ATRIP. Then, 3 µl of the ATR-working solution were added to the test compound and the mixture was incubated for 10 min at 22° C. to allow pre-binding of the test compounds to ATR/ATRIP. Then, 2 µl of a 100 nM solution of tracer A in assay buffer were added to the ATR-working solution. The resulting mixture was incubated for 30 min at 22° C. The measurement of the TR-FRET signal was performed in a standard HTRF-compatible MTP reader instrument (e.g. BMG Pherastar) by recording the fluorescence emissions at 545 nm and 570 nm after excitation at 337-350 nm. The ratio between emission at 570 nm divided by emission at 545 nm was calculated to give the well ratio. The experimental data (well ratios) were normalised by the following way: positive control contained ATR-working solution plus tracer A solution (=0% inhibition), the negative control contained all components except GST-ATR/ATRIP (=100% inhibition). Usually the compounds were tested on the same MTP in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM). The dilution series were prepared separately before the assay on the level of the 100 fold concentrated solutions in DMSO by serial 1:3.4 dilutions in duplicate values for each concentration. IC$_{50}$ values were calculated by a 4 parameter fit using standard software (GraphPad prism or equivalent).

Atr Binding:

| Example | ATR binding (tracer A) IC$_{50}$ [M] |
|---|---|
| 1 | 2.59E−8 |
| 2 | 6.02E−9 |
| 3 | 8.13E−9 |
| 4 | 3.73E−8 |
| 5 | 5.07E−9 |
| 6 | 1.42E−8 |
| 7 | 8.27E−9 |
| 8 | 3.55E−8 |
| 9 | 1.41E−8 |
| 10 | 8.91E−9 |
| 11 | 3.80E−9 |
| 12 | 5.49E−9 |
| 13 | 4.93E−9 |
| 14 | 5.30E−8 |
| 15 | 5.86E−9 |
| 16 | 1.42E−8 |
| 17 | 4.22E−8 |
| 18 | 6.64E−8 |
| 19 | 3.49E−8 |
| 20 | 2.44E−8 |

-continued

| Example | ATR binding (tracer A) IC$_{50}$ [M] |
|---|---|
| 21 | 1.79E−8 |
| 22 | 1.64E−8 |
| 23 | 1.40E−8 |
| 24 | 3.47E−8 |
| 25 | 2.54E−8 |
| 26 | 1.12E−8 |
| 27 | 1.54E−8 |
| 29 | 2.91E−8 |
| 30 | 1.75E−8 |
| 31 | 4.72E−8 |
| 32 | 4.31E−9 |
| 33 | 2.65E−8 |
| 34 | 3.38E−8 |
| 35 | 2.88E−8 |
| 36 | 4.56E−7 |
| 37 | 1.38E−8 |
| 38 | 4.79E−8 |
| 39 | 3.19E−8 |
| 40 | 3.43E−8 |
| 41 | 2.49E−8 |
| 42 | 1.12E−7 |
| 43 | 3.60E−8 |
| 44 | 3.55E−8 |
| 45 | 9.47E−8 |
| 46 | 7.78E−9 |
| 47 | 4.09E−9 |
| 48 | 2.32E−8 |
| 49 | 2.86E−8 |
| 50 | 7.22E−8 |
| 52 | 3.02E−8 |
| 53 | 2.73E−8 |
| 54 | 3.46E−8 |
| 55 | 4.06E−8 |
| 56 | 6.24E−8 |
| 57 | 5.00E−8 |
| 58 | 4.00E−8 |
| 59 | 4.26E−8 |
| 60 | 1.32E−7 |
| 61 | 8.60E−9 |
| 62 | 1.82E−8 |
| 63 | 7.87E−9 |
| 65 | 1.23E−8 |
| 66 | 1.29E−8 |

2. ATR Activity Assay

ATR kinase phosphorylates a biotinylated peptide derived from Rad17 (sequence: biotin-PEG2-ASELPASQPQPFS-amide, produced by Biosyntan GmbH, Berlin). The assay measures the amount of phosphorylated peptide by time-resolved fluorescence (TR-FRET). Streptavidin-XL665 (Cisbio, reference #610SAXLB), an anti-Rad17-phosphoserine 645 specific antibody (available from either Imgenex/Biomol, reference # IMG-6386A, or from Lifespan, reference # LS-C43028) and antiRabbit-lgG-Europium (Perkin Elmer, reference # AD0083) are employed to specifically detect phosphorylated biotin-peptide, but not non-phosphorylated peptide. Excitation of Europium with 337 nm light results in emission of fluorescent light with 620 nm. In case a tetrameric detection complex has formed, part of the energy will be transferred to the Streptavidin-XL665 fluorophor that itself emits light of 665 nm. Unphosphorylated peptide does not give rise to light emission at 665 nm, because no FRET-competent detection complex can be formed.

For the assay 50 nl of a 100-fold concentrated solution of the test compound in DMSO was pipetted into a black low volume 384 well microtiter plate (MTP, Greiner Bio-One, Frickenhausen, Germany). To prepare the ATR-working solution, ATR/ATRIP stock solution (expression and purification: see above) was diluted in assay buffer [50 mM HEPES (pH 7.0), 10 mM MgCl2, 1 mM dithiothreitol (DTT), 0.01% (w/v) Igepal, 0.2% (w/v) bovine gamma globulin (BGG)] to 10 nM protein concentration (concentration may vary from lot to lot of protein preparation). A substrate working solution was prepared by diluting the biotinylated Rad17 peptide to 0.51 µM together with ATP to 201 µM in assay buffer. A stop/detection working solution was prepared containing 50 mM Hepes pH 7.0, 0.15% (w/v) bovine serum albumin (BSA), 150 mM EDTA, 200 nM Streptavidin-XL665, 2.5 nM anti phospho Rad17-pS645 (IMG-6386A) and 1.5 nM anti-Rabbit-IgG-Eu. The amount of the antibodies is dependent on the batch used and was optimized by variation the activity of the batch. All solutions were kept at 20° C. First, 2.5 µl of ATR-working solution were dispensed into the wells of the MTP containing the test compounds. After 10 minutes pre-incubation to allow binding of the compounds to ATR, 2.5 µl of substrate working solution was dispensed to the wells. After 180 minutes, 5 µl of stop/detection solution were dispensed into the wells. The resulting mixture was incubated for 60 min at 20° C. The measurement of the TR-FRET signal was performed in a standard HTRF-compatible MTP reader instruments (e.g. BMG Pherastar or Perkin Elmer ViewLux) by recording the fluorescence emissions at 620 nm and 665 nm after excitation at 337-350 nm. The ratio between emission at 665 nm divided by emission at 620 nm was calculated to give the well ratio. The experimental data (well ratios) were normalised by the following way: positive control was composed of ATR-working solution+substrate solution (=0% inhibition), the negative control contains the same reagents, but ATR-working solution is replaced by assay buffer (=100% inhibition). Usually the compounds were tested on the same MTP in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM) The dilution series were prepared separately before the assay on the level of the 100 fold concentrated solutions in DMSO by serial 1:3.4 dilutions in duplicate values for each concentration. IC$_{50}$ values were calculated by a 4 parameter fit using with standard software (GraphPad prism or equivalent).

3. Proliferation Assay

Human tumour cells were originally obtained from the American Type Culture Collection (ATCC), the Deutsche Sammlung von Mikroorganismen und Zellkulturen (DSMZ, German Collection of Microorganisms and Cell Cultures) or Epo GmbH, Berlin.

Adherently growing cells (HeLa, HeLa-MaTu-ADR, HT-144, Lovo, HT-29, NCI-H460, DU145, Caco2, B16F10) were plated out in a density of 1500-4000 cells/measurement point, depending on the rate of growth of the cell line, in a 96-well multititre plate in 200 µl of growth medium (DMEM/HAMS F12, 2 mM L-glutamine, 10% foetal calf serum). After 24 hours, the cells of one plate (zero plate) were dyed with crystal violet (see below), whereas the medium of the other plates was replaced with fresh culture medium (200 µl) to which the test substances were added in various concentrations (0 µM, and also in the range of 0.001-10 µM; the final concentration of the solvent dimethyl sulphoxide was 0.1 or 0.5%). The cells were incubated for 4 days in the presence of the test substances. Cell proliferation was determined by staining the cells with crystal violet: the cells were fixed at room temperature for 15 min by adding 20 µl/measurement point of an 11% strength glutaraldehyde solution. After washing the fixed cells three times with water, the plates were dried at room temperature. The cells were stained by adding 100 µl/measurement point of a 0.1% strength crystal violet solution (pH adjusted to pH 3 by adding acetic acid). After washing the cells three times with water, the plates were dried at room temperature. The dye was dissolved by adding 100 μl/measurement point of a 10% strength acetic acid solution. Absorbance was determined photometrically at a wavelength of 595 nm. The percentage change in cell growth was calculated by normalizing the measured values to the absorbance values of the zero plate (=0%) and the absorbance of the untreated (0 μM) cells (=100%). The $IC_{50}$ values were determined by means of a four parameter fit.

Cells growing in suspension (GRANTA-519, Jeko-1) were plated out in a cell density of 2000-4000 cells/measurement point, depending on the rate of growth of the cell line, in a black-walled, clear-bottom 96-well multititre plate in 100 μl of growth medium (DMEM/HAMS F12, 2 mM L-glutamine, 10% foetal calf serum). After 24 hours, cell density was determined in one plate (zero plate) by adding 60 μl/measurement point of CTG solution (Promega Cell Titer-Glo solution (catalogue numbers G755B and G756B)), subsequent incubation for 2 min followed by 10 min shaking (in the dark) and measurement of luminescence (VICTOR V, Perkin Elmer).

For the test plates, the test substances were prepared in various concentrations (0 μM, and also in the range of 0.001-10 μM; the final concentration of the solvent dimethyl sulphoxide was 0.1 or 0.5%) as 3× concentrated solutions in fresh growth medium. Aliquots of 50 μl each were added to the cell suspensions and the cells were incubated for 4 days in the presence of the test substances. Subsequently, cell density was determined using CTG solution as described above and $IC_{50}$ values were calculated by means of a four parameter fit.

The substances were investigated in the following cell lines, which, by way of example, represent the specified indications.

List of the Cell Lines Investigated in the Proliferation Assays.

| Tumour indication | Cell line | Source |
|---|---|---|
| Cervical cancer | HeLa | DSMZ ACC-57 |

The results of the proliferation assays demonstrate the efficacy of test compounds in the human tumour cells investigated. These data suggest a possible use of the test compounds in the tumour types investigated.

Inhibition of proliferation of HeLa cells by compounds according to the present invention, determined as described above. All $IC_{50}$ (inhibitory concentration at 50% of maximal effect) values are indicated in M, "n.t." means that the compounds have not been tested in the respective assay.

| Example | Inhibition of HeLa cell proliferation |
|---|---|
| 01 | 4.98E−7 |
| 02 | 6.34E−8 |
| 03 | 1.54E−7 |
| 04 | 3.33E−7 |
| 05 | 8.51E−8 |
| 06 | 2.96E−7 |
| 07 | 4.99E−7 |
| 08 | 4.73E−7 |
| 09 | 1.17E−7 |
| 10 | 1.09E−7 |
| 11 | 3.32E−8 |
| 12 | 4.40E−7 |
| 13 | 7.45E−7 |
| 14 | 4.40E−7 |
| 15 | 1.45E−7 |
| 16 | 3.39E−8 |
| 17 | 1.12E−7 |

4. Phospho-H2AX Assay

Phospho-Ser139 Histone H2AX (also known as ☒ H2AX, UniProtKB/Swiss-Prot P16104) represents an cellular early marker for DNA damage response. In particular, H2AX gets phosphorylated by ATR upon DNA replication stress. HT-29 human colorectal adenoadenocarcinoma cells, originally obtained from the DSMZ, were plated out in a density of 12000 cells/measurement point a black-walled, clear-bottom 96-well multititre plate in 100 μl of growth medium (DMEM/HAMS F12, 2 mM L-glutamine, 10% foetal calf serum). After 24 hours, the test substances were added in various concentrations (0 μM, and also in the range of 0.001-10 μM in quadruplicates; the final concentration of the solvent dimethyl sulphoxide was 0.1%) followed by addition of a hydroxyurea solution to achieve a finale concentration of 2.5 mM and a final assay volume of 200 μL. One control plate was left untreated and further processed in parallel. The cells were incubated for 30 min at 37° C. Subsequently, the growth medium was carefully evaporated and the cells were fixed with 50 μL/well of ice-cold methanol for 15 min. The cells were washed once with 100 μL/well of PBS, followed by incubation with 50 μL/well of blocking buffer (Liqor, 927-40000) for 1 h at room temperature. Subsequently, the cells were incubated with 50 μL/well of anti-phospho-H2AX (Ser 139) antibody (Merck Millipore, clone JBW301, 05-636) diluted 1:500 in blocking buffer for 1 h at room temperature (or over night at 4° C.). The cells were washed three time with 100 μL/well of PBS, followed by incubation with 50 μL/well of a 1:500 diluted solution of Alexa Fluor 488 conjugated donkey anti-mouse IgG antibody (Life Technologies, A-21202) in TBST for 1 h at room temperature and protected from light. After the cells were washed three time with 100 μL/well of PBS, the wells were filled with 100 μL of PBS and fluorescence was determined using an Acumen laser scanning cytometer (TTP Labtech). The percentage change in hydroxy urea induced phospho-H2AX content was calculated by normalizing the measured values to the fluorescence values of untreated control wells (=0%) and the fluorescence of the hydroxy urea control wells without test compounds (0 μM, =100%). The $IC_{50}$ values were determined by means of a four parameter fit.

5. Caco-2 Permeation Assay

Caco-2 cells (purchased from DSMZ Braunschweig, Germany) were seeded at a density of 4.5×104 cell per well on 24 well insert plates, 0.4 μm pore size, and grown for 15 days in DMEM medium supplemented with 10% fetal bovine serum, 1% GlutaMAX (100×, GIBCO), 100 U/ml penicillin, 1001 g/ml streptomycin (GIBCO) and 1% non essential amino acids (100×). Cells were maintained at 37° C. in a humified 5% CO2 atmosphere. Medium was changed every 2-3 day.

Before running the permeation assay, the culture medium was replaced by a FCS-free hepes-carbonate transport puffer (pH 7.2) For assessment of monolayer integrity the transepithelial electrical resistance (TEER) was measured. Test compounds were predissolved in DMSO and added either to the apical or basolateral compartment in final concentration of 2 μM. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$Papp=(Vr/Po)(1/S)(P2/t)$$

Where Vr is the volume of medium in the receiver chamber, Po is the measured peak area of the test drug in the donor chamber at t=o, S the surface area of the monolayer, P2 is the measured peak area of the test drug in the acceptor chamber after 2 h of incubation, and t is the incubation time. The efflux ratio basolateral (B) to apical (A) was calculated by dividing the Papp B-A by the Papp A-B. In addition the compound recovery was calculated. As assay control reference compounds were analyzed in parallel.

The invention claimed is:

1. A compound of formula (I)

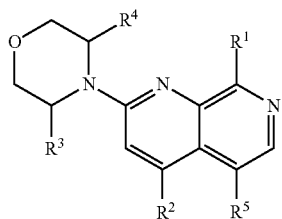

(I)

wherein

R¹ is a group selected from:

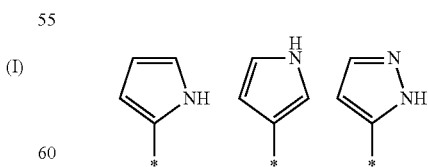

wherein * indicates the point of attachment of said group with the rest of the molecule;

R² is hydrogen, —NR⁷R⁸, CN, $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, $C_4$-$C_6$-cycloalkenyl, 3- to 10-membered heterocycloalkyl, 4- to 10-membered heterocycloalkenyl, phenyl, heteroaryl, —(CO)OR$^7$, —(CO)NR$^7$R$^8$, —(SO$_2$)R$^9$, —(SO)R$^9$, —SR$^9$, —(SO$_2$)NR$^7$R$^8$, —NR$^7$(SO$_2$)R$^9$, —((SO)=NR$^{11}$)R$^{10}$, —N=(SO)R$^9$R$^{10}$, —SiR$^{10}$R$^{11}$R$^{12}$, —(PO)(OR$^7$)$_2$, —(PO)(OR$^7$)R$^{10}$ or —(PO)(R$^{10}$)$_2$,
  wherein each C$_1$-C$_6$-alkyl, C$_1$-C$_6$-alkoxy, 3- to 10-membered heterocycloalkoxy, C$_2$-C$_6$-alkenyl, C$_3$-C$_6$-cycloalkyl, 3- to 10-membered heterocycloalkyl, phenyl or heteroaryl is optionally substituted, one or more times, independently from each other, with halogen, OH, —CN, —NR$^7$R$^8$, C$_1$-C$_6$-alkyl, C$_1$-C$_6$-haloalkyl, C$_1$-C$_4$-hydroxyalkyl, phenyl-C$_1$-C$_4$-alkyl, (C$_1$-C$_4$-alkoxy)-(C$_1$-C$_4$-alkyl)-, C$_1$-C$_6$-alkoxy, C$_3$-C$_6$-cycloalkyl, 3- to 6-membered heterocycloalkyl, phenyl, —(CO)OR$^7$, —(CO)NR$^7$R$^8$, —NR$^7$(CO)R$^{10}$, —NR$^8$(CO)OR$^7$, —NR$^8$(CO) NR$^7$R$^8$, —(SO$_2$)R$^9$, —(SO)R$^9$, —SR$^9$, —(SO$_2$)NR$^7$R$^8$, —NR$^7$(SO$_2$)R$^9$, —((SO)=NR$^{11}$)R$^{10}$, —N=(SO)R$^9$R$^{10}$, —(PO)(OR$^7$)$_2$, —(PO)(OR$^7$)R$^{10}$, —(PO)(R$^{10}$)$_2$, with a heteroaryl group which is optionally substituted one or more times with C$_1$-C$_4$-alkyl, or
  wherein two substituents of said phenyl group attached to two adjacent phenyl ring atoms are linked to one another to jointly form a methylenedioxy, ethylenedioxy, ethyleneoxy or trimethyleneoxy group;
  wherein each 4- to 10-membered heterocycloalkenyl is optionally substituted, one or more times, independently from each other, with C$_1$-C$_4$-alkyl;
R$^3$ and R$^4$ are independently hydrogen or methyl;
R$^5$ is C$_1$-C$_6$-alkyl, C$_1$-C$_6$-haloalkyl or C$_1$-C$_6$-alkoxy;
R$^7$ and R$^8$ are independently hydrogen, C$_1$-C$_6$-alkyl, C$_3$-C$_6$-cycloalkyl, phenyl or phenyl-CH$_2$—, which phenyl is optionally substituted, one or more times, with halogen; or R$^7$ and R$^8$ together represent a 4-, 5-, 6- or 7-membered cyclic amine group, which is optionally substituted, one or more times, independently from each other, with a substituent selected from C$_1$-C$_6$-alkyl, C$_1$-C$_6$-haloalkyl, said 4-, 5-, 6- or 7-membered cyclic amine group optionally containing one further heteroatom selected from the group consisting of O, N and S;
R$^9$ is C$_1$-C$_4$-alkyl or phenyl, wherein each C$_1$-C$_4$-alkyl or phenyl is optionally substituted, one or more times, independently from each other, with R$^{13}$;
R$^{10}$ is C$_1$-C$_4$-alkyl; or
R$^9$ and R$^{10}$ together, in case of —N=(SO)R$^9$R$^{10}$ group, represent a 5- to 8-membered heterocycloalkyl group;
R$^{11}$ is hydrogen, C$_1$-C$_4$-alkyl, —(CO)OR$^7$, —(CO)NR$^7$R$^8$ or CN;
R$^{12}$ is hydrogen or C$_1$-C$_4$-alkyl; and
R$^{13}$ is halogen, OH, —NR$^7$R$^8$, CN, NO$_2$, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, C$_3$-C$_6$-cycloalkyl, —(CO)OR$^7$ or —(CO)NR$^7$R$^8$,
or a stereoisomer, a tautomer, an N-oxide, a hydrate, a solvate, or a salt thereof, or a mixture of same.

2. The compound of formula (I) according to claim 1, wherein:
R$^1$ is a group:

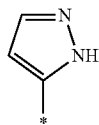

wherein * indicates the point of attachment of said group with the rest of the molecule;

R$^2$ is hydrogen, —NR$^7$R$^8$, CN, C$_1$-C$_4$-alkyl, C$_1$-C$_4$-alkoxy, 3- to 6-membered heterocycloalkoxy, C$_3$-C$_6$-cycloalkyl, C$_4$-C$_6$-cycloalkenyl, 3- to 6-membered heterocycloalkyl, phenyl, heteroaryl, —(CO)OR$^7$, —(CO)NR$^7$R$^8$, —(SO$_2$)R$^9$, —(SO)R$^9$, —SR$^9$, —(SO$_2$)NR$^7$R$^8$, —NR$^7$(SO$_2$)R$^9$, —((SO)=NR$^{11}$)R$^{10}$, —N=(SO)R$^9$R$^{10}$, —(PO)(OR$^7$)$_2$, —(PO)(OR$^7$)R$^{10}$ or —(PO)(R$^{10}$)$_2$,
  wherein each C$_1$-C$_4$-alkyl, C$_1$-C$_4$-alkoxy, 3- to 6-membered heterocycloalkoxy, C$_3$-C$_6$-cycloalkyl, 3- to 6-membered heterocycloalkyl, phenyl or heteroaryl is optionally substituted, one or more times, independently from each other, with halogen, OH, —CN, —NR$^7$R$^8$, C$_1$-C$_4$-alkyl, C$_1$-C$_4$-haloalkyl, C$_1$-C$_4$-hydroxyalkyl, phenyl-C$_1$-C$_2$-alkyl, (C$_1$-C$_4$-alkoxy)-(C$_1$-C$_4$-alkyl)-, C$_1$-C$_4$-alkoxy, C$_3$-C$_6$-cycloalkyl, 3- to 6-membered heterocycloalkyl, phenyl, —(CO)OR$^7$, —(CO)NR$^7$R$^8$, —NR$^7$(CO)R$^{10}$, —NR$^8$(CO)OR$^7$, —NR$^8$(CO) NR$^7$R$^8$, —(SO$_2$)R$^9$, —(SO)R$^9$, —SR$^9$, —(SO$_2$)NR$^7$R$^8$, —NR$^7$(SO$_2$)R$^9$, —((SO)=NR$^{11}$)R$^{10}$, —N=(SO)R$^9$R$^{10}$, with a heteroaryl group which is optionally substituted one or more times with C$_1$-C$_4$-alkyl, or
  wherein two substituents of said phenyl group attached to two adjacent phenyl ring atoms are linked to one another to jointly form a methylenedioxy, ethylenedioxy, ethyleneoxy or trimethyleneoxy group;
R$^3$ and R$^4$ are independently hydrogen or methyl;
R$^5$ is C$_1$-C$_4$-alkyl;
R$^7$ and R$^8$ are independently hydrogen, C$_1$-C$_6$-alkyl, C$_3$-C$_6$-cycloalkyl, phenyl or phenyl-CH$_2$—, which phenyl is optionally substituted, one or more times, with halogen; or
R$^7$ and R$^8$ together represent a 5- or 6-membered cyclic amine group, which is optionally substituted, one or more times, independently from each other, with a substituent selected from C$_1$-C$_4$-alkyl, C$_1$-C$_4$-haloalkyl, said 5- or 6-membered cyclic amine group optionally containing one further heteroatom selected from the group consisting of O, N and S;
R$^9$ is C$_1$-C$_4$-alkyl;
R$^{10}$ is C$_1$-C$_4$-alkyl; or
R$^9$ and R$^{10}$ together, in case of —N=(SO)R$^9$R$^{10}$ group, represent a 5- to 6-membered heterocycloalkyl group; and
R$^{11}$ is hydrogen or C$_1$-C$_4$-alkyl,
or a stereoisomer, a tautomer, an N-oxide, a hydrate, a solvate, or a salt thereof, or a mixture of same.

3. The compound according to claim 1, wherein the compound of formula (I) is a compound of formula (Ib)

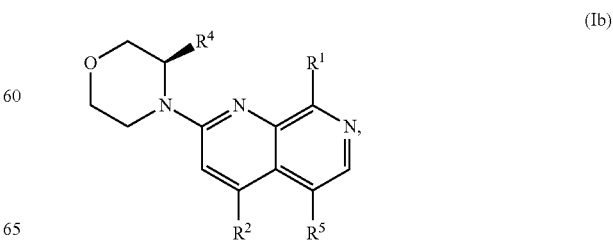

wherein:
$R^1$ is a group:

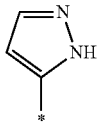

wherein * indicates the point of attachment of said group with the rest of the molecule;
$R^2$ is $NR^7R^8$, $C_1$-$C_4$-alkoxy, $C_4$-$C_6$-cycloalkenyl, 6-membered heterocycloalkyl, phenyl, heteroaryl, —(CO)O$R^7$, —N=(SO)$R^9R^{10}$, —(PO)(O$R^7$)$R^{10}$ or —(PO)($R^{10}$)$_2$,
 wherein each $C_1$-$C_4$-alkoxy, 6-membered heterocycloalkyl, phenyl or heteroaryl is optionally substituted, one or more times, independently from each other, with halogen, OH, —CN, —$NR^7R^8$, $C_1$-$C_4$-alkyl, hydroxymethyl, phenyl-CH$_2$—, methoxymethyl, $C_1$-$C_4$-alkoxy, 6-membered heterocycloalkyl, —(CO)O$R^7$, —(CO)N$R^7R^8$, —(SO$_2$)$R^9$, —(SO)$R^9$, —S$R^9$, —$NR^7$(SO$_2$)$R^9$, or
 wherein two substituents of said phenyl group attached to two adjacent phenyl ring atoms are linked to one another to jointly form an ethylenedioxy group;
$R^4$ is methyl;
$R^5$ is methyl;
$R^7$ and $R^8$ are independently hydrogen, $C_1$-$C_6$-alkyl, cyclopropyl, phenyl or phenyl-CH$_2$—, which phenyl is optionally substituted, one or more times, with halogen; or
$R^7$ and $R^8$ together represent a 5-membered cyclic amine group;
$R^9$ is methyl or ethyl; and
$R^{10}$ is methyl or ethyl; or
$R^9$ and $R^{10}$ together, in case of —N=(SO)$R^9R^{10}$ group, represent a 5-membered heterocycloalkyl group;
or a stereoisomer, a tautomer, an N-oxide, a hydrate, a solvate, or a salt thereof, or a mixture of same.

4. The compound according to claim 1, wherein the compound of formula (I) is a compound of formula (Ib),

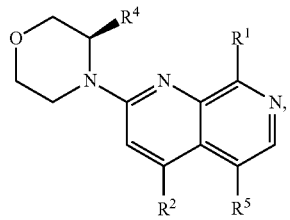

(Ib)

wherein:
$R^1$ is a group:

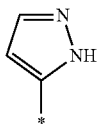

wherein * indicates the point of attachment of said group with the rest of the molecule;

$R^2$ is N-methyl-(2,2-dimethylpropyl), propan-2-yloxy, cyclopent-1-en-1-yl, 6-membered heterocycloalkyl, phenyl, heteroaryl, —(CO)O-methyl, —N=(SO)diethyl, —N=(SO)(CH$_2$)$_4$, —(PO)(O-ethyl)methyl, —(PO)(O-(2-methyl-propyl))methyl or (PO)(methyl)$_2$,
 wherein each 6-membered heterocycloalkyl, phenyl or heteroaryl is optionally substituted, one or more times, independently from each other, with halogen, OH, —CN, —$NR^7R^8$, $C_1$-$C_4$-alkyl, hydroxymethyl, phenyl-CH$_2$—, methoxymethyl, $C_1$-$C_4$-alkoxy, 6-membered heterocycloalkyl, —(CO)O$R^7$, —(CO)N$R^7R^8$, —(SO$_2$)$R^9$, —(SO)$R^9$, —S$R^9$, —$NR^7$(SO$_2$)$R^9$, or
 wherein two substituents of said phenyl group attached to two adjacent phenyl ring atoms are linked to one another to jointly form an ethylenedioxy group;
$R^4$ is methyl;
$R^5$ is methyl;
$R^7$ and $R^8$ are independently hydrogen, $C_1$-$C_5$-alkyl, cyclopropyl, phenyl or unsubstituted phenyl-CH$_2$—, which phenyl is optionally substituted, one or more times, with halogen; or
$R^7$ and $R^8$ together represent a 5-membered cyclic amine group;
$R^9$ is methyl or ethyl; and
$R^{10}$ is methyl or ethyl; or
$R^9$ and $R^{10}$ together, in case of —N=(SO)$R^9R^{10}$ group, represent a tetramethylene group;
or a stereoisomer, a tautomer, an N-oxide, a hydrate, a solvate, or a salt thereof, or a mixture of same.

5. The compound according to claim 1, wherein the compound of formula (I) is a compound of formula (Ib),

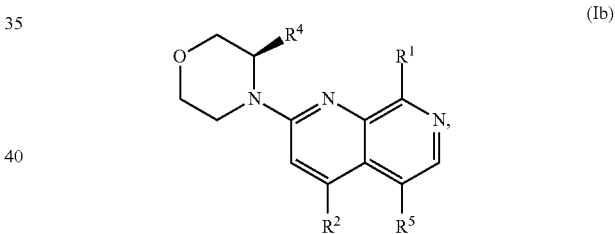

(Ib)

wherein:
$R^1$ is a group:

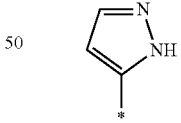

wherein * indicates the point of attachment of said group with the rest of the molecule;
$R^2$ is propan-2-yloxy, —N=(SO)diethyl, —(PO)(O-ethyl)methyl, 1-methyl-1H-pyrazol-5-yl, morpholin-4-yl, 4-(hydroxymethyl)piperidin-1-yl, 4-(methyl sulfonyl)piperazin-1-yl, 1-methyl-1H-imidazol-5-yl or 2-methyl-1,3-thiazol-5-yl;
$R^4$ is methyl; and
$R^5$ is methyl,
or a stereoisomer, a tautomer, an N-oxide, a hydrate, a solvate, or a salt thereof, or a mixture of same.

6. The compound according to claim 1, wherein the compound is selected from the group consisting of:

5-methyl-2-[(3R)-3-methylmorpholin-4-yl]-4-(propan-2-yloxy)-8-(1H-pyrazol-5-yl)-1,7-naphthyridine;
5-methyl-2-[(3R)-3-methylmorpholin-4-yl]-4-(1-methyl-1H-pyrazol-5-yl)-8-(1H-pyrazol-5-yl)-1,7-naphthyridine;
4-(2-fluoropyridin-3-yl)-5-methyl-2-[(3R)-3-methylmorpholin-4-yl]-8-(1H-pyrazol-5-yl)-1,7-naphthyridine;
5-methyl-4-[2-methyl-6-(methyl sulfonyl)pyridin-3-yl]-2-[(3R)-3-methylmorpholin-4-yl]-8-(1H-pyrazol-5-yl)-1,7-naphthyridine;
4-(2-chloro-1-methyl-1H-imidazol-5-yl)-5-methyl-2-[(3R)-3-methylmorpholin-4-yl]-8-(1H-pyrazol-5-yl)-1,7-naphthyridine;
4-[2-fluoro-4-(piperazin-1-yl)phenyl]-5-methyl-2-[(3R)-3-methylmorpholin-4-yl]-8-(1H-pyrazol-5-yl)-1,7-naphthyridine;
4-(2,3-difluorophenyl)-5-methyl-2-[(3R)-3-methylmorpholin-4-yl]-8-(1H-pyrazol-5-yl)-1,7-naphthyridine;
N-5-methyl-2-[(3R)-3-methylmorpholin-4-yl]-8-(1H-pyrazol-5-yl)-1,7-naphthyridin-4-yltetrahydro-1H-1$\lambda^4$-thiophen-1-imine 1-oxide;
4-[diethyl(oxido)-$\lambda^6$-sulfanylidene]amino-5-methyl-2-[(3R)-3-methylmorpholin-4-yl]-8-(1H-pyrazol-5-yl)-1,7-naphthyridine;
5-methyl-2-[(3R)-3-methylmorpholin-4-yl]-4-(morpholin-4-yl)-8-(1H-pyrazol-5-yl)-1,7-naphthyridine;
(1-{5-methyl-2-[(3R)-3-methylmorpholin-4-yl]-8-(1H-pyrazol-5-yl)-1,7-naphthyridin-4-yl}piperidin-4-yl)methanol;
5-methyl-2-[(3R)-3-methylmorpholin-4-yl]-4-[4-(methyl sulfonyl)piperazin-1-yl]-8-(1H-pyrazol-5-yl)-1,7-naphthyridine;
N-(2,2-dimethylpropyl)-N, 5-dimethyl-2-[(3R)-3-methylmorpholin-4-yl]-8-(1H-pyrazol-5-yl)-1,7-naphthyridin-4-amine;
methyl 5-methyl-2-[(3R)-3-methylmorpholin-4-yl]-8-(1H-pyrazol-5-yl)-1,7-naphthyridine-4-carboxylate;
5-methyl-4-(1-methyl-1H-imidazol-5-yl)-2-[(3R)-3-methylmorpholin-4-yl]-8-(1H-pyrazol-5-yl)-1,7-naphthyridine;
5-methyl-2-[(3R)-3-methylmorpholin-4-yl]-4-(2-methyl-1,3-thiazol-5-yl)-8-(1H-pyrazol-5-yl)-1,7-naphthyridine;
ethyl methyl{5-methyl-2-[(3R)-3-methylmorpholin-4-yl]-8-(1H-pyrazol-5-yl)-1,7-naphthyridin-4-yl}phosphinate;
4-(dimethylphosphoryl)-5-methyl-2-[(3R)-3-methylmorpholin-4-yl]-8-(1H-pyrazol-5-yl)-1,7-naphthyridine;
2-methylpropyl methyl{5-methyl-2-[(3R)-3-methylmorpholin-4-yl]-8-(1H-pyrazol-5-yl)-1,7-naphthyridin-4-yl}phosphinate;
5-methyl-2-[(3R)-3-methylmorpholin-4-yl]-4-phenyl-8-(1H-pyrazol-5-yl)-1,7-naphthyridine;
4-(2,3-dihydro-1,4-benzodioxin-6-yl)-5-methyl-2-[(3R)-3-methylmorpholin-4-yl]-8-(1H-pyrazol-5-yl)-1,7-naphthyridine;
4-(2,4-dichlorophenyl)-5-methyl-2-[(3R)-3-methylmorpholin-4-yl]-8-(1H-pyrazol-5-yl)-1,7-naphthyridine;
(3-{5-methyl-2-[(3R)-3-methylmorpholin-4-yl]-8-(1H-pyrazol-5-yl)-1,7-naphthyridin-4-yl}phenyl)methanol;
4-(4-fluorophenyl)-5-methyl-2-[(3R)-3-methylmorpholin-4-yl]-8-(1H-pyrazol-5-yl)-1,7-naphthyridine;
4-(4-methoxyphenyl)-5-methyl-2-[(3R)-3-methylmorpholin-4-yl]-8-(1H-pyrazol-5-yl)-1,7-naphthyridine;
5-methyl-2-[(3R)-3-methylmorpholin-4-yl]-8-(1H-pyrazol-5-yl)-4-(2,3,5-trifluorophenyl)-1,7-naphthyridine;
4-(6-methoxypyridin-3-yl)-5-methyl-2-[(3R)-3-methylmorpholin-4-yl]-8-(1H-pyrazol-5-yl)-1,7-naphthyridine;
methyl 3-{5-methyl-2-[(3R)-3-methylmorpholin-4-yl]-8-(1H-pyrazol-5-yl)-1,7-naphthyridin-4-yl}benzoate;
5-methyl-2-[(3R)-3-methylmorpholin-4-yl]-4-[4-(methylsulfinyl)phenyl]-8-(1H-pyrazol-5-yl)-1,7-naphthyridine;
4-(2-fluoro-3-methoxyphenyl)-5-methyl-2-[(3R)-3-methylmorpholin-4-yl]-8-(1H-pyrazol-5-yl)-1,7-naphthyridine;
5-methyl-2-[(3R)-3-methylmorpholin-4-yl]-4-[2-(methylsulfonyl)phenyl]-8-(1H-pyrazol-5-yl)-1,7-naphthyridine;
N-(4-{5-methyl-2-[(3R)-3-methylmorpholin-4-yl]-8-(1H-pyrazol-5-yl)-1,7-naphthyridin-4-yl}phenyl)methanesulfonamide;
4-(cyclopent-1-en-1-yl)-5-methyl-2-[(3R)-3-methylmorpholin-4-yl]-8-(1H-pyrazol-5-yl)-1,7-naphthyridine;
5-methyl-2-[(3R)-3-methylmorpholin-4-yl]-8-(1H-pyrazol-5-yl)-4-(quinolin-3-yl)-1,7-naphthyridine;
N,N-dimethyl-4-{5-methyl-2-[(3R)-3-methylmorpholin-4-yl]-8-(1H-pyrazol-5-yl)-1,7-naphthyridin-4-yl}benzamide;
4-(4-chloro-3-methylphenyl)-5-methyl-2-[(3R)-3-methylmorpholin-4-yl]-8-(1H-pyrazol-5-yl)-1,7-naphthyridine;
4-(2,3-dimethoxyphenyl)-5-methyl-2-[(3R)-3-methylmorpholin-4-yl]-8-(1H-pyrazol-5-yl)-1,7-naphthyridine;
4-(4-chloro-2-methoxyphenyl)-5-methyl-2-[(3R)-3-methylmorpholin-4-yl]-8-(1H-pyrazol-5-yl)-1,7-naphthyridine;
5-methyl-2-[(3R)-3-methylmorpholin-4-yl]-4-[4-(methylsulfanyl)phenyl]-8-(1H-pyrazol-5-yl)-1,7-naphthyridine;
N,N-dimethyl-3-{5-methyl-2-[(3R)-3-methylmorpholin-4-yl]-8-(1H-pyrazol-5-yl)-1,7-naphthyridin-4-yl}aniline;
5-methyl-2-[(3R)-3-methylmorpholin-4-yl]-4-[3-(methylsulfonyl)phenyl]-8-(1H-pyrazol-5-yl)-1,7-naphthyridine;
4-(3,5-dimethoxyphenyl)-5-methyl-2-[(3R)-3-methylmorpholin-4-yl]-8-(1H-pyrazol-5-yl)-1,7-naphthyridine;
5-methyl-2-[(3R)-3-methylmorpholin-4-yl]-8-(1H-pyrazol-5-yl)-4-(quinolin-4-yl)-1,7-naphthyridine;
4-(1H-indol-4-yl)-5-methyl-2-[(3R)-3-methylmorpholin-4-yl]-8-(1H-pyrazol-5-yl)-1,7-naphthyridine;
4-(1H-indol-6-yl)-5-methyl-2-[(3R)-3-methylmorpholin-4-yl]-8-(1H-pyrazol-5-yl)-1,7-naphthyridine;
5-methyl-2-[(3R)-3-methylmorpholin-4-yl]-4-(3-methylpyridin-4-yl)-8-(1H-pyrazol-5-yl)-1,7-naphthyridine;
(5-{5-methyl-2-[(3R)-3-methylmorpholin-4-yl]-8-(1H-pyrazol-5-yl)-1,7-naphthyridin-4-yl}thiophen-2-yl)methanol;
2-fluoro-4-{5-methyl-2-[(3R)-3-methylmorpholin-4-yl]-8-(1H-pyrazol-5-yl)-1,7-naphthyridin-4-yl}benzonitrile;
4-(6-fluoropyridin-3-yl)-5-methyl-2-[(3R)-3-methylmorpholin-4-yl]-8-(1H-pyrazol-5-yl)-1,7-naphthyridine;
4-(2-methoxypyridin-3-yl)-5-methyl-2-[(3R)-3-methylmorpholin-4-yl]-8-(1H-pyrazol-5-yl)-1,7-naphthyridine;
5-methyl-2-[(3R)-3-methylmorpholin-4-yl]-4-[2-(propan-2-yl)phenyl]-8-(1H-pyrazol-5-yl)-1,7-naphthyridine;

4-{5-methyl-2-[(3R)-3-methylmorpholin-4-yl]-8-(1H-pyrazol-5-yl)-1,7-naphthyridin-4-yl}benzamide;

(4-{5-methyl-2-[(3R)-3-methylmorpholin-4-yl]-8-(1H-pyrazol-5-yl)-1,7-naphthyridin-4-yl}phenyl)(pyrrolidin-1-yl)methanone;

N-benzyl-4-{5-methyl-2-[(3R)-3-methylmorpholin-4-yl]-8-(1H-pyrazol-5-yl)-1,7-naphthyridin-4-yl}benzamide;

N,N-dimethyl-3-{5-methyl-2-[(3R)-3-methylmorpholin-4-yl]-8-(1H-pyrazol-5-yl)-1,7-naphthyridin-4-yl}benzamide;

4-[3-(methoxymethyl)phenyl]-5-methyl-2-[(3R)-3-methylmorpholin-4-yl]-8-(1H-pyrazol-5-yl)-1,7-naphthyridine;

5-methyl-4-(1-methyl-1H-indol-5-yl)-2-[(3R)-3-methylmorpholin-4-yl]-8-(1H-pyrazol-5-yl)-1,7-naphthyridine;

4-(isoquinolin-4-yl)-5-methyl-2-[(3R)-3-methylmorpholin-4-yl]-8-(1H-pyrazol-5-yl)-1,7-naphthyridine;

4-(5-methoxypyridin-3-yl)-5-methyl-2-[(3R)-3-methylmorpholin-4-yl]-8-(1H-pyrazol-5-yl)-1,7-naphthyridine;

5-methyl-2-[(3R)-3-methylmorpholin-4-yl]-4-[3-(propan-2-yloxy)phenyl]-8-(1H-pyrazol-5-yl)-1,7-naphthyridine;

5-methyl-2-[(3R)-3-methylmorpholin-4-yl]-4-(4-methylpyridin-3-yl)-8-(1H-pyrazol-5-yl)-1,7-naphthyridine;

N-tert-butyl-4-{5-methyl-2-[(3R)-3-methylmorpholin-4-yl]-8-(1H-pyrazol-5-yl)-1,7-naphthyridin-4-yl}benzamide;

N-cyclopropyl-4-{5-methyl-2-[(3R)-3-methylmorpholin-4-yl]-8-(1H-pyrazol-5-yl)-1,7-naphthyridin-4-yl}benzamide;

3-methyl-4-{5-methyl-2-[(3R)-3-methylmorpholin-4-yl]-8-(1H-pyrazol-5-yl)-1,7-naphthyridin-4-yl}phenol;

4-[4-(methoxymethyl)phenyl]-5-methyl-2-[(3R)-3-methylmorpholin-4-yl]-8-(1H-pyrazol-5-yl)-1,7-naphthyridine; and N-methyl-4-{5-methyl-2-[(3R)-3-methylmorpholin-4-yl]-8-(1H-pyrazol-5-yl)-1,7-naphthyridin-4-yl}benzamide;

or a stereoisomer, a tautomer, an N-oxide, a hydrate, a solvate, or a salt thereof, or a mixture of same.

7. A method for treatment of cervical cancer in a human or animal in need thereof, comprising administering an effective amount of a compound of formula (I) according to claim 1 to the human or animal.

8. A pharmaceutical composition comprising a compound of formula (I) according to claim 1 and one or more pharmaceutically acceptable excipient(s).

9. A method for treatment of cervical cancer in a human or animal in need thereof, comprising administering an effective amount of a pharmaceutical composition according to claim 8 to the human or animal.

10. A pharmaceutical combination comprising:
    one or more active ingredient(s) selected from a compound of formula (I) according to claim 1, and
    one or more active ingredient(s) selected from antihyperproliferative, cytostatic or cytotoxic substances for treatment of cancers.

11. A pharmaceutical composition comprising a compound of formula (Ib) according to claim 3 and one or more pharmaceutically acceptable excipient(s).

12. A pharmaceutical combination comprising:
    one or more active ingredient(s) selected from a compound of formula (Ib) according to claim 3, and
    one or more active ingredient(s) selected from antihyperproliferative, cytostatic or cytotoxic substances for treatment of cancers.

13. A method for treatment of cervical cancer in a human or animal in need thereof, comprising administering an effective amount of a compound of formula (Ib) according to claim 3 to the human or animal.

14. A method for treatment of cervical cancer in a human or animal in need thereof, comprising administering an effective amount of a pharmaceutical combination according to claim 12 to the human or animal.

* * * * *